(12) United States Patent
Ginns et al.

(10) Patent No.: US 6,897,022 B2
(45) Date of Patent: May 24, 2005

(54) SUSCEPTABILITY AND RESISTANCE GENES FOR BIPOLAR AFFECTIVE DISORDER

(75) Inventors: Edward I. Ginns, Shrewsbury, MA (US); Janice A. Egeland, Hershey, PA (US); Steven M. Paul, Carmel, IN (US)

(73) Assignees: University of Miami, Miami, FL (US); The United States of America as represented by the Secretary of Health & Human Services, Rockville, MD (US)

( * ) Notice: Subject to any disclaimer, the term of this patent is extended or adjusted under 35 U.S.C. 154(b) by 0 days.

(21) Appl. No.: 09/881,012

(22) Filed: Jun. 13, 2001

(65) Prior Publication Data

US 2002/0192655 A1 Dec. 19, 2002
US 2004/0248086 A9 Dec. 19, 2002

Related U.S. Application Data

(63) Continuation of application No. 09/175,158, filed on Oct. 19, 1998, now abandoned, which is a continuation-in-part of application No. 08/827,568, filed on Mar. 28, 1997, now abandoned.
(60) Provisional application No. 60/062,924, filed on Oct. 20, 1997, and provisional application No. 60/014,334, filed on Mar. 29, 1996.

(51) Int. Cl.$^7$ ............................. C07H 21/04; C12Q 1/68
(52) U.S. Cl. .......................... 435/6; 435/91.2; 536/23.1
(58) Field of Search .................. 435/6, 91.12; 536/23.1

(56) References Cited

FOREIGN PATENT DOCUMENTS

WO WO 99/04825 2/1999
WO WO 99/06539 2/1999

OTHER PUBLICATIONS

Strachan T., "The Human Genome", 1992, Biosis Scientific Publishers, LTD., Oxford, England, pp. 71–96.
Stine et al., "Initial Genome Screen for Bipolar Disorder in the NIMH Genetics Initiative Pedigrees: Chromosomes 2, 11, 13, 14 and X", American Journal of Medical Genetics (Neuropsychiatric Genetics), (1997), 74:263–269.
Rice et al., "Initial Genome Scan of the NIMH Genetics Initiative Bipolar Pedigrees: Chromosomes 1, 6, 8, 10, and 12", American Journal of Medical Genetics (Neuropsychiatric Genetics), (1977), 74:247–253.
Blackwood et al., "A Locus for Bipolar Affective Disorder on Chromosome 4p", Nature Genetics, vol. 12, Apr. 1996, pps. 427–430.
Berrettini, Wade, "Progress and Pitfalls: Bipolar Molecular Linkage Studies", Affective Disorders, (1998), 50:287–297.
Ginns et al., "A Genome–Wide Search for Chromosomal Loci Linked to Mental Health Wellness in Relatives at High Risk for Bipolar Affective Disorder Among the Old Order Amish", Proc. Natl. Acad. Sci., vol. 25, pp. 15531–15536.

Primary Examiner—Jeanine Goldberg
(74) Attorney, Agent, or Firm—Venable LLP; Ann S. Hobbs; Nancy Axelrod

(57) ABSTRACT

Chromosomal regions comprising loci associated with susceptibility and resistance to bipolar affective disorder have been identified. Methods and compositions are provided for determining the contribution of these chromosomal regions to bipolar affective disorder in an affected family, for determining in an affected family a genotype associated with increased or decreased susceptibility or resistance to bipolar illness, and for assessing an increased or decreased risk of developing bipolar illness for a tested individual from an affected family.

12 Claims, 13 Drawing Sheets

* = NG markers/values

SIBPAL P

| | | | |
|---|---|---|---|
| | D13S56h1 | | 0.0 |
| | | 0.0 | |
| | D13S56h2 | | 0.0 |
| | | 11.6 | |
| 0.0865 | * D13S291 | | 11.6 |
| | | 6.8 | |
| | D13S37 GATA125CO4 | | 18.4 |
| | | 2.8 | |
| 0.0171 | * D13S218 | | |
| 0.4336 | D13S894 | | 21.2 |
| | | 6.1 | |
| | * D13S1m | | 27.3 |
| 0.0003 | | 0.0 | |
| | * D13S1t | | 27.3 |
| | | 5.2 | |
| 0.4905 | * D13S171 | | 32.5 |
| | | 3.8 | |
| 0.1593 | D13S260 | | 36.3 |
| | | 10.4 | |
| | D13S221 | | 46.7 |
| | | 6.5 | |
| | D13S232 | | 53.2 |

Figure 4

SIBPAL P value

| | Marker | Distance | Position |
|---|---|---|---|
| | D4S412 | | 0.0 |
| 0.5241 | D4S2935 | 13.6 | 13.6 |
| | D4S431 | 1.2 | 14.8 |
| | D4S431a | 0.9 | 15.7 |
| 0.0002 | D4S2366 | 1.0 | 16.7 |
| | D4S394a | 3.2 | 19.8 |
| 0.0015 | D4S3007 | 2.1 | |
| 0.0035 | D4S394 | | 21.9 |
| 0.0000 | D4S2949 | 9.4 | 31.3 |
| 0.0626 | D4S1605 | 2.5 | |
| 0.0005 | D4S1582 | | 33.8 |
| | D4S107m | 0.5 | |
| | D4S403 | | 34.3 |
| 0.0002 | D4S419 | 7.6 | 41.9 |
| 0.0004 | D4S404 | 6.2 | 48.1 |
| | D4S391 | 6.6 | 54.7 |
| | D4S405 | 12.1 | 66.8 |

Figure 6

SIBPAL P

| | Marker | | Distance | Position |
|---|---|---|---|---|
| | D4S100 | — | 7.4 | 0.0 |
| | D4S406 | — | | 7.4 |
| | D4S1611 | | 3.9 | |
| | D4S101t | | | |
| | UT7739 | — | | 11.4 |
| | D4S1573 | — | 3.7 | 15.0 |
| <0.0001 | D4S402 | — | 2.6 | 17.6 |
| 0.0001 | D4S109 | | 1.2 | |
| | D4S427 | — | | 18.9 |
| | D4S1615 | — | 8.6 | 27.5 |
| | D4S2959 | — | 8.4 | 35.9 |
| | D4S1576 | — | 5.6 | 41.5 |
| | D4S422 | — | 4.5 | 46.0 |
| | D4S2423 | | 1.4 | |
| | D4S422a | — | 1.8 | 47.4 |
| <0.0001 | D4S175 | — | | 49.2 |
| <0.0001 | D4S397 | | 2.6 | |
| | D4S3334 | — | 2.5 | 51.8 |
| | D4S1644 | — | 3.4 | 54.3 |
| | D4S192 | | | |
| | D4S1565 | | | |
| | UT2147 | — | | 57.7 |
| 0.0003 | D4S424 | — | 2.7 | 60.4 |
| | D4S420 | | 2.2 | |
| | D4S1625 | — | | 62.6 |
| | UT1264 | — | 4.8 | 67.3 |
| | D4S413 | — | 15.3 | 82.7 |
| | GATA8A05 | | | |

Figure 7

Figure 1. Genetic, Physical, and Transcription Unit Mapping of the *Clock* Locus

SEQUENCE LISTING

<160> NUMBER OF SEQ ID NOS: 240

<210> SEQ ID NO 1
<211> LENGTH: 18
<212> TYPE: DNA
<213> ORGANISM: Artificial Sequence
<220> FEATURE:
<223> OTHER INFORMATION: D6S344 forward primer

<400> SEQUENCE: 1
ctccagcctg ggtcacta                                          18

<210> SEQ ID NO 2
<211> LENGTH: 25
<212> TYPE: DNA
<213> ORGANISM: Artificial Sequence
<220> FEATURE:
<223> OTHER INFORMATION: D6S344 reverse primer

<400> SEQUENCE: 2
ctaatgcatg acaataatat ttcca                                  25

<210> SEQ ID NO 3
<211> LENGTH: 20
<212> TYPE: DNA
<213> ORGANISM: Artificial Sequence
<220> FEATURE:
<223> OTHER INFORMATION: D6S89 primer

<400> SEQUENCE: 3
acctaagcga ctgcctaaac                                        20

<210> SEQ ID NO 4
<211> LENGTH: 20
<212> TYPE: DNA
<213> ORGANISM: Artificial Sequence
<220> FEATURE:
<223> OTHER INFORMATION: D6S89 primer

<400> SEQUENCE: 4
cttgttcatc tgccttgtgc                                        20

<210> SEQ ID NO 5
<211> LENGTH: 22
<212> TYPE: DNA
<213> ORGANISM: Artificial Sequence
<220> FEATURE:
<223> OTHER INFORMATION: D6S89 primer

<400> SEQUENCE: 5
agtctcatgt gacacaaggc ag                                     22

<210> SEQ ID NO 6
<211> LENGTH: 22
<212> TYPE: DNA
<213> ORGANISM: Artificial Sequence
<220> FEATURE:
<223> OTHER INFORMATION: D6S89 primer

<400> SEQUENCE: 6
tgtaacctgg aagtaaggca tg                                     22

```
<210> SEQ ID NO 7
<211> LENGTH: 16
<212> TYPE: DNA
<213> ORGANISM: Artificial Sequence
<220> FEATURE:
<223> OTHER INFORMATION: D13S171 primer

<400> SEQUENCE: 7
tagggccatc cattct                                                    16

<210> SEQ ID NO 8
<211> LENGTH: 20
<212> TYPE: DNA
<213> ORGANISM: Artificial Sequence
<220> FEATURE:
<223> OTHER INFORMATION: D13S171 primer

<400> SEQUENCE: 8
cctaccattg acactctcag                                                20

<210> SEQ ID NO 9
<211> LENGTH: 21
<212> TYPE: DNA
<213> ORGANISM: Artificial Sequence
<220> FEATURE:
<223> OTHER INFORMATION: 7F12-Ia primer

<400> SEQUENCE: 9
tgtaactatt gggaggaaag a                                              21

<210> SEQ ID NO 10
<211> LENGTH: 21
<212> TYPE: DNA
<213> ORGANISM: Artificial Sequence
<220> FEATURE:
<223> OTHER INFORMATION: 7F12-IIa primer

<400> SEQUENCE: 10
ttgtgtagga ctctctagtt t                                              21

<210> SEQ ID NO 11
<211> LENGTH: 20
<212> TYPE: DNA
<213> ORGANISM: Artificial Sequence
<220> FEATURE:
<223> OTHER INFORMATION: D13S218 primer

<400> SEQUENCE: 11
gatttgaaaa tgagcagtcc                                                20

<210> SEQ ID NO 12
<211> LENGTH: 20
<212> TYPE: DNA
<213> ORGANISM: Artificial Sequence
<220> FEATURE:
<223> OTHER INFORMATION: D13S218 primer

<400> SEQUENCE: 12
gtcgggcact acgtttatct                                                20

<210> SEQ ID NO 13
<211> LENGTH: 20
<212> TYPE: DNA
<213> ORGANISM: Artificial Sequence
<220> FEATURE:
<223> OTHER INFORMATION: D15S117 primer
```

-continued

```
<400> SEQUENCE: 13
gcaccaacaa cttatcccaa                                             20

<210> SEQ ID NO 14
<211> LENGTH: 20
<212> TYPE: DNA
<213> ORGANISM: Artificial Sequence
<220> FEATURE:
<223> OTHER INFORMATION: D15S117 primer

<400> SEQUENCE: 14
ccctaagggg tctctgaaga                                             20

<210> SEQ ID NO 15
<211> LENGTH: 18
<212> TYPE: DNA
<213> ORGANISM: Artificial Sequence
<220> FEATURE:
<223> OTHER INFORMATION: D6S1600 forward primer

<400> SEQUENCE: 15
agcttgtgca tgtgtgca                                               18

<210> SEQ ID NO 16
<211> LENGTH: 18
<212> TYPE: DNA
<213> ORGANISM: Artificial Sequence
<220> FEATURE:
<223> OTHER INFORMATION: D6S1600 reverse primer

<400> SEQUENCE: 16
caaagtccca gcaggttc                                               18

<210> SEQ ID NO 17
<211> LENGTH: 18
<212> TYPE: DNA
<213> ORGANISM: Artificial Sequence
<220> FEATURE:
<223> OTHER INFORMATION: D15S123 primer

<400> SEQUENCE: 17
agctgaaccc aatggact                                               18

<210> SEQ ID NO 18
<211> LENGTH: 18
<212> TYPE: DNA
<213> ORGANISM: Artificial Sequence
<220> FEATURE:
<223> OTHER INFORMATION: D15S123 primer

<400> SEQUENCE: 18
tttcatgcca ccaacaaa                                               18

<210> SEQ ID NO 19
<211> LENGTH: 25
<212> TYPE: DNA
<213> ORGANISM: Artificial Sequence
<220> FEATURE:
<223> OTHER INFORMATION: D15S982 primer

<400> SEQUENCE: 19
atgtttaaat taataacgtg acagt                                       25
```

```
<210> SEQ ID NO 20
<211> LENGTH: 20
<212> TYPE: DNA
<213> ORGANISM: Artificial Sequence
<220> FEATURE:
<223> OTHER INFORMATION: D15S982 primer

<400> SEQUENCE: 20
gacttcatct ggattcacaa                                          20

<210> SEQ ID NO 21
<211> LENGTH: 25
<212> TYPE: DNA
<213> ORGANISM: Artificial Sequence
<220> FEATURE:
<223> OTHER INFORMATION: D15S119 primer

<400> SEQUENCE: 21
aacagaaaat ccgtaacata acata                                    25

<210> SEQ ID NO 22
<211> LENGTH: 22
<212> TYPE: DNA
<213> ORGANISM: Artificial Sequence
<220> FEATURE:
<223> OTHER INFORMATION: D15S119 primer

<400> SEQUENCE: 22
acttttgtgc catttagaga tt                                       22

<210> SEQ ID NO 23
<211> LENGTH: 22
<212> TYPE: DNA
<213> ORGANISM: Artificial Sequence
<220> FEATURE:
<223> OTHER INFORMATION: D15S1032 primer

<400> SEQUENCE: 23
agctttaact tccatgagtt tc                                       22

<210> SEQ ID NO 24
<211> LENGTH: 21
<212> TYPE: DNA
<213> ORGANISM: Artificial Sequence
<220> FEATURE:
<223> OTHER INFORMATION: D15S1032 primer

<400> SEQUENCE: 24
ctaatctctg gtgcatagtg a                                        21

<210> SEQ ID NO 25
<211> LENGTH: 24
<212> TYPE: DNA
<213> ORGANISM: Artificial Sequence
<220> FEATURE:
<223> OTHER INFORMATION: D15S208 primer

<400> SEQUENCE: 25
tcttagcagt aattgtcact cctt                                     24

<210> SEQ ID NO 26
<211> LENGTH: 20
<212> TYPE: DNA
<213> ORGANISM: Artificial Sequence
<220> FEATURE:
<223> OTHER INFORMATION: D15S208 primer
```

```
<400> SEQUENCE: 26
acataccatc ccatggttat                                              20

<210> SEQ ID NO 27
<211> LENGTH: 22
<212> TYPE: DNA
<213> ORGANISM: Artificial Sequence
<220> FEATURE:
<223> OTHER INFORMATION: D15S161 primer

<400> SEQUENCE: 27
tctgtgattt tgccattatg ag                                           22

<210> SEQ ID NO 28
<211> LENGTH: 25
<212> TYPE: DNA
<213> ORGANISM: Artificial Sequence
<220> FEATURE:
<223> OTHER INFORMATION: D15S161 primer

<400> SEQUENCE: 28
taaactggaa tttttgacta tgagc                                        25

<210> SEQ ID NO 29
<211> LENGTH: 20
<212> TYPE: DNA
<213> ORGANISM: Artificial Sequence
<220> FEATURE:
<223> OTHER INFORMATION: D15S143 primer

<400> SEQUENCE: 29
ctaaggaggc aacagcaaag                                              20

<210> SEQ ID NO 30
<211> LENGTH: 25
<212> TYPE: DNA
<213> ORGANISM: Artificial Sequence
<220> FEATURE:
<223> OTHER INFORMATION: D15S143 primer

<400> SEQUENCE: 30
atgtaaagac tggtatctgt agcac                                        25

<210> SEQ ID NO 31
<211> LENGTH: 25
<212> TYPE: DNA
<213> ORGANISM: Artificial Sequence
<220> FEATURE:
<223> OTHER INFORMATION: D15S1017 primer
<221> NAME/KEY: modified_base
<222> LOCATION: (12)...(12)
<223> OTHER INFORMATION: n = g,a,c or t

<400> SEQUENCE: 31
tcaagtaagg cnattattat acaga                                        25

<210> SEQ ID NO 32
<211> LENGTH: 20
<212> TYPE: DNA
<213> ORGANISM: Artificial Sequence
<220> FEATURE:
<223> OTHER INFORMATION: D15S1017 primer

<400> SEQUENCE: 32
ccacaagctg gactgagaat                                              20
```

```
<210> SEQ ID NO 33
<211> LENGTH: 20
<212> TYPE: DNA
<213> ORGANISM: Artificial Sequence
<220> FEATURE:
<223> OTHER INFORMATION: D15S990 primer

<400> SEQUENCE: 33
ctgaacaggt tgaagtgtcc                                              20

<210> SEQ ID NO 34
<211> LENGTH: 18
<212> TYPE: DNA
<213> ORGANISM: Artificial Sequence
<220> FEATURE:
<223> OTHER INFORMATION: D15S990 primer

<400> SEQUENCE: 34
cttggaatgc ctgaggac                                                18

<210> SEQ ID NO 35
<211> LENGTH: 20
<212> TYPE: DNA
<213> ORGANISM: Artificial Sequence
<220> FEATURE:
<223> OTHER INFORMATION: D15S1024 primer

<400> SEQUENCE: 35
ctaagtcctc cacactagcc                                              20

<210> SEQ ID NO 36
<211> LENGTH: 18
<212> TYPE: DNA
<213> ORGANISM: Artificial Sequence
<220> FEATURE:
<223> OTHER INFORMATION: D15S1024 primer

<400> SEQUENCE: 36
ctaaaatggg aacagggc                                                18

<210> SEQ ID NO 37
<211> LENGTH: 18
<212> TYPE: DNA
<213> ORGANISM: Artificial Sequence
<220> FEATURE:
<223> OTHER INFORMATION: D15S1039 primer

<400> SEQUENCE: 37
tgccggtagt aacatctg                                                18

<210> SEQ ID NO 38
<211> LENGTH: 22
<212> TYPE: DNA
<213> ORGANISM: Artificial Sequence
<220> FEATURE:
<223> OTHER INFORMATION: D15S1039 primer

<400> SEQUENCE: 38
ccaaggataa agtatttgtg tc                                           22

<210> SEQ ID NO 39
<211> LENGTH: 24
<212> TYPE: DNA
<213> ORGANISM: Artificial Sequence
<220> FEATURE:
<223> OTHER INFORMATION: D15S992 primer
```

```
<400> SEQUENCE: 39
agctgagaaa tgccttctat aaat                                    24

<210> SEQ ID NO 40
<211> LENGTH: 18
<212> TYPE: DNA
<213> ORGANISM: Artificial Sequence
<220> FEATURE:
<223> OTHER INFORMATION: D15S992 primer

<400> SEQUENCE: 40
gagggccacc ttgatagt                                           18

<210> SEQ ID NO 41
<211> LENGTH: 23
<212> TYPE: DNA
<213> ORGANISM: Artificial Sequence
<220> FEATURE:
<223> OTHER INFORMATION: D15S978 primer

<400> SEQUENCE: 41
agcttcatac actgaaattg ttg                                     23

<210> SEQ ID NO 42
<211> LENGTH: 17
<212> TYPE: DNA
<213> ORGANISM: Artificial Sequence
<220> FEATURE:
<223> OTHER INFORMATION: D15S978 primer

<400> SEQUENCE: 42
caccgggaaa ccttgat                                            17

<210> SEQ ID NO 43
<211> LENGTH: 20
<212> TYPE: DNA
<213> ORGANISM: Artificial Sequence
<220> FEATURE:
<223> OTHER INFORMATION: D15S126 primer

<400> SEQUENCE: 43
gtgagccaag atggcactac                                         20

<210> SEQ ID NO 44
<211> LENGTH: 20
<212> TYPE: DNA
<213> ORGANISM: Artificial Sequence
<220> FEATURE:
<223> OTHER INFORMATION: D15S126 primer

<400> SEQUENCE: 44
gccagcaata atgggaagtt                                         20

<210> SEQ ID NO 45
<211> LENGTH: 22
<212> TYPE: DNA
<213> ORGANISM: Artificial Sequence
<220> FEATURE:
<223> OTHER INFORMATION: D15S1003 primer

<400> SEQUENCE: 45
tggtagtacc cctggatacc tg                                      22
```

```
<210> SEQ ID NO 46
<211> LENGTH: 24
<212> TYPE: DNA
<213> ORGANISM: Artificial Sequence
<220> FEATURE:
<223> OTHER INFORMATION: D15S1003 primer

<400> SEQUENCE: 46
aatctttgtg gatatggctc tgct                                    24

<210> SEQ ID NO 47
<211> LENGTH: 20
<212> TYPE: DNA
<213> ORGANISM: Artificial Sequence
<220> FEATURE:
<223> OTHER INFORMATION: D15S121 primer

<400> SEQUENCE: 47
ttgtatcagg gatttggtta                                         20

<210> SEQ ID NO 48
<211> LENGTH: 20
<212> TYPE: DNA
<213> ORGANISM: Artificial Sequence
<220> FEATURE:
<223> OTHER INFORMATION: D15S121 primer

<400> SEQUENCE: 48
tgttgtcgct tcagtacata                                         20

<210> SEQ ID NO 49
<211> LENGTH: 18
<212> TYPE: DNA
<213> ORGANISM: Artificial Sequence
<220> FEATURE:
<223> OTHER INFORMATION: D15S1016 primer

<400> SEQUENCE: 49
gatccgtcac ataatggc                                           18

<210> SEQ ID NO 50
<211> LENGTH: 18
<212> TYPE: DNA
<213> ORGANISM: Artificial Sequence
<220> FEATURE:
<223> OTHER INFORMATION: D15S1016 primer

<400> SEQUENCE: 50
acacctcagc tttcctgg                                           18

<210> SEQ ID NO 51
<211> LENGTH: 20
<212> TYPE: DNA
<213> ORGANISM: Artificial Sequence
<220> FEATURE:
<223> OTHER INFORMATION: D15S209 primer

<400> SEQUENCE: 51
aaacatagtg ctctggaggc                                         20

<210> SEQ ID NO 52
<211> LENGTH: 20
<212> TYPE: DNA
<213> ORGANISM: Artificial Sequence
<220> FEATURE:
<223> OTHER INFORMATION: D15S209 primer
```

```
<400> SEQUENCE: 52
gggctaacaa cagtgtctgc                                          20

<210> SEQ ID NO 53
<211> LENGTH: 20
<212> TYPE: DNA
<213> ORGANISM: Artificial Sequence
<220> FEATURE:
<223> OTHER INFORMATION: D15S1049 primer

<400> SEQUENCE: 53
cactccagcc taaggaacac                                          20

<210> SEQ ID NO 54
<211> LENGTH: 23
<212> TYPE: DNA
<213> ORGANISM: Artificial Sequence
<220> FEATURE:
<223> OTHER INFORMATION: D15S1049 primer

<400> SEQUENCE: 54
tgtcaaagat ggcttttatt acc                                      23

<210> SEQ ID NO 55
<211> LENGTH: 25
<212> TYPE: DNA
<213> ORGANISM: Artificial Sequence
<220> FEATURE:
<223> OTHER INFORMATION: D15S1029 primer

<400> SEQUENCE: 55
aagagtaaaa ctccgtcaca aacac                                    25

<210> SEQ ID NO 56
<211> LENGTH: 24
<212> TYPE: DNA
<213> ORGANISM: Artificial Sequence
<220> FEATURE:
<223> OTHER INFORMATION: D15S1029 primer

<400> SEQUENCE: 56
agatttgagt ctctgcacag taag                                     24

<210> SEQ ID NO 57
<211> LENGTH: 17
<212> TYPE: DNA
<213> ORGANISM: Artificial Sequence
<220> FEATURE:
<223> OTHER INFORMATION: D15S962 primer

<400> SEQUENCE: 57
aattctgctc attgggg                                             17

<210> SEQ ID NO 58
<211> LENGTH: 20
<212> TYPE: DNA
<213> ORGANISM: Artificial Sequence
<220> FEATURE:
<223> OTHER INFORMATION: D15S962 primer

<400> SEQUENCE: 58
ggatattttg gaactgcact                                          20
```

```
<210> SEQ ID NO 59
<211> LENGTH: 24
<212> TYPE: DNA
<213> ORGANISM: Artificial Sequence
<220> FEATURE:
<223> OTHER INFORMATION: D15S998 primer

<400> SEQUENCE: 59
aagcatcaaa gtgtaactca gacc                                    24

<210> SEQ ID NO 60
<211> LENGTH: 20
<212> TYPE: DNA
<213> ORGANISM: Artificial Sequence
<220> FEATURE:
<223> OTHER INFORMATION: D15S998 primer

<400> SEQUENCE: 60
ttggagcctg tgtatgtgtg                                         20

<210> SEQ ID NO 61
<211> LENGTH: 17
<212> TYPE: DNA
<213> ORGANISM: Artificial Sequence
<220> FEATURE:
<223> OTHER INFORMATION: D15S1008 primer

<400> SEQUENCE: 61
ggtgctgcct cctaaca                                            17

<210> SEQ ID NO 62
<211> LENGTH: 17
<212> TYPE: DNA
<213> ORGANISM: Artificial Sequence
<220> FEATURE:
<223> OTHER INFORMATION: D15S1008 primer

<400> SEQUENCE: 62
cgagcccttc tgaaaca                                            17

<210> SEQ ID NO 63
<211> LENGTH: 20
<212> TYPE: DNA
<213> ORGANISM: Artificial Sequence
<220> FEATURE:
<223> OTHER INFORMATION: D15S150 primer

<400> SEQUENCE: 63
ctgtatggcc tcagtctcgg                                         20

<210> SEQ ID NO 64
<211> LENGTH: 20
<212> TYPE: DNA
<213> ORGANISM: Artificial Sequence
<220> FEATURE:
<223> OTHER INFORMATION: D15S150 primer

<400> SEQUENCE: 64
agctctgtgc ggaagtccct                                         20

<210> SEQ ID NO 65
<211> LENGTH: 19
<212> TYPE: DNA
<213> ORGANISM: Artificial Sequence
<220> FEATURE:
<223> OTHER INFORMATION: D4S431 and D4S2366 forward primer
```

<400> SEQUENCE: 65
aggcatacta ggccgtatt                                                 19

<210> SEQ ID NO 66
<211> LENGTH: 17
<212> TYPE: DNA
<213> ORGANISM: Artificial Sequence
<220> FEATURE:
<223> OTHER INFORMATION: D4S431 and D4S2366 reverse primer

<400> SEQUENCE: 66
ttcccatcag cgtcttc                                                   17

<210> SEQ ID NO 67
<211> LENGTH: 20
<212> TYPE: DNA
<213> ORGANISM: Artificial Sequence
<220> FEATURE:
<223> OTHER INFORMATION: D4S2935 forward primer

<400> SEQUENCE: 67
gctcacagaa gtgcccaata                                                20

<210> SEQ ID NO 68
<211> LENGTH: 21
<212> TYPE: DNA
<213> ORGANISM: Artificial Sequence
<220> FEATURE:
<223> OTHER INFORMATION: D4S2935 reverse primer

<400> SEQUENCE: 68
ccctgggtga agtttaatct c                                              21

<210> SEQ ID NO 69
<211> LENGTH: 23
<212> TYPE: DNA
<213> ORGANISM: Artificial Sequence
<220> FEATURE:
<223> OTHER INFORMATION: D4S3007 forward primer

<400> SEQUENCE: 69
atttttgcta cattggtgac ata                                            23

<210> SEQ ID NO 70
<211> LENGTH: 23
<212> TYPE: DNA
<213> ORGANISM: Artificial Sequence
<220> FEATURE:
<223> OTHER INFORMATION: D4S3007 reverse primer

<400> SEQUENCE: 70
cttcaggttc tactagttca tgg                                            23

<210> SEQ ID NO 71
<211> LENGTH: 20
<212> TYPE: DNA
<213> ORGANISM: Artificial Sequence
<220> FEATURE:
<223> OTHER INFORMATION: D4S394 forward primer

<400> SEQUENCE: 71
cccttgagca tcctgacttc                                                20

```
<210> SEQ ID NO 72
<211> LENGTH: 20
<212> TYPE: DNA
<213> ORGANISM: Artificial Sequence
<220> FEATURE:
<223> OTHER INFORMATION: D4S394 reverse primer

<400> SEQUENCE: 72
gagtgagccc ctgtactcca                                          20

<210> SEQ ID NO 73
<211> LENGTH: 20
<212> TYPE: DNA
<213> ORGANISM: Artificial Sequence
<220> FEATURE:
<223> OTHER INFORMATION: D4S1582 forward primer

<400> SEQUENCE: 73
atcagggttc tccacacaaa                                          20

<210> SEQ ID NO 74
<211> LENGTH: 24
<212> TYPE: DNA
<213> ORGANISM: Artificial Sequence
<220> FEATURE:
<223> OTHER INFORMATION: D4S1582 reverse primer

<400> SEQUENCE: 74
ttggttgaaa cttgtggata taaa                                     24

<210> SEQ ID NO 75
<211> LENGTH: 25
<212> TYPE: DNA
<213> ORGANISM: Artificial Sequence
<220> FEATURE:
<223> OTHER INFORMATION: D4S1605 forward primer

<400> SEQUENCE: 75
cattctagta gttattggct tatcc                                    25

<210> SEQ ID NO 76
<211> LENGTH: 25
<212> TYPE: DNA
<213> ORGANISM: Artificial Sequence
<220> FEATURE:
<223> OTHER INFORMATION: D4S1605 reverse primer

<400> SEQUENCE: 76
cagttgcttg atacctatat ttttc                                    25

<210> SEQ ID NO 77
<211> LENGTH: 18
<212> TYPE: DNA
<213> ORGANISM: Artificial Sequence
<220> FEATURE:
<223> OTHER INFORMATION: D4S2949 forward primer

<400> SEQUENCE: 77
ccttacggat aggggcag                                            18

<210> SEQ ID NO 78
<211> LENGTH: 20
<212> TYPE: DNA
<213> ORGANISM: Artificial Sequence
<220> FEATURE:
<223> OTHER INFORMATION: D4S2949 reverse primer
```

```
<400> SEQUENCE: 78
ctaatgtcca ggtctacggc                                              20

<210> SEQ ID NO 79
<211> LENGTH: 20
<212> TYPE: DNA
<213> ORGANISM: Artificial Sequence
<220> FEATURE:
<223> OTHER INFORMATION: D4S403 forward primer

<400> SEQUENCE: 79
aggtggccct gagtaggagt                                              20

<210> SEQ ID NO 80
<211> LENGTH: 20
<212> TYPE: DNA
<213> ORGANISM: Artificial Sequence
<220> FEATURE:
<223> OTHER INFORMATION: D4S403 reverse primer

<400> SEQUENCE: 80
tttgagggaa tgatttgggt                                              20

<210> SEQ ID NO 81
<211> LENGTH: 22
<212> TYPE: DNA
<213> ORGANISM: Artificial Sequence
<220> FEATURE:
<223> OTHER INFORMATION: D4S2423 forward primer

<400> SEQUENCE: 81
aatgcttatc taccaatgag tg                                           22

<210> SEQ ID NO 82
<211> LENGTH: 21
<212> TYPE: DNA
<213> ORGANISM: Artificial Sequence
<220> FEATURE:
<223> OTHER INFORMATION: D4S2423 reverse primer

<400> SEQUENCE: 82
gtggctgggt agtattcatg g                                            21

<210> SEQ ID NO 83
<211> LENGTH: 18
<212> TYPE: DNA
<213> ORGANISM: Artificial Sequence
<220> FEATURE:
<223> OTHER INFORMATION: D4S422 forward primer
<221> NAME/KEY: modified_base
<222> LOCATION: (8)...(8)
<223> OTHER INFORMATION: n = g,a,c or t

<400> SEQUENCE: 83
ggcaagantc cgtctcaa                                                18

<210> SEQ ID NO 84
<211> LENGTH: 23
<212> TYPE: DNA
<213> ORGANISM: Artificial Sequence
<220> FEATURE:
<223> OTHER INFORMATION: D4S422 reverse primer

<400> SEQUENCE: 84
tgaagtaaaa tttgggagat tgt                                          23
```

```
<210> SEQ ID NO 85
<211> LENGTH: 20
<212> TYPE: DNA
<213> ORGANISM: Artificial Sequence
<220> FEATURE:
<223> OTHER INFORMATION: D4S397 forward primer

<400> SEQUENCE: 85
agggaggtca tcagttcatt                                              20

<210> SEQ ID NO 86
<211> LENGTH: 20
<212> TYPE: DNA
<213> ORGANISM: Artificial Sequence
<220> FEATURE:
<223> OTHER INFORMATION: D4S397 reverse primer

<400> SEQUENCE: 86
tgttgcaaac tttgcttttc                                              20

<210> SEQ ID NO 87
<211> LENGTH: 18
<212> TYPE: DNA
<213> ORGANISM: Artificial Sequence
<220> FEATURE:
<223> OTHER INFORMATION: D4S420 forward primer

<400> SEQUENCE: 87
ttctttgatt cttcgggg                                                18

<210> SEQ ID NO 88
<211> LENGTH: 20
<212> TYPE: DNA
<213> ORGANISM: Artificial Sequence
<220> FEATURE:
<223> OTHER INFORMATION: D4S420 reverse primer

<400> SEQUENCE: 88
tttctcagca acattcctct                                              20

<210> SEQ ID NO 89
<211> LENGTH: 20
<212> TYPE: DNA
<213> ORGANISM: Artificial Sequence
<220> FEATURE:
<223> OTHER INFORMATION: D4S1644 forward primer

<400> SEQUENCE: 89
taacattgac cgctcctctc                                              20

<210> SEQ ID NO 90
<211> LENGTH: 20
<212> TYPE: DNA
<213> ORGANISM: Artificial Sequence
<220> FEATURE:
<223> OTHER INFORMATION: D4S1644 reverse primer

<400> SEQUENCE: 90
catccttcct ggtccctagt                                              20

<210> SEQ ID NO 91
<211> LENGTH: 20
<212> TYPE: DNA
<213> ORGANISM: Artificial Sequence
<220> FEATURE:
<223> OTHER INFORMATION: UT2147 forward primer
```

```
<400> SEQUENCE: 91
taaaacttct gaatgaaaag                                          20

<210> SEQ ID NO 92
<211> LENGTH: 18
<212> TYPE: DNA
<213> ORGANISM: Artificial Sequence
<220> FEATURE:
<223> OTHER INFORMATION: UT2147 reverse primer

<400> SEQUENCE: 92
gtagggagga atagttag                                            18

<210> SEQ ID NO 93
<211> LENGTH: 20
<212> TYPE: DNA
<213> ORGANISM: Artificial Sequence
<220> FEATURE:
<223> OTHER INFORMATION: D4S1565 forward primer

<400> SEQUENCE: 93
tgcaaactgt cactcaaaag                                          20

<210> SEQ ID NO 94
<211> LENGTH: 16
<212> TYPE: DNA
<213> ORGANISM: Artificial Sequence
<220> FEATURE:
<223> OTHER INFORMATION: D4S1565 reverse primer

<400> SEQUENCE: 94
gccaaggctg atcctc                                              16

<210> SEQ ID NO 95
<211> LENGTH: 22
<212> TYPE: DNA
<213> ORGANISM: Artificial Sequence
<220> FEATURE:
<223> OTHER INFORMATION: D4S424 forward primer

<400> SEQUENCE: 95
gcgctcttgg tatatggtac ag                                       22

<210> SEQ ID NO 96
<211> LENGTH: 17
<212> TYPE: DNA
<213> ORGANISM: Artificial Sequence
<220> FEATURE:
<223> OTHER INFORMATION: D4S424 reverse primer

<400> SEQUENCE: 96
tgtgggcaac gtcactc                                             17

<210> SEQ ID NO 97
<211> LENGTH: 20
<212> TYPE: DNA
<213> ORGANISM: Artificial Sequence
<220> FEATURE:
<223> OTHER INFORMATION: D4S1625 forward primer

<400> SEQUENCE: 97
gactccaaat cacatgagcc                                          20
```

<210> SEQ ID NO 98
<211> LENGTH: 20
<212> TYPE: DNA
<213> ORGANISM: Artificial Sequence
<220> FEATURE:
<223> OTHER INFORMATION: D4S1625 reverse primer

<400> SEQUENCE: 98

```
    gtctctgcat ttgctggttt                                              20
```

<210> SEQ ID NO 99
<211> LENGTH: 23
<212> TYPE: DNA
<213> ORGANISM: Artificial Sequence
<220> FEATURE:
<223> OTHER INFORMATION: GATA145E01 forward primer

<400> SEQUENCE: 99

```
    ctcaagagaa atagaaccaa taa                                          23
```

<210> SEQ ID NO 100
<211> LENGTH: 20
<212> TYPE: DNA
<213> ORGANISM: Artificial Sequence
<220> FEATURE:
<223> OTHER INFORMATION: GATA145E01 reverse primer

<400> SEQUENCE: 100

```
    taagacggaa accaaatgga                                              20
```

<210> SEQ ID NO 101
<211> LENGTH: 20
<212> TYPE: DNA
<213> ORGANISM: Artificial Sequence
<220> FEATURE:
<223> OTHER INFORMATION: D4S432 forward primer

<400> SEQUENCE: 101

```
    actctgaagg ctgagatggg                                              20
```

<210> SEQ ID NO 102
<211> LENGTH: 17
<212> TYPE: DNA
<213> ORGANISM: Artificial Sequence
<220> FEATURE:
<223> OTHER INFORMATION: D4S432 reverse primer

<400> SEQUENCE: 102

```
    ctgaaccgca gatcccc                                                 17
```

<210> SEQ ID NO 103
<211> LENGTH: 20
<212> TYPE: DNA
<213> ORGANISM: Artificial Sequence
<220> FEATURE:
<223> OTHER INFORMATION: D4S2925 forward primer

<400> SEQUENCE: 103

```
    tcagaaaccc ctacaggaaa                                              20
```

<210> SEQ ID NO 104
<211> LENGTH: 20
<212> TYPE: DNA
<213> ORGANISM: Artificial Sequence
<220> FEATURE:
<223> OTHER INFORMATION: D4S2925 reverse primer

```
<400> SEQUENCE: 104
tttgatgagt tattcggagg                                                    20

<210> SEQ ID NO 105
<211> LENGTH: 21
<212> TYPE: DNA
<213> ORGANISM: Artificial Sequence
<220> FEATURE:
<223> OTHER INFORMATION: D4S3023 forward primer

<400> SEQUENCE: 105
acctcactgg aaactaaatg g                                                  21

<210> SEQ ID NO 106
<211> LENGTH: 16
<212> TYPE: DNA
<213> ORGANISM: Artificial Sequence
<220> FEATURE:
<223> OTHER INFORMATION: D4S3023 reverse primer

<400> SEQUENCE: 106
tgaacagcag cggtct                                                        16

<210> SEQ ID NO 107
<211> LENGTH: 17
<212> TYPE: DNA
<213> ORGANISM: Artificial Sequence
<220> FEATURE:
<223> OTHER INFORMATION: D4S2923 forward primer

<400> SEQUENCE: 107
gggcatcatg tctgcaa                                                       17

<210> SEQ ID NO 108
<211> LENGTH: 18
<212> TYPE: DNA
<213> ORGANISM: Artificial Sequence
<220> FEATURE:
<223> OTHER INFORMATION: D4S2923 reverse primer

<400> SEQUENCE: 108
aggttccctg aatgttcg                                                      18

<210> SEQ ID NO 109
<211> LENGTH: 16
<212> TYPE: DNA
<213> ORGANISM: Artificial Sequence
<220> FEATURE:
<223> OTHER INFORMATION: D4S2983 forward primer

<400> SEQUENCE: 109
tgtccagttg gcaggg                                                        16

<210> SEQ ID NO 110
<211> LENGTH: 16
<212> TYPE: DNA
<213> ORGANISM: Artificial Sequence
<220> FEATURE:
<223> OTHER INFORMATION: D4S2983 reverse primer

<400> SEQUENCE: 110
ggtcgcattc attcgc                                                        16
```

```
<210> SEQ ID NO 111
<211> LENGTH: 19
<212> TYPE: DNA
<213> ORGANISM: Artificial Sequence
<220> FEATURE:
<223> OTHER INFORMATION: D4S3009 forward primer

<400> SEQUENCE: 111
atggcctgtg aatcaaccc                                              19

<210> SEQ ID NO 112
<211> LENGTH: 19
<212> TYPE: DNA
<213> ORGANISM: Artificial Sequence
<220> FEATURE:
<223> OTHER INFORMATION: D4S3009 reverse primer

<400> SEQUENCE: 112
aatcctttga agacggccc                                              19

<210> SEQ ID NO 113
<211> LENGTH: 19
<212> TYPE: DNA
<213> ORGANISM: Artificial Sequence
<220> FEATURE:
<223> OTHER INFORMATION: D4S2928 forward primer

<400> SEQUENCE: 113
atagacgtgt tcctggtgg                                              19

<210> SEQ ID NO 114
<211> LENGTH: 20
<212> TYPE: DNA
<213> ORGANISM: Artificial Sequence
<220> FEATURE:
<223> OTHER INFORMATION: D4S2928 reverse primer

<400> SEQUENCE: 114
ctcaggctat ttatggggtg                                             20

<210> SEQ ID NO 115
<211> LENGTH: 25
<212> TYPE: DNA
<213> ORGANISM: Artificial Sequence
<220> FEATURE:
<223> OTHER INFORMATION: D4S1599 forward primer

<400> SEQUENCE: 115
ccttaaaagt atccagtaaa gcaca                                       25

<210> SEQ ID NO 116
<211> LENGTH: 20
<212> TYPE: DNA
<213> ORGANISM: Artificial Sequence
<220> FEATURE:
<223> OTHER INFORMATION: D4S1599 reverse primer

<400> SEQUENCE: 116
caaggttgtc ctgtgtctgc                                             20

<210> SEQ ID NO 117
<211> LENGTH: 25
<212> TYPE: DNA
<213> ORGANISM: Artificial Sequence
<220> FEATURE:
<223> OTHER INFORMATION: D4S2906 forward primer
```

```
<400> SEQUENCE: 117
cagtctagat tcaaaggaat tagac                                    25

<210> SEQ ID NO 118
<211> LENGTH: 20
<212> TYPE: DNA
<213> ORGANISM: Artificial Sequence
<220> FEATURE:
<223> OTHER INFORMATION: D4S2906 reverse primer

<400> SEQUENCE: 118
aattagagat gcccgtgaaa                                          20

<210> SEQ ID NO 119
<211> LENGTH: 17
<212> TYPE: DNA
<213> ORGANISM: Artificial Sequence
<220> FEATURE:
<223> OTHER INFORMATION: D4S3036 forward primer

<400> SEQUENCE: 119
agcttcttgc tgtgtcc                                             17

<210> SEQ ID NO 120
<211> LENGTH: 16
<212> TYPE: DNA
<213> ORGANISM: Artificial Sequence
<220> FEATURE:
<223> OTHER INFORMATION: D4S3036 reverse primer

<400> SEQUENCE: 120
aagggtgggg ctctat                                              16

<210> SEQ ID NO 121
<211> LENGTH: 18
<212> TYPE: DNA
<213> ORGANISM: Artificial Sequence
<220> FEATURE:
<223> OTHER INFORMATION: D4S2944 forward primer

<400> SEQUENCE: 121
agattctggc ctccttgc                                            18

<210> SEQ ID NO 122
<211> LENGTH: 17
<212> TYPE: DNA
<213> ORGANISM: Artificial Sequence
<220> FEATURE:
<223> OTHER INFORMATION: D4S2944 reverse primer

<400> SEQUENCE: 122
cctggtgaag tggtggg                                             17

<210> SEQ ID NO 123
<211> LENGTH: 19
<212> TYPE: DNA
<213> ORGANISM: Artificial Sequence
<220> FEATURE:
<223> OTHER INFORMATION: D4S2942 forward primer

<400> SEQUENCE: 123
caaatgccca tcaatcaac                                           19
```

```
<210> SEQ ID NO 124
<211> LENGTH: 18
<212> TYPE: DNA
<213> ORGANISM: Artificial Sequence
<220> FEATURE:
<223> OTHER INFORMATION: D4S2942 reverse primer

<400> SEQUENCE: 124
gggtccagtc tcatccac                                           18

<210> SEQ ID NO 125
<211> LENGTH: 19
<212> TYPE: DNA
<213> ORGANISM: Artificial Sequence
<220> FEATURE:
<223> OTHER INFORMATION: D4S1602 forward primer

<400> SEQUENCE: 125
ccagatgggt tccaaatga                                          19

<210> SEQ ID NO 126
<211> LENGTH: 22
<212> TYPE: DNA
<213> ORGANISM: Artificial Sequence
<220> FEATURE:
<223> OTHER INFORMATION: D4S1602 reverse primer

<400> SEQUENCE: 126
tgtggactga gtagagagtg cc                                      22

<210> SEQ ID NO 127
<211> LENGTH: 18
<212> TYPE: DNA
<213> ORGANISM: Artificial Sequence
<220> FEATURE:
<223> OTHER INFORMATION: D4S2984 forward primer

<400> SEQUENCE: 127
ccccaaagga atcagatg                                           18

<210> SEQ ID NO 128
<211> LENGTH: 22
<212> TYPE: DNA
<213> ORGANISM: Artificial Sequence
<220> FEATURE:
<223> OTHER INFORMATION: D4S2984 reverse primer

<400> SEQUENCE: 128
gatcttgaaa ttttcccatt tt                                      22

<210> SEQ ID NO 129
<211> LENGTH: 16
<212> TYPE: DNA
<213> ORGANISM: Artificial Sequence
<220> FEATURE:
<223> OTHER INFORMATION: D4S1564 forward primer

<400> SEQUENCE: 129
agcccaggag gtgaag                                             16

<210> SEQ ID NO 130
<211> LENGTH: 22
<212> TYPE: DNA
<213> ORGANISM: Artificial Sequence
<220> FEATURE:
<223> OTHER INFORMATION: D4S1564 reverse primer
```

<400> SEQUENCE: 130
gagatttcta ggaaacattg ag 22

<210> SEQ ID NO 131
<211> LENGTH: 24
<212> TYPE: DNA
<213> ORGANISM: Artificial Sequence
<220> FEATURE:
<223> OTHER INFORMATION: D4S1611 forward primer

<400> SEQUENCE: 131
agagtagttt ccatctttgt tttc 24

<210> SEQ ID NO 132
<211> LENGTH: 16
<212> TYPE: DNA
<213> ORGANISM: Artificial Sequence
<220> FEATURE:
<223> OTHER INFORMATION: D4S1611 reverse primer

<400> SEQUENCE: 132
gggcaaggct catcac 16

<210> SEQ ID NO 133
<211> LENGTH: 23
<212> TYPE: DNA
<213> ORGANISM: Artificial Sequence
<220> FEATURE:
<223> OTHER INFORMATION: D4S1573 forward primer

<400> SEQUENCE: 133
acatggagaa tcttttagta gca 23

<210> SEQ ID NO 134
<211> LENGTH: 22
<212> TYPE: DNA
<213> ORGANISM: Artificial Sequence
<220> FEATURE:
<223> OTHER INFORMATION: D4S1573 reverse primer

<400> SEQUENCE: 134
cttttgagat accctatca gt 22

<210> SEQ ID NO 135
<211> LENGTH: 16
<212> TYPE: DNA
<213> ORGANISM: Artificial Sequence
<220> FEATURE:
<223> OTHER INFORMATION: D4S427 forward primer

<400> SEQUENCE: 135
ggacctcctt gcttcg 16

<210> SEQ ID NO 136
<211> LENGTH: 17
<212> TYPE: DNA
<213> ORGANISM: Artificial Sequence
<220> FEATURE:
<223> OTHER INFORMATION: D4S427 reverse primer

<400> SEQUENCE: 136
ccccttaggt tgcttgt 17

```
<210> SEQ ID NO 137
<211> LENGTH: 21
<212> TYPE: DNA
<213> ORGANISM: Artificial Sequence
<220> FEATURE:
<223> OTHER INFORMATION: GATA30B11 forward primer

<400> SEQUENCE: 137
tttagttgaa tggctgagtg g                                          21

<210> SEQ ID NO 138
<211> LENGTH: 20
<212> TYPE: DNA
<213> ORGANISM: Artificial Sequence
<220> FEATURE:
<223> OTHER INFORMATION: GATA30B11 reverse primer

<400> SEQUENCE: 138
tgagccaatt ccctaataa                                             20

<210> SEQ ID NO 139
<211> LENGTH: 21
<212> TYPE: DNA
<213> ORGANISM: Artificial Sequence
<220> FEATURE:
<223> OTHER INFORMATION: UT7161 forward primer

<400> SEQUENCE: 139
ccacaaagac agaatcaata g                                          21

<210> SEQ ID NO 140
<211> LENGTH: 20
<212> TYPE: DNA
<213> ORGANISM: Artificial Sequence
<220> FEATURE:
<223> OTHER INFORMATION: UT161 reverse primer

<400> SEQUENCE: 140
tctcaacctc cataactgtg                                            20

<210> SEQ ID NO 141
<211> LENGTH: 20
<212> TYPE: DNA
<213> ORGANISM: Artificial Sequence
<220> FEATURE:
<223> OTHER INFORMATION: ATA26F08 forward primer

<400> SEQUENCE: 141
tttgatttcc tgcagttggt                                            20

<210> SEQ ID NO 142
<211> LENGTH: 20
<212> TYPE: DNA
<213> ORGANISM: Artificial Sequence
<220> FEATURE:
<223> OTHER INFORMATION: ATA26F08 reverse primer

<400> SEQUENCE: 142
tcaacacaaa accaatgtgg                                            20

<210> SEQ ID NO 143
<211> LENGTH: 23
<212> TYPE: DNA
<213> ORGANISM: Artificial Sequence
<220> FEATURE:
<223> OTHER INFORMATION: D4S2985 forward primer
```

```
<400> SEQUENCE: 143
ttacactgaa gaatgtgaga gcc                                        23

<210> SEQ ID NO 144
<211> LENGTH: 20
<212> TYPE: DNA
<213> ORGANISM: Artificial Sequence
<220> FEATURE:
<223> OTHER INFORMATION: D4S2985 reverse primer

<400> SEQUENCE: 144
ggccttggaa ctactgatgg                                            20

<210> SEQ ID NO 145
<211> LENGTH: 20
<212> TYPE: DNA
<213> ORGANISM: Artificial Sequence
<220> FEATURE:
<223> OTHER INFORMATION: D4S1615 forward primer

<400> SEQUENCE: 145
ccttgggtca gccacatatc                                            20

<210> SEQ ID NO 146
<211> LENGTH: 22
<212> TYPE: DNA
<213> ORGANISM: Artificial Sequence
<220> FEATURE:
<223> OTHER INFORMATION: D4S1615 reverse primer

<400> SEQUENCE: 146
cactcagaac agaaacttgg gt                                         22

<210> SEQ ID NO 147
<211> LENGTH: 20
<212> TYPE: DNA
<213> ORGANISM: Artificial Sequence
<220> FEATURE:
<223> OTHER INFORMATION: ATA26B08 forward primer

<400> SEQUENCE: 147
actggtatgt cctaacccccc                                           20

<210> SEQ ID NO 148
<211> LENGTH: 20
<212> TYPE: DNA
<213> ORGANISM: Artificial Sequence
<220> FEATURE:
<223> OTHER INFORMATION: ATA26B08 reverse primer

<400> SEQUENCE: 148
gatctgcagt tggattctgg                                            20

<210> SEQ ID NO 149
<211> LENGTH: 19
<212> TYPE: DNA
<213> ORGANISM: Artificial Sequence
<220> FEATURE:
<223> OTHER INFORMATION: UT6123 forward primer

<400> SEQUENCE: 149
gctgcacctt agactagat                                             19
```

```
<210> SEQ ID NO 150
<211> LENGTH: 19
<212> TYPE: DNA
<213> ORGANISM: Artificial Sequence
<220> FEATURE:
<223> OTHER INFORMATION: UT6123 reverse primer

<400> SEQUENCE: 150
ttagtagctt ctcagcagc                                             19

<210> SEQ ID NO 151
<211> LENGTH: 21
<212> TYPE: DNA
<213> ORGANISM: Artificial Sequence
<220> FEATURE:
<223> OTHER INFORMATION: UT723 forward primer

<400> SEQUENCE: 151
cagacataaa tgaaagaaaa g                                          21

<210> SEQ ID NO 152
<211> LENGTH: 22
<212> TYPE: DNA
<213> ORGANISM: Artificial Sequence
<220> FEATURE:
<223> OTHER INFORMATION: UT723 reverse primer

<400> SEQUENCE: 152
ggcagcaaac tatggtatgt aa                                         22

<210> SEQ ID NO 153
<211> LENGTH: 20
<212> TYPE: DNA
<213> ORGANISM: Artificial Sequence
<220> FEATURE:
<223> OTHER INFORMATION: UT1376 forward primer

<400> SEQUENCE: 153
aagttaatcc atgtgccgtg                                            20

<210> SEQ ID NO 154
<211> LENGTH: 21
<212> TYPE: DNA
<213> ORGANISM: Artificial Sequence
<220> FEATURE:
<223> OTHER INFORMATION: UT1376 reverse primer

<400> SEQUENCE: 154
cttctttctc tttttttccct g                                         21

<210> SEQ ID NO 155
<211> LENGTH: 16
<212> TYPE: DNA
<213> ORGANISM: Artificial Sequence
<220> FEATURE:
<223> OTHER INFORMATION: D4S429 forward primer

<400> SEQUENCE: 155
ggtgatccac ctgcct                                                16

<210> SEQ ID NO 156
<211> LENGTH: 18
<212> TYPE: DNA
<213> ORGANISM: Artificial Sequence
<220> FEATURE:
<223> OTHER INFORMATION: D4S429 reverse primer
```

```
<400> SEQUENCE: 156
aagccactga ccttcact                                              18

<210> SEQ ID NO 157
<211> LENGTH: 25
<212> TYPE: DNA
<213> ORGANISM: Artificial Sequence
<220> FEATURE:
<223> OTHER INFORMATION: D4S3039 forward primer

<400> SEQUENCE: 157
gacagcctat tgtagtaact tgtgg                                      25

<210> SEQ ID NO 158
<211> LENGTH: 20
<212> TYPE: DNA
<213> ORGANISM: Artificial Sequence
<220> FEATURE:
<223> OTHER INFORMATION: D4S3039 reverse primer

<400> SEQUENCE: 158
tagtcagggt gctctagggg                                            20

<210> SEQ ID NO 159
<211> LENGTH: 24
<212> TYPE: DNA
<213> ORGANISM: Artificial Sequence
<220> FEATURE:
<223> OTHER INFORMATION: D4S1575 forward primer

<400> SEQUENCE: 159
atgggtactt tttgaatcac atcc                                       24

<210> SEQ ID NO 160
<211> LENGTH: 19
<212> TYPE: DNA
<213> ORGANISM: Artificial Sequence
<220> FEATURE:
<223> OTHER INFORMATION: D4S1575 reverse primer

<400> SEQUENCE: 160
acactccagc ctgggtgac                                             19

<210> SEQ ID NO 161
<211> LENGTH: 21
<212> TYPE: DNA
<213> ORGANISM: Artificial Sequence
<220> FEATURE:
<223> OTHER INFORMATION: D4S2959 forward primer

<400> SEQUENCE: 161
agcttccatg gtcattagag t                                          21

<210> SEQ ID NO 162
<211> LENGTH: 22
<212> TYPE: DNA
<213> ORGANISM: Artificial Sequence
<220> FEATURE:
<223> OTHER INFORMATION: D4S2959 reverse primer

<400> SEQUENCE: 162
taagggtcct ccaaagaaca ga                                         22
```

```
<210> SEQ ID NO 163
<211> LENGTH: 23
<212> TYPE: DNA
<213> ORGANISM: Artificial Sequence
<220> FEATURE:
<223> OTHER INFORMATION: D4S1576 forward primer
<221> NAME/KEY: modified_base
<222> LOCATION: (6)...(6)
<223> OTHER INFORMATION: n = g,a,c or t

<400> SEQUENCE: 163
attgtncata tatcatcacc tgg                                      23

<210> SEQ ID NO 164
<211> LENGTH: 23
<212> TYPE: DNA
<213> ORGANISM: Artificial Sequence
<220> FEATURE:
<223> OTHER INFORMATION: D4S1576 reverse primer

<400> SEQUENCE: 164
acagcataaa ctaaaatttg ggg                                      23

<210> SEQ ID NO 165
<211> LENGTH: 18
<212> TYPE: DNA
<213> ORGANISM: Artificial Sequence
<220> FEATURE:
<223> OTHER INFORMATION: D4S2972 forward primer
<221> NAME/KEY: modified_base
<222> LOCATION: (12)...(12)
<223> OTHER INFORMATION: n = g,a,c or t

<400> SEQUENCE: 165
agctactcag gnaggctg                                            18

<210> SEQ ID NO 166
<211> LENGTH: 25
<212> TYPE: DNA
<213> ORGANISM: Artificial Sequence
<220> FEATURE:
<223> OTHER INFORMATION: D4S2972 reverse primer

<400> SEQUENCE: 166
tttttaatat ccaacctcac ttgtg                                    25

<210> SEQ ID NO 167
<211> LENGTH: 16
<212> TYPE: DNA
<213> ORGANISM: Artificial Sequence
<220> FEATURE:
<223> OTHER INFORMATION: D4S1579 forward primer

<400> SEQUENCE: 167
cccccacctt cctgac                                              16

<210> SEQ ID NO 168
<211> LENGTH: 16
<212> TYPE: DNA
<213> ORGANISM: Artificial Sequence
<220> FEATURE:
<223> OTHER INFORMATION: D4S1579 reverse primer

<400> SEQUENCE: 168
ctggagcatc cgtgtg                                              16
```

```
<210> SEQ ID NO 169
<211> LENGTH: 19
<212> TYPE: DNA
<213> ORGANISM: Artificial Sequence
<220> FEATURE:
<223> OTHER INFORMATION: UT1264 forward primer

<400> SEQUENCE: 169
tcgatctgca gttgccta                                          19

<210> SEQ ID NO 170
<211> LENGTH: 20
<212> TYPE: DNA
<213> ORGANISM: Artificial Sequence
<220> FEATURE:
<223> OTHER INFORMATION: UT1264 reverse primer

<400> SEQUENCE: 170
tgtacccatt aagcagcctg                                        20

<210> SEQ ID NO 171
<211> LENGTH: 18
<212> TYPE: DNA
<213> ORGANISM: Artificial Sequence
<220> FEATURE:
<223> OTHER INFORMATION: D4S2939 forward primer

<400> SEQUENCE: 171
tttcccacct ggccttat                                          18

<210> SEQ ID NO 172
<211> LENGTH: 20
<212> TYPE: DNA
<213> ORGANISM: Artificial Sequence
<220> FEATURE:
<223> OTHER INFORMATION: D4S2939 reverse primer

<400> SEQUENCE: 172
ctcttgaagc cctgaagttt                                        20

<210> SEQ ID NO 173
<211> LENGTH: 23
<212> TYPE: DNA
<213> ORGANISM: Artificial Sequence
<220> FEATURE:
<223> OTHER INFORMATION: D4S2965 forward primer

<400> SEQUENCE: 173
tttacagttt tcaaaatggg ttc                                    23

<210> SEQ ID NO 174
<211> LENGTH: 19
<212> TYPE: DNA
<213> ORGANISM: Artificial Sequence
<220> FEATURE:
<223> OTHER INFORMATION: D4S2965 reverse primer

<400> SEQUENCE: 174
ggttcttgac cctagctcc                                         19

<210> SEQ ID NO 175
<211> LENGTH: 18
<212> TYPE: DNA
<213> ORGANISM: Artificial Sequence
<220> FEATURE:
<223> OTHER INFORMATION: GATA135E06 forward primer
```

```
<400> SEQUENCE: 175
ggccaacaga gcaggatc                                              18

<210> SEQ ID NO 176
<211> LENGTH: 20
<212> TYPE: DNA
<213> ORGANISM: Artificial Sequence
<220> FEATURE:
<223> OTHER INFORMATION: GATA135E06 reverse primer

<400> SEQUENCE: 176
gccaagagag tgagactcca                                            20

<210> SEQ ID NO 177
<211> LENGTH: 25
<212> TYPE: DNA
<213> ORGANISM: Artificial Sequence
<220> FEATURE:
<223> OTHER INFORMATION: D4S2981 forward primer

<400> SEQUENCE: 177
ggttatttaa ttttagtaac gcatc                                      25

<210> SEQ ID NO 178
<211> LENGTH: 19
<212> TYPE: DNA
<213> ORGANISM: Artificial Sequence
<220> FEATURE:
<223> OTHER INFORMATION: D4S2981 reverse primer

<400> SEQUENCE: 178
gaacagaagt gctggagac                                             19

<210> SEQ ID NO 179
<211> LENGTH: 16
<212> TYPE: DNA
<213> ORGANISM: Artificial Sequence
<220> FEATURE:
<223> OTHER INFORMATION: D4S1604 forward primer

<400> SEQUENCE: 179
tcgtgcccag ccaagt                                                16

<210> SEQ ID NO 180
<211> LENGTH: 20
<212> TYPE: DNA
<213> ORGANISM: Artificial Sequence
<220> FEATURE:
<223> OTHER INFORMATION: D4S1604 reverse primer

<400> SEQUENCE: 180
ttgctcacag gattgcttct                                            20

<210> SEQ ID NO 181
<211> LENGTH: 25
<212> TYPE: DNA
<213> ORGANISM: Artificial Sequence
<220> FEATURE:
<223> OTHER INFORMATION: D4S1561 forward primer

<400> SEQUENCE: 181
attttcatgc attcgttaga atttt                                      25
```

```
<210> SEQ ID NO 182
<211> LENGTH: 20
<212> TYPE: DNA
<213> ORGANISM: Artificial Sequence
<220> FEATURE:
<223> OTHER INFORMATION: D4S1561 reverse primer

<400> SEQUENCE: 182
tctaggtgat ggtgatgctg                                          20

<210> SEQ ID NO 183
<211> LENGTH: 18
<212> TYPE: DNA
<213> ORGANISM: Artificial Sequence
<220> FEATURE:
<223> OTHER INFORMATION: D4S1586 forward primer

<400> SEQUENCE: 183
gcatgtacca ttgccagg                                            18

<210> SEQ ID NO 184
<211> LENGTH: 19
<212> TYPE: DNA
<213> ORGANISM: Artificial Sequence
<220> FEATURE:
<223> OTHER INFORMATION: D4S1586 reverse primer

<400> SEQUENCE: 184
cccagagtgc tgatgtgtg                                           19

<210> SEQ ID NO 185
<211> LENGTH: 17
<212> TYPE: DNA
<213> ORGANISM: Artificial Sequence
<220> FEATURE:
<223> OTHER INFORMATION: D4S1549 forward primer

<400> SEQUENCE: 185
aaagttccaa tctcccc                                             17

<210> SEQ ID NO 186
<211> LENGTH: 19
<212> TYPE: DNA
<213> ORGANISM: Artificial Sequence
<220> FEATURE:
<223> OTHER INFORMATION: D4S1549 reverse primer

<400> SEQUENCE: 186
tcttatgctg caatcactg                                           19

<210> SEQ ID NO 187
<211> LENGTH: 20
<212> TYPE: DNA
<213> ORGANISM: Artificial Sequence
<220> FEATURE:
<223> OTHER INFORMATION: D4S1548 forward primer

<400> SEQUENCE: 187
tgccataaac aaggtgaaac                                          20

<210> SEQ ID NO 188
<211> LENGTH: 20
<212> TYPE: DNA
<213> ORGANISM: Artificial Sequence
<220> FEATURE:
<223> OTHER INFORMATION: D4S1548 reverse primer
```

-continued

```
<400> SEQUENCE: 188
ttacccaact gctacaccat                                              20

<210> SEQ ID NO 189
<211> LENGTH: 23
<212> TYPE: DNA
<213> ORGANISM: Artificial Sequence
<220> FEATURE:
<223> OTHER INFORMATION: GATA72A08 forward primer

<400> SEQUENCE: 189
ttcaatactc ctgtatcaca aag                                          23

<210> SEQ ID NO 190
<211> LENGTH: 22
<212> TYPE: DNA
<213> ORGANISM: Artificial Sequence
<220> FEATURE:
<223> OTHER INFORMATION: GATA72A08 reverse primer

<400> SEQUENCE: 190
tgagacacaa tctgagctat gc                                           22

<210> SEQ ID NO 191
<211> LENGTH: 20
<212> TYPE: DNA
<213> ORGANISM: Artificial Sequence
<220> FEATURE:
<223> OTHER INFORMATION: GATA8A05 forward primer

<400> SEQUENCE: 191
tggttctgct ttttctctcc                                              20

<210> SEQ ID NO 192
<211> LENGTH: 24
<212> TYPE: DNA
<213> ORGANISM: Artificial Sequence
<220> FEATURE:
<223> OTHER INFORMATION: GATA8A05 reverse primer

<400> SEQUENCE: 192
tttaacagac aaatgacaaa tctg                                         24

<210> SEQ ID NO 193
<211> LENGTH: 25
<212> TYPE: DNA
<213> ORGANISM: Artificial Sequence
<220> FEATURE:
<223> OTHER INFORMATION: D6S1713 forward primer

<400> SEQUENCE: 193
aatcactgtt acccataggg ttatc                                        25

<210> SEQ ID NO 194
<211> LENGTH: 18
<212> TYPE: DNA
<213> ORGANISM: Artificial Sequence
<220> FEATURE:
<223> OTHER INFORMATION: D6S1713 reverse primer

<400> SEQUENCE: 194
aggccaagac ctctgtgc                                                18
```

```
<210> SEQ ID NO 195
<211> LENGTH: 20
<212> TYPE: DNA
<213> ORGANISM: Artificial Sequence
<220> FEATURE:
<223> OTHER INFORMATION: D6S1617 forward primer

<400> SEQUENCE: 195
tgcaaaacag gcacacatac                                                  20

<210> SEQ ID NO 196
<211> LENGTH: 25
<212> TYPE: DNA
<213> ORGANISM: Artificial Sequence
<220> FEATURE:
<223> OTHER INFORMATION: D6S1617 reverse primer

<400> SEQUENCE: 196
ttaatcaatt ttctgcaaag ataaa                                            25

<210> SEQ ID NO 197
<211> LENGTH: 20
<212> TYPE: DNA
<213> ORGANISM: Artificial Sequence
<220> FEATURE:
<223> OTHER INFORMATION: D6S1668 forward primer

<400> SEQUENCE: 197
gtatagccaa ctgcttccaa                                                  20

<210> SEQ ID NO 198
<211> LENGTH: 20
<212> TYPE: DNA
<213> ORGANISM: Artificial Sequence
<220> FEATURE:
<223> OTHER INFORMATION: D6S1668 reverse primer
<221> NAME/KEY: modified_base
<222> LOCATION: (5)...(5)
<223> OTHER INFORMATION: n = g,a,c or t

<400> SEQUENCE: 198
gggtnccatt tattgagatt                                                  20

<210> SEQ ID NO 199
<211> LENGTH: 18
<212> TYPE: DNA
<213> ORGANISM: Artificial Sequence
<220> FEATURE:
<223> OTHER INFORMATION: D6S1591 forward primer

<400> SEQUENCE: 199
tgtttcagca gcataggg                                                    18

<210> SEQ ID NO 200
<211> LENGTH: 20
<212> TYPE: DNA
<213> ORGANISM: Artificial Sequence
<220> FEATURE:
<223> OTHER INFORMATION: D6S1591 reverse primer

<400> SEQUENCE: 200
agagcctgtt tggtgtcatc                                                  20
```

```
<210> SEQ ID NO 201
<211> LENGTH: 16
<212> TYPE: DNA
<213> ORGANISM: Artificial Sequence
<220> FEATURE:
<223> OTHER INFORMATION: D6S1677 forward primer

<400> SEQUENCE: 201
gtttccaagg gctggg                                              16

<210> SEQ ID NO 202
<211> LENGTH: 24
<212> TYPE: DNA
<213> ORGANISM: Artificial Sequence
<220> FEATURE:
<223> OTHER INFORMATION: D6S1677 reverse primer

<400> SEQUENCE: 202
gaaatcaaaa taacacatcc tctg                                     24

<210> SEQ ID NO 203
<211> LENGTH: 20
<212> TYPE: DNA
<213> ORGANISM: Artificial Sequence
<220> FEATURE:
<223> OTHER INFORMATION: D6S1685 forward primer

<400> SEQUENCE: 203
tacactaatg gctctcctgg                                          20

<210> SEQ ID NO 204
<211> LENGTH: 20
<212> TYPE: DNA
<213> ORGANISM: Artificial Sequence
<220> FEATURE:
<223> OTHER INFORMATION: D6S1685 reverse primer

<400> SEQUENCE: 204
gccagatttc tctgctgtag                                          20

<210> SEQ ID NO 205
<211> LENGTH: 19
<212> TYPE: DNA
<213> ORGANISM: Artificial Sequence
<220> FEATURE:
<223> OTHER INFORMATION: D6S1574 forward primer

<400> SEQUENCE: 205
aagaacttcc caaaccaat                                           19

<210> SEQ ID NO 206
<211> LENGTH: 18
<212> TYPE: DNA
<213> ORGANISM: Artificial Sequence
<220> FEATURE:
<223> OTHER INFORMATION: D6S1574 reverse primer

<400> SEQUENCE: 206
aaccatccag gacatcaa                                            18

<210> SEQ ID NO 207
<211> LENGTH: 17
<212> TYPE: DNA
<213> ORGANISM: Artificial Sequence
<220> FEATURE:
<223> OTHER INFORMATION: D6S1598 forward primer
```

```
<400> SEQUENCE: 207
tcaaggcttt ctgaggc                                           17

<210> SEQ ID NO 208
<211> LENGTH: 20
<212> TYPE: DNA
<213> ORGANISM: Artificial Sequence
<220> FEATURE:
<223> OTHER INFORMATION: D6S1598 reverse primer

<400> SEQUENCE: 208
agcatggatt ctgttgtttg                                        20

<210> SEQ ID NO 209
<211> LENGTH: 18
<212> TYPE: DNA
<213> ORGANISM: Artificial Sequence
<220> FEATURE:
<223> OTHER INFORMATION: D6S1640 forward primer

<400> SEQUENCE: 209
agccaggcat gctaacat                                          18

<210> SEQ ID NO 210
<211> LENGTH: 19
<212> TYPE: DNA
<213> ORGANISM: Artificial Sequence
<220> FEATURE:
<223> OTHER INFORMATION: D6S1640 reverse primer

<400> SEQUENCE: 210
ggattacagg cacccagta                                         19

<210> SEQ ID NO 211
<211> LENGTH: 21
<212> TYPE: DNA
<213> ORGANISM: Artificial Sequence
<220> FEATURE:
<223> OTHER INFORMATION: D6S1547 forward primer

<400> SEQUENCE: 211
ccttgagcac cttaaatttt t                                      21

<210> SEQ ID NO 212
<211> LENGTH: 22
<212> TYPE: DNA
<213> ORGANISM: Artificial Sequence
<220> FEATURE:
<223> OTHER INFORMATION: D6S1547 reverse primer

<400> SEQUENCE: 212
taactgacaa agcagaatag ca                                     22

<210> SEQ ID NO 213
<211> LENGTH: 24
<212> TYPE: DNA
<213> ORGANISM: Artificial Sequence
<220> FEATURE:
<223> OTHER INFORMATION: D6S1674 forward primer

<400> SEQUENCE: 213
ccttaaacaa acaataagac cacc                                   24
```

<210> SEQ ID NO 214
<211> LENGTH: 20
<212> TYPE: DNA
<213> ORGANISM: Artificial Sequence
<220> FEATURE:
<223> OTHER INFORMATION: D6S1674 reverse primer

<400> SEQUENCE: 214
cagcctagaa aacagagcca                                               20

<210> SEQ ID NO 215
<211> LENGTH: 20
<212> TYPE: DNA
<213> ORGANISM: Artificial Sequence
<220> FEATURE:
<223> OTHER INFORMATION: GATA161F06 primer

<400> SEQUENCE: 215
gaggttgctt gaaatccatg                                               20

<210> SEQ ID NO 216
<211> LENGTH: 22
<212> TYPE: DNA
<213> ORGANISM: Artificial Sequence
<220> FEATURE:
<223> OTHER INFORMATION: GATA161F06 primer

<400> SEQUENCE: 216
gaatctcatc taccctgttt gg                                            22

<210> SEQ ID NO 217
<211> LENGTH: 23
<212> TYPE: DNA
<213> ORGANISM: Artificial Sequence
<220> FEATURE:
<223> OTHER INFORMATION: GATA21F07 primer

<400> SEQUENCE: 217
atactccgag ctatctgtct acc                                           23

<210> SEQ ID NO 218
<211> LENGTH: 20
<212> TYPE: DNA
<213> ORGANISM: Artificial Sequence
<220> FEATURE:
<223> OTHER INFORMATION: GATA21F07 primer

<400> SEQUENCE: 218
ggtgcagatc atgacctctc                                               20

<210> SEQ ID NO 219
<211> LENGTH: 20
<212> TYPE: DNA
<213> ORGANISM: Artificial Sequence
<220> FEATURE:
<223> OTHER INFORMATION: GATA51B02 primer

<400> SEQUENCE: 219
catggatgca gaattcacag                                               20

<210> SEQ ID NO 220
<211> LENGTH: 20
<212> TYPE: DNA
<213> ORGANISM: Artificial Sequence
<220> FEATURE:
<223> OTHER INFORMATION: GATA51B02 primer -continued

```
<400> SEQUENCE: 220
tcatctccct gtttggtagc                                          20

<210> SEQ ID NO 221
<211> LENGTH: 20
<212> TYPE: DNA
<213> ORGANISM: Artificial Sequence
<220> FEATURE:
<223> OTHER INFORMATION: GATA53C06 primer

<400> SEQUENCE: 221
ggtttgctgg catctgtatt                                          20

<210> SEQ ID NO 222
<211> LENGTH: 20
<212> TYPE: DNA
<213> ORGANISM: Artificial Sequence
<220> FEATURE:
<223> OTHER INFORMATION: GATA53C06 primer

<400> SEQUENCE: 222
tgtctggagg cttttcagtc                                          20

<210> SEQ ID NO 223
<211> LENGTH: 20
<212> TYPE: DNA
<213> ORGANISM: Artificial Sequence
<220> FEATURE:
<223> OTHER INFORMATION: GGAA29H03 primer

<400> SEQUENCE: 223
acctgttgta tggcagcagt                                          20

<210> SEQ ID NO 224
<211> LENGTH: 20
<212> TYPE: DNA
<213> ORGANISM: Artificial Sequence
<220> FEATURE:
<223> OTHER INFORMATION: GGAA29H03 primer

<400> SEQUENCE: 224
ggttgactct ttccccaact                                          20

<210> SEQ ID NO 225
<211> LENGTH: 20
<212> TYPE: DNA
<213> ORGANISM: Artificial Sequence
<220> FEATURE:
<223> OTHER INFORMATION: GGAT12E07 primer

<400> SEQUENCE: 225
gtctgtccat ccattcatcc                                          20

<210> SEQ ID NO 226
<211> LENGTH: 20
<212> TYPE: DNA
<213> ORGANISM: Artificial Sequence
<220> FEATURE:
<223> OTHER INFORMATION: GGAT12E07 primer

<400> SEQUENCE: 226
cctcttctcc atgaggacct                                          20
```

```
<210> SEQ ID NO 227
<211> LENGTH: 22
<212> TYPE: DNA
<213> ORGANISM: Artificial Sequence
<220> FEATURE:
<223> OTHER INFORMATION: UT1213 primer

<400> SEQUENCE: 227
acttaaatgt ccatcaataa at                                            22

<210> SEQ ID NO 228
<211> LENGTH: 21
<212> TYPE: DNA
<213> ORGANISM: Artificial Sequence
<220> FEATURE:
<223> OTHER INFORMATION: UT1213 primer

<400> SEQUENCE: 228
tgattggctt tttttactta c                                             21

<210> SEQ ID NO 229
<211> LENGTH: 19
<212> TYPE: DNA
<213> ORGANISM: Artificial Sequence
<220> FEATURE:
<223> OTHER INFORMATION: UT1585 primer

<400> SEQUENCE: 229
tgaactccgg cctgggtga                                                19

<210> SEQ ID NO 230
<211> LENGTH: 19
<212> TYPE: DNA
<213> ORGANISM: Artificial Sequence
<220> FEATURE:
<223> OTHER INFORMATION: UT1585 primer

<400> SEQUENCE: 230 tttttggagct ggggatgtc                                               19

<210> SEQ ID NO 231
<211> LENGTH: 19
<212> TYPE: DNA
<213> ORGANISM: Artificial Sequence
<220> FEATURE:
<223> OTHER INFORMATION: UT1508 primer

<400> SEQUENCE: 231
cctcagtttt ctctcctgc                                                19

<210> SEQ ID NO 232
<211> LENGTH: 20
<212> TYPE: DNA
<213> ORGANISM: Artificial Sequence
<220> FEATURE:
<223> OTHER INFORMATION: UT1508 primer

<400> SEQUENCE: 232
tgctgctata tgctttgcag                                               20

<210> SEQ ID NO 233
<211> LENGTH: 19
<212> TYPE: DNA
<213> ORGANISM: Artificial Sequence
<220> FEATURE:
<223> OTHER INFORMATION: UT2021 primer
```

-continued

```
<400> SEQUENCE: 233
tgggtgacag agctagtcc                                              19

<210> SEQ ID NO 234
<211> LENGTH: 18
<212> TYPE: DNA
<213> ORGANISM: Artificial Sequence
<220> FEATURE:
<223> OTHER INFORMATION: UT2021 primer

<400> SEQUENCE: 234
gaaccagcct cgcatacc                                               18

<210> SEQ ID NO 235
<211> LENGTH: 20
<212> TYPE: DNA
<213> ORGANISM: Artificial Sequence
<220> FEATURE:
<223> OTHER INFORMATION: UT7738 primer

<400> SEQUENCE: 235
ttgcagtgag aagagattgt                                             20

<210> SEQ ID NO 236
<211> LENGTH: 20
<212> TYPE: DNA
<213> ORGANISM: Artificial Sequence
<220> FEATURE:
<223> OTHER INFORMATION: UT7738 primer

<400> SEQUENCE: 236
gcacaagaat cagataagga                                             20

<210> SEQ ID NO 237
<211> LENGTH: 20
<212> TYPE: DNA
<213> ORGANISM: Artificial Sequence
<220> FEATURE:
<223> OTHER INFORMATION: UT7739 primer

<400> SEQUENCE: 237
accctgtact tgtcaaggtt                                             20

<210> SEQ ID NO 238
<211> LENGTH: 20
<212> TYPE: DNA
<213> ORGANISM: Artificial Sequence
<220> FEATURE:
<223> OTHER INFORMATION: UT7739 primer

<400> SEQUENCE: 238
aatcatgtga accagtttcc                                             20

<210> SEQ ID NO 239
<211> LENGTH: 19
<212> TYPE: DNA
<213> ORGANISM: Artificial Sequence
<220> FEATURE:
<223> OTHER INFORMATION: UT7953 primer

<400> SEQUENCE: 239
tggtgggtct gcgtgtgtg                                              19
```

```
-continued

<210> SEQ ID NO 240
<211> LENGTH: 19
<212> TYPE: DNA
<213> ORGANISM: Artificial Sequence
<220> FEATURE:
<223> OTHER INFORMATION: UT7953 primer

<400> SEQUENCE: 240
ggtgctggga ttcggtgca                                              19
```

SUSCEPTABILITY AND RESISTANCE GENES FOR BIPOLAR AFFECTIVE DISORDER

CROSS-REFERENCE TO RELATED APPLICATIONS

This application is a continuation of application Ser. No. 09/175,158 (filed Oct. 19, 1998, now abandoned), which claims priority to U.S. Provisional Application Ser. No. 60/062,924 (filed Oct. 20, 1997, now abandoned). Application Ser. No. 09/175,158 is also a Continuation-In-Part of application Ser. No. 08/827,568, filed Mar. 28, 1997, now abandoned, which claims priority to U.S. Provisional Application Ser. No. 60/014,334 (filed Mar. 29, 1996). These disclosures are incorporated herein by reference for all purposes.

BACKGROUND OF THE INVENTION

1. Field of the Invention

This invention relates to the field of diagnosis and treatment of bipolar affective disorders.

2. Background

The most characteristic features of bipolar affective disorder (manic-depressive illness) are episodes of mania (bipolar I, BPI) or hypomania (bipolar II, BPII) that are interspersed with periods of depression. If untreated, manic-depressive illness is associated with an approximately 20% risk of suicide. Even with treatment, this disorder constitutes a major public health problem, afflicting approximately one percent of the population. Goodwin et al., *Manic-Depressive Illness* (Oxford University Press, New York, 1990).

Although little is known about the etiology or pathophysiology of bipolar affective disorder, genetic and environmental factors contribute to its pathogenesis, especially in families with multiple affected members. Considerable genetic and epidemiologic data derived from twin, family and adoption studies provide compelling evidence for a genetic etiology of this disorder, but the mode(s) of inheritance has not been identified. Craddock et al., *Ann. Med.* 25:317–322 (1993). Nonetheless, to date, the majority of genetic linkage studies of bipolar affective disorder have assumed that it exhibits classical Mendelian inheritance attributable to a single major gene. Segregation analyses have yielded inconsistent results with most studies rejecting a single dominant or recessive locus inheritance model. However, if only BPI is considered, the best single gene model is dominant inheritance. Pauls et al., *Neuropsy. Genet.*, 60:290–297 (1995).

Due to the complexities inherent in linkage studies of psychiatric disorders, one study has focused on the identification of a gene for bipolar illness in a large Old Order Amish pedigree in southeastern Pennsylvania. Egeland et al., *Nature*, 325:783–787 (1987). The Old Order Amish are a religious sect numbering approximately 15,000 who descend from some 30 pioneer couples and who have remained genetically isolated, thereby minimizing the introduction of multiple genes responsible for inherited disorders. Amish families have large sibships and multiple living generations, making them ideal for genetic studies. Further, alcohol and drug abuse, which often complicate psychiatric diagnoses, are rare among the Amish. Bipolar affective disorder, however, occurs amongst the Old Order Amish with a prevalence rate, characteristic symptom pattern and clinical course that are similar to those in the general North American population. The identification and characterization of these pedigrees led to the initiation of early genetic linkage studies but no evidence for linkage between various polymorphic serum proteins or blood group antigen loci and affective disorder was found.

More recently, using a molecular genetic approach, Egeland and colleagues reported evidence supporting the localization of a gene conferring a strong predisposition to bipolar affective disorder linked to two loci located on the short arm of chromosome 11, the Harvey-ras-1 oncogene locus (HRAS) and the insulin (INS) locus. Id. However, reanalysis of the Old Order Amish pedigree to include several new individuals, two changes in clinical status, and a large lateral extension of the original pedigree markedly reduced the probability of linkage between bipolar affective disorder and the HRAS and INS loci. Kelsoe et al., *Nature*, 342:238–243 (1989).

Attempts to replicate linkage findings for bipolar affective disorder have proven problematic and have been plagued by diagnostic uncertainties, genetic heterogeneity, phenocopies, genotyping errors, and the complexities of performing and interpreting statistical analyses (Egeland et al. (1987) *Nature* 325, 783–787; Pekkarinen et al. (1995) *Genome Res.* 5: 105–115; Ginns et al. (1996) *Nature Genet.* 12, 431–435; NIMH Genetics Initiative Bipolar Group (1997) *Am. J. of Med. Genetics* (Neuropsych. Genetics) 74, 227–269; Blackwood et al. (1996) *Nature Genet.* 12, 427–430; Freimer et al. (1996) Nature Genet. 12, 436–441). Reported linkages of bipolar affective disorder to DNA markers on chromosomes 18, 21 and X have been difficult to replicate and several proposed linkages have been refuted upon reanalysis. Kelsoe et al., *Nature*, 342:238–243 (1989), Berrettini et al., *Proc. Natl. Acad. Sci. USA*, 91:5918–5921 (1994), Straub et al., *Nature Gen.* 8:291–296 (1994), Baron et al., *Nat. Genet.*, 3:49–55 (1993), Pauls et al., *Am. J. Hum. Genet.*, 57:636–643 (1995).

Moreover, since the inheritance of BPAD is probably multifactorial, the possible involvement of multiple genetic components of small effect and/or the occurrence of major allelic effects only in epistasis must be considered. In addition to susceptibility alleles, there could be alleles that reduce the risk of developing BPAD in a manner similar to that reported for other complex genetic disorders (Philibert et al. (1997) *J. Affective Disorders* 43, 1–3). If model-based linkage analyses are used, a "false negative" linkage finding could result when individuals inherit disease susceptibility alleles but do not manifest the phenotype due to the presence of "protective" alleles. The inclusion of individuals who inherit susceptibility alleles but do not manifest disease because of "protective" alleles, or of individuals who inherit "protective" alleles but nevertheless manifest the disease, will also reduce the power of model-free (allele-sharing) analyses. Thus, regardless of whether model-based or model-free analyses are used, "wellness" or "protective" alleles could have a significant impact on linkage analyses.

Given the magnitude of the public health problem associated with bipolar illness and the availability of treatments for this disorder, what is needed in the art is a means to determine the risk to an individual, who comes from an affected family, of developing bipolar affective disorder. Given that risk can depend both on susceptibility and protective alleles, it is desirable to have means to determine the presence or absence of both types of alleles associated with bipolar affective disorder. Quite surprisingly, the present invention provides these and other advantages.

SUMMARY OF THE INVENTION

Regions of chromosomes 6, 13, and 15 have been determined to comprise loci which are associated with susceptibility to bipolar affective disorder (BPAD), while regions of chromosome 4 and chromosome 11 are associated with resistance to BPAD. Compositions and methods to determine the various forms of these loci are useful for a variety of diagnostic procedures.

In one aspect, the present invention provides genetically based methods and kits for determining a genotype associated with an increased or decreased susceptibility to familial bipolar affective disorder in a family affected by bipolar affective disorder. The method comprises determining the genotype of at least one family member, wherein the genotype is determined with at least one marker for at least one chromosomal region linked to a locus associated with susceptibility to bipolar affective disorder. The chromosomal regions are inclusive of and localized between markers D6S344 and D6S89 on chromosome 6, markers D13S171 and D13S218 on chromosome 13, or markers D15S153 and D15S117 on chromosome 15, such as at about marker D15S148 on chromosome 15. The bipolar affective disorder disease status is determined for the family member after the age of onset. The genotype and disease status of the family member are compared to determine the genotype associated with increased or decreased susceptibility to bipolar affective disorder. In one embodiment, the genotype is determined with markers to at least two chromosomal regions linked to a locus associated with susceptibility to bipolar affective disorder. Preferably, the genotype is determined with markers D6S7, D13S1, or D15S45, or combinations thereof. In another embodiment, the genotype of an affected family member is determined. In a further embodiment, the markers are restriction fragment length polymorphisms or microsatellite markers. In yet another embodiment, the genotype which indicates either the presence or absence of a bipolar illness allele is determined.

In another aspect, the present invention provides methods and compositions for determining the increased or decreased risk of a tested individual developing familial bipolar affective disorder by comparing the disease genotype of the tested individual to the genotype of a family member which is associated with increased or decreased susceptibility to bipolar affective disorder. The disease genotype is determined with at least one marker for at least one chromosomal region linked to a locus associated with susceptibility to bipolar affective disorder. The chromosomal regions are inclusive of and localized between markers D6S344 and D6S89 on chromosome 6, markers D13S171 and D13S218 on chromosome 13, or markers D15S153 and D15S117 on chromosome 15 such as, for example, at about marker D15S148 on chromosome 15. In one embodiment, the genotype of the tested individual is compared to the genotype of an affected family member. In another embodiment, the genotype of the tested individual is determined with markers D6S7, D13S1, or D15S45, or combinations thereof. In yet another embodiment, the genotype of the tested individual and family member are determined at all three chromosomal regions of the present invention.

The invention also provides genetically based methods and kits for determining a genotype associated with an increased or decreased susceptibility to familial bipolar affective disorder in which markers associated with resistance to bipolar affective disorder are detected. The methods involve determining the genotype of at least one family member, wherein the genotype is determined with at least one marker for at least one chromosomal region linked to a locus associated with resistance to bipolar affective disorder. The chromosomal regions are on chromosome 4, inclusive of and localized between markers D4S402 and D4S424 and markers D4S431 and D4S404, and on chromosome 11, inclusive and localized between D11S394 and D11S29. The bipolar affective disorder disease status is determined for the family member after the age of onset. The genotype and disease status of the family member are compared to determine the genotype associated with increased or decreased susceptibility to bipolar affective disorder. In one embodiment, the genotype is determined with markers to at least two chromosomal regions linked to a locus associated with resistance to bipolar affective disorder. Preferred markers for determining the genotype on chromosome 4q include, for example, D4S175, D4S422, D4S1576, D4S2294, D4S1579, D4S397, D4S3089, D4S2965, D4S192, D4S420, D4S1644, D4S3334, or combinations thereof. Preferred markers for determining resistance alleles on chromosome 4p include, for example, D4S3007, D4S394, D4S2983, D4S2923, D4S615, AFM$_\alpha$184za9, D4S2928, D4S1065, D4S1582, D4S107, D4S3009, D4S2906, D4S2949, AFM087zg5, D4S2944, D4S403, D4S2942, D4S2984, D4S1602, D4S1511, D4S2311, D4S3048or combinations thereof. On chromosome 11, preferred markers include, for example, D11S133, D11S147, CD3D, D11S285, D11S29, or combinations thereof.

In some embodiments of the invention, the genotype of an affected family member is determined. In a further embodiment, the markers are restriction fragment length polymorphisms or microsatellite markers. In yet another embodiment, the genotype which indicates either the presence or absence of a bipolar illness allele is determined.

In another aspect, the present invention provides methods and compositions for determining the increased or decreased risk of a tested individual developing familial bipolar affective disorder by comparing the disease genotype of the tested individual to the genotype of a family member which is associated with increased or decreased susceptibility to bipolar affective disorder. The disease genotype is determined with at least one marker for at least one chromosomal region linked to a locus associated with resistance to bipolar affective disorder. The chromosomal regions are on chromosome 4, inclusive of and localized between markers D4S402 and D4S424 and markers D4S431 and D4S404, and on chromosome 11, inclusive and localized between D11S394 and D11S29. In one embodiment, the genotype of the tested individual is compared to the genotype of an affected family member. In yet another embodiment, the genotype of the tested individual and family member are determined at all three chromosomal regions of the present invention.

Another embodiment of the invention provides compositions, methods and kits for determining the presence of a genotype associated with resistance to bipolar affective disorder in a family affected by BPAD. These methods involve determining the genotype of at least one family member, wherein the genotype is determined with at least one marker for at least one chromosomal region linked to a locus associated with resistance to bipolar affective disorder. The chromosomal regions are on chromosome 4, inclusive of and localized between markers D4S402 and D4S424 and markers D4S431 and D4S404, and on chromosome 11, inclusive and localized between D11S394 and D11S29. In one embodiment, the genotype is determined with markers to at least two chromosomal regions linked to a locus associated with resistance to bipolar affective disorder.

In yet another aspect, the invention provides methods and kits for determining the contribution of a chromosomal region to the presence or absence of bipolar affective disorder, or resistance to BPAD, in a family affected by bipolar affective disorder. The method comprises determining the corresponding genotype of at least two family members, wherein the genotype is determined with at least one marker for at least one tested chromosomal region linked to a locus associated with susceptibility or resistance to bipolar affective disorder. The tested chromosomal regions for susceptibility are inclusive of and localized between D6S344 and D6S89, D13S171 and D13S218, or at about D15S148; for resistance the tested chromosomal regions are inclusive of and localized between either or D4S402 and D4S424 and markers D4S431 and D4S404, and on chromosome 11, inclusive and localized between D11S394 and D11S29. The bipolar affective disease status in the family members is determined after the age of onset and compared to the genotypes of the family members. As a result of this comparison, the contribution of the chromosomal region to the presence or absence of bipolar affective disorder in the family is determined. In one embodiment, corresponding genotype of at least two family members affected by bipolar illness is determined. In another embodiment, at least one of the markers D6S7, D13S1, or D15S45 is used to determine susceptibility, and D4S2949, D4S175, and D4S397 to determine resistance.

BRIEF DESCRIPTION OF THE FIGURES

FIG. 4 shows the locations of markers on human chromosome 13 that are associated with susceptibility to BPAD. The statistical significance of the genetic linkage between markers based on sib-pair analysis is shown at left, and map distances between markers (in centimorgans) are indicated in the rightmost two columns.

FIG. 6 shows the locations of markers on human chromosome 4p that are associated with resistance to BPAD. The statistical significance of the genetic linkage between markers based on sib-pair analysis is shown at left, and map distances between markers (in centimorgans) are indicated in the rightmost two columns.

FIG. 7 shows the locations of markers on human chromosome 4q that are associated with resistance to BPAD. The statistical significance of the genetic linkage between markers based on sib-pair analysis is shown at left, and map distances between markers (in centimorgans) are indicated in the rightmost two columns.

FIG. 12A: $-\log_{10}p$ for markers on chromosome 4p: -----, Pedigree 110 only; and —, Pedigrees 110, 210, 310 and 410; FIG. 12B: $-\log_{10}p$ for markers on chromosome 4q: -----, Pedigree 110 only; and —, Pedigrees 110, 210, 310 and 410.

DESCRIPTION OF THE PREFERRED EMBODIMENT

Introduction

Figure 1:
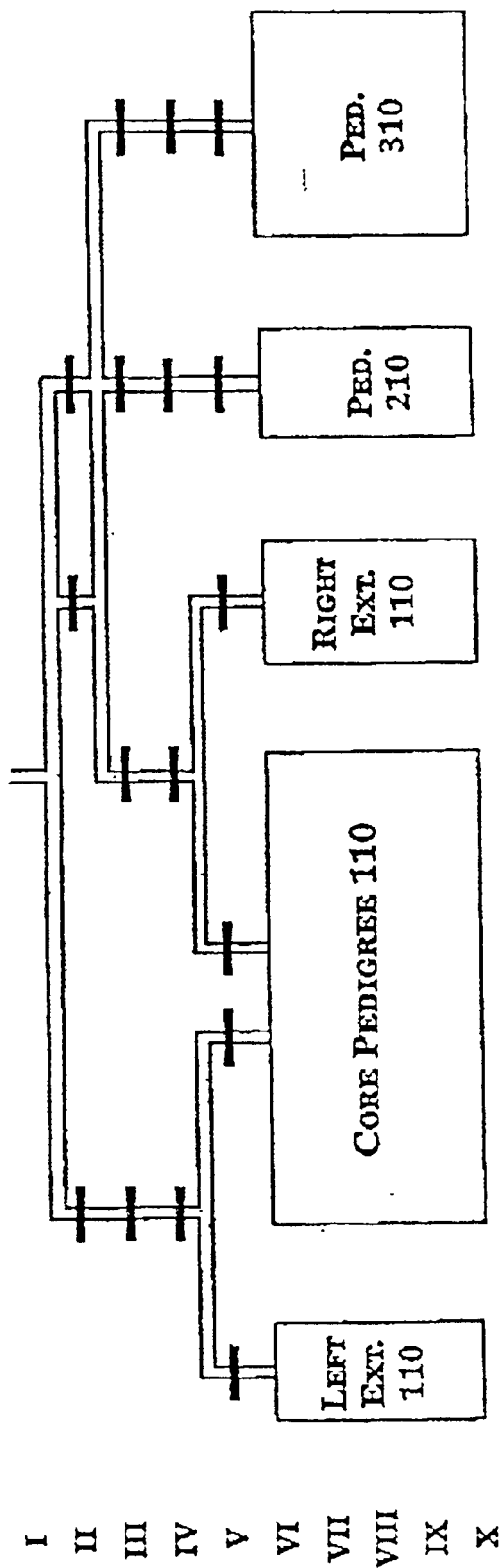
FIG. 1 summarizes each pedigree in "block" form illustrating that all of the BPI pedigrees trace along pathways leading to a common progenitor, one of some 30 couples that founded the present Lancaster County, Old Order Amish group.
Figure 2:
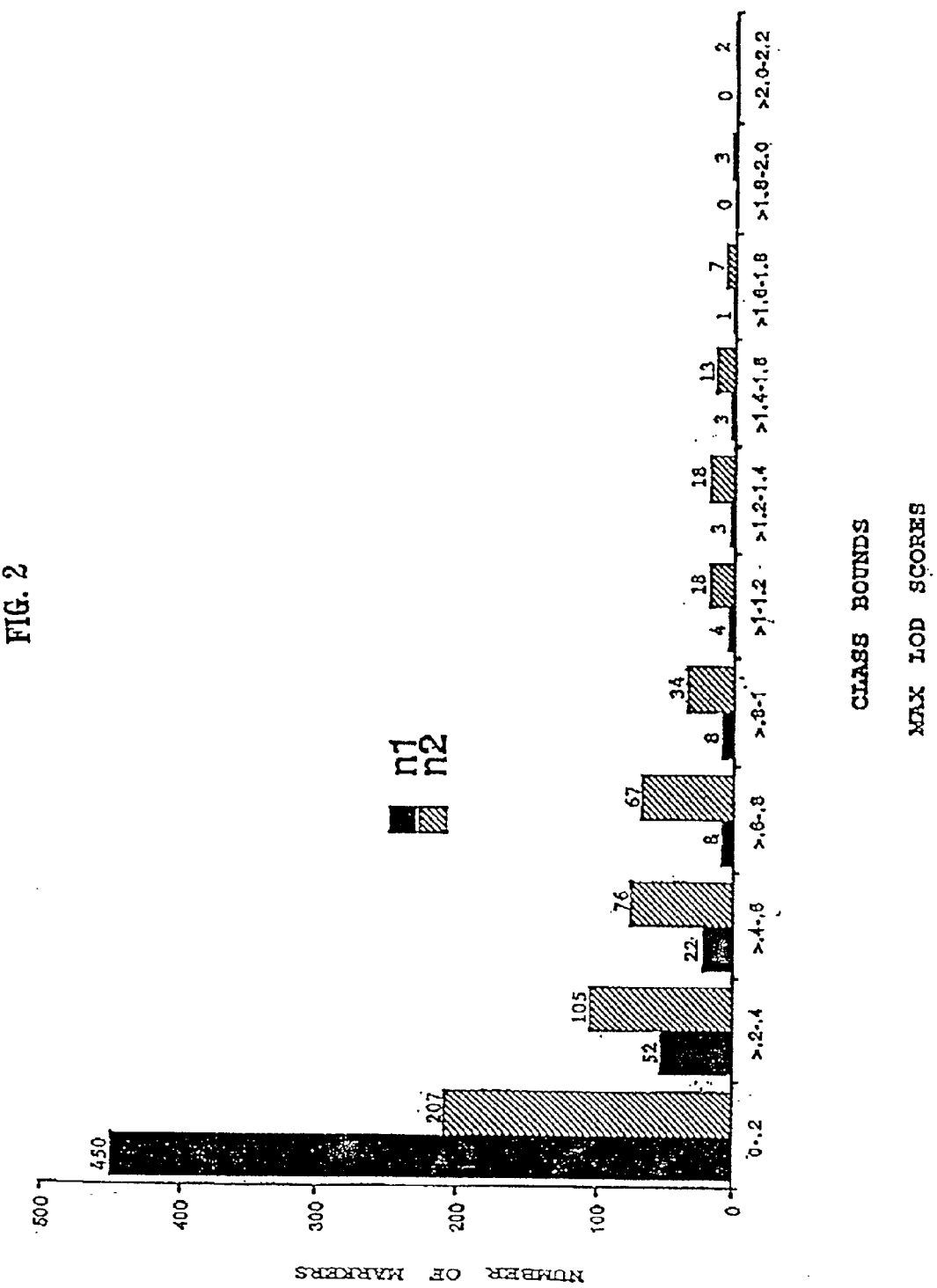
FIG. 2 shows the maximum lod scores, using BPI as affected diagnosis, for two scenarios: (N1)—nuclear families, homogeneity, dominant inheritance, and affecteds only; and (N2)—sixteen combinations of analyses for each marker including: dominant vs. recessive inheritance, five pedigrees vs. nuclear families, homogeneity vs. heterogeneity, and affecteds only vs affecteds and unaffecteds. N1 and N2 represent the number of markers furnishing maximum lod scores within given class boundaries for scenarios 1 and 2, respectively.

In the present invention, regions of chromosome 6, 13, and 15 have been identified that comprise loci that are associated with susceptibility to a familial form of bipolar affective disorder (BPAD). Ginns et al. (1996) Nature Genet. 12, 431–435. Additional chromosome regions on chromosome 4 and chromosome 11 are associated with resistance to BPAD. Genotypic identification of the loci associated with either the presence or absence of familial bipolar affective disorder provides a means to assess the risk of a tested individual from an affected family having or developing the disease. Moreover, the present invention also provides the means to assess whether these loci are implicated in the presence or absence of bipolar illness in an individual.

Accordingly, the methods and compositions of the present invention provide a means to alert clinicians to a genetic predisposition towards, or resistance to, bipolar affective disorder. The methods of the invention are useful in genetic counseling of individuals from families affected with bipolar illness, and aid in the differential diagnosis of bipolar illness from other psychiatric pathologies.

Definitions

As used herein, "bipolar illness," or "bipolar affective disorder," or "manic depression" refer to bipolar I (BPI), bipolar II (BPII), or major depressive disorder (MDD). See, "Research Diagnostic Criteria," Spitzer et al., Arch. Gen. Psychiat., 35:773–782 (1978), incorporated herein by reference. The term "familial" as applied to the defined terms denotes a genetic contribution to the development of bipolar affective disorder as opposed to a strictly environmental etiology.

As used herein "allele associated with increased susceptibility to bipolar illness" or "bipolar illness allele" or "disease allele" refers to a form of a locus on a chromosome which, when present in an individual, directly or indirectly causes or increases the risk of developing bipolar illness. Similarly, "allele associated with increased resistance to bipolar illness" refers to a form of a locus on a chromosome which, when present in an individual, directly or indirectly increases the resistance of that individual to bipolar illness. The locus may be any DNA sequence, e.g., a gene or genes or fragments thereof or a regulatory element.

As used herein "locus associated with susceptibility to bipolar illness" refers to a locus on a chromosome which in at least one form is an "allele associated with increased susceptibility to bipolar illness." A "locus associated with resistance to bipolar illness" refers to a locus on a chromosome which in at least one form is an "allele associated with increased resistance to bipolar illness."

As used herein, "marker" or "polymorphic marker" refers to a polymorphic locus that serves to identify a unique locus on a chromosome. An "informative marker" appears in different forms on each homologous pair of chromosomes such that inheritance of the individual chromosomes can be followed. An informative marker may be comprised of two or more markers that individually are not informative.

As used herein, "family member" refers to an individual's consanguineous grandparent, parent, child, or sibling although a more distant blood-relative may be used. The family member may be alive or deceased.

As used herein, "family" refers to two or more consanguineous individuals. A family may consist of individuals from the same generation or from 2, 3, 4, 5, 6, 7, 8, 9, or 10–15 generations. Thus, a family may consist of ethnic groups or subgroups thereof or a geographically secluded interbreeding population having a common ancestor.

As used herein, "linked" refers to the greater association in inheritance of two or more non-allelic loci than is to be expected from independent assortment. Loci are linked because they reside on the same chromosome. Generally, linked loci are separated by less than 50 centimorgans, preferably less than 30 or 40 centimorgans, and most preferably less than 20 or 10 centimorgans.

As used herein, "chromosomal region" refers to a length of chromosome which may be measured by reference to the linear segment of DNA which it comprises. The 5' and/or 3' termini of the chromosomal region can be defined by reference to a unique DNA sequence, i.e., a marker. The chromosomal region may be inclusive or exclusive of the defining 5' or 3' terminal DNA sequences. Alternatively or additionally, the 5' and/or 3' termini of a chromosomal region can be defined by reference to a length of DNA extending from a unique DNA sequence. Typically the length extending from a unique DNA sequence is about 10 centimorgans (or million basepairs) or less, and may be 9, 8, 7, 6, 5, 4, 3, 2 or 1 centimorgans (or million basepairs) or fractional values thereof wherein the distance in centimorgans is the sex-averaged value.

As used herein, "age of onset" refers to the age at which those who develop bipolar affective disorder first exhibit its clinically defined symptoms. The age of onset may occur at 15 years of age, usually at between 15–20, or 21–25 years of age, and may occur at 26–30 or 31–35 years of age.

As used herein, "genotype associated with increased susceptibility to bipolar affective disorder" refers to a genotype which has a higher probability of occurrence in bipolar affective disorder affected family member(s) than in family members who are past the age of onset but not affected by bipolar affective disorder.

As used herein, "genotype associated with increased resistance to bipolar affective disorder" refers to a genotype which has a higher probability of occurrence in individuals who are wholly or partially resistant to BPAD.

As used herein, a "genotype" may be defined by use of a single or a plurality of markers.

As used herein, "genotype associated with decreased susceptibility to bipolar affective disorder" refers to a genotype which has a lower probability of occurrence in bipolar affective disorder affected family member(s) than in family members who are past the age of onset but not affected by bipolar affective disorder.

As used herein, "genotype associated with increased or decreased susceptibility to bipolar affective disorder" refers to a "genotype associated with increased susceptibility to bipolar affective disorder" or a "genotype associated with decreased susceptibility to bipolar affective disorder."

As used herein, "increased" means greater than 50%.

As used herein, "decreased" means less than 50%.

As used herein, "determining" the "risk of the tested individual developing familial bipolar affective disorder" means ascertaining the probability of the tested individual developing bipolar affective disorder after the individual reaches the age of onset. The determination of risk may be a quantitatively assessed or may be assessed qualitatively as higher, lower, or equivalent to a family member whose corresponding genotype is determined at one or more chromosomal regions linked to a locus associated with susceptibility to bipolar affective disorder.

As used herein, "corresponding genotype" refers to a genotype obtained using at least one marker from within the same chromosomal region used to genotype another family member such that a basis of comparison at that same chromosomal region is provided. A corresponding genotype may conveniently be determined using at least one of the same markers.

As used herein, "tested individual" refers to an individual, pre- or post-partum, whose genotype is determined and includes a proband. The tested individual is a family member from the same family as the family member whose genotype the tested individual's is compared to.

As used herein, "bipolar illness genotype" refers to a genotype determined with at least one marker for at least one chromosomal region linked to a locus associated with susceptibility to bipolar affective disorder, wherein the tested chromosomal regions are inclusive of and localized between D6S344 and D6S89, D13S171 and D13S218, or at about D15S148.

As used herein, "bipolar illness resistance genotype" refers to a genotype determined with at least one marker for at least one chromosomal region linked to a locus associated with resistance to bipolar affective disorder, wherein the tested chromosomal regions are inclusive of and localized between markers D4S402 and D4S1625 and markers D4S431 and D4S404.

In the form of bipolar affective disorder addressed herein, one or more of the loci associated with susceptibility to bipolar affective disorder have a higher probability of occurring as a disease allele in a bipolar illness affected family member than in a non-affected family member. Conversely, in non-affected family members, one or more of the loci which are associated with susceptibility to bipolar affective disorder have an increased probability of occurring in a form not found in bipolar illness affected family members. This statistical correlation provides the means of determining whether a particular genotype is associated with increased or decreased susceptibility to bipolar affective disorder. Further, this correlation allows one to determine whether and which of the one, two, or three chromosomal regions of the present invention contribute to bipolar illness in the affected family. And, since susceptibility to bipolar illness increases with the number of bipolar illness alleles of an individual, the methods and compositions provide means of determining a tested individual's increased or decreased risk of developing bipolar illness.

Similarly, one or more of the loci associated with resistance to BPAD have a higher probability of occurring as a resistance allele in a family member that is not affected with BPAD than in an affected family member. The statistical correlation provides a means for determining whether a particular genotype is associated with increased or decreased resistance to BPAD.

The methods of the present invention generally comprise determining the genotype of at least one family member from a family affected by bipolar affective disorder. The affected family will have at least one member with bipolar affective disorder, preferably, two, three, four, or more members with bipolar affective disorder. As will be clear to those of skill in the art, the family affected by bipolar illness will preferably have at least one prior or successive generation of family members such that the loci associated with susceptibility to bipolar illness are transmitted between at least two generations. Accordingly, genotyping of two, three, four, or more family members for the bipolar illness genotype is preferred. Even more preferably, these family members will be from two or more different generations; even more preferably three or more generations.

Methods of genotyping are well known to those of skill in the art. Briefly, the methods of determining the bipolar illness genotype typically comprise use of at least one marker for at least one chromosomal region linked to a locus associated with bipolar illness. Typically, nucleic acid probes to a marker within these chromosomal region(s) are used for genotyping. The markers to the chromosomal regions are sufficiently close to the loci which are associated with susceptibility or, depending on the particular chromosomal region tested, resistance to bipolar illness such that following inheritance of the markers allows for following inheritance of a locus or loci associated with increased or decreased susceptibility or resistance to bipolar affective disorder. Each marker is specific to a chromosomal region and DNA sequence variability in markers typically allows a chromosome to be distinguished from its homolog. However, sufficient conservation in DNA sequence by each marker generally allows transmission of the chromosomal region to be traced from generation to generation. A statistically significant correlation between the presence or absence of a chromosomal marker with the presence or absence of bipolar illness in a family member after the age of onset allows for the determination of the genotype(s) associated with increased or decreased susceptibility or resistance to familial bipolar affective disorder. The chromosomal regions of the present invention that display linkage to loci associated with susceptibility to bipolar illness are inclusive of and localized between the markers D6S344 and D6S89 on chromosome 6, D13S171 and D13S218 on chromosome 13, or at about D15S148 on chromosome 15, generally about 10 centimorgans or 10 million basepairs flanking either side of D15S148; preferably localized by, and inclusive of at least, marker D15S117.

Figure 12A:
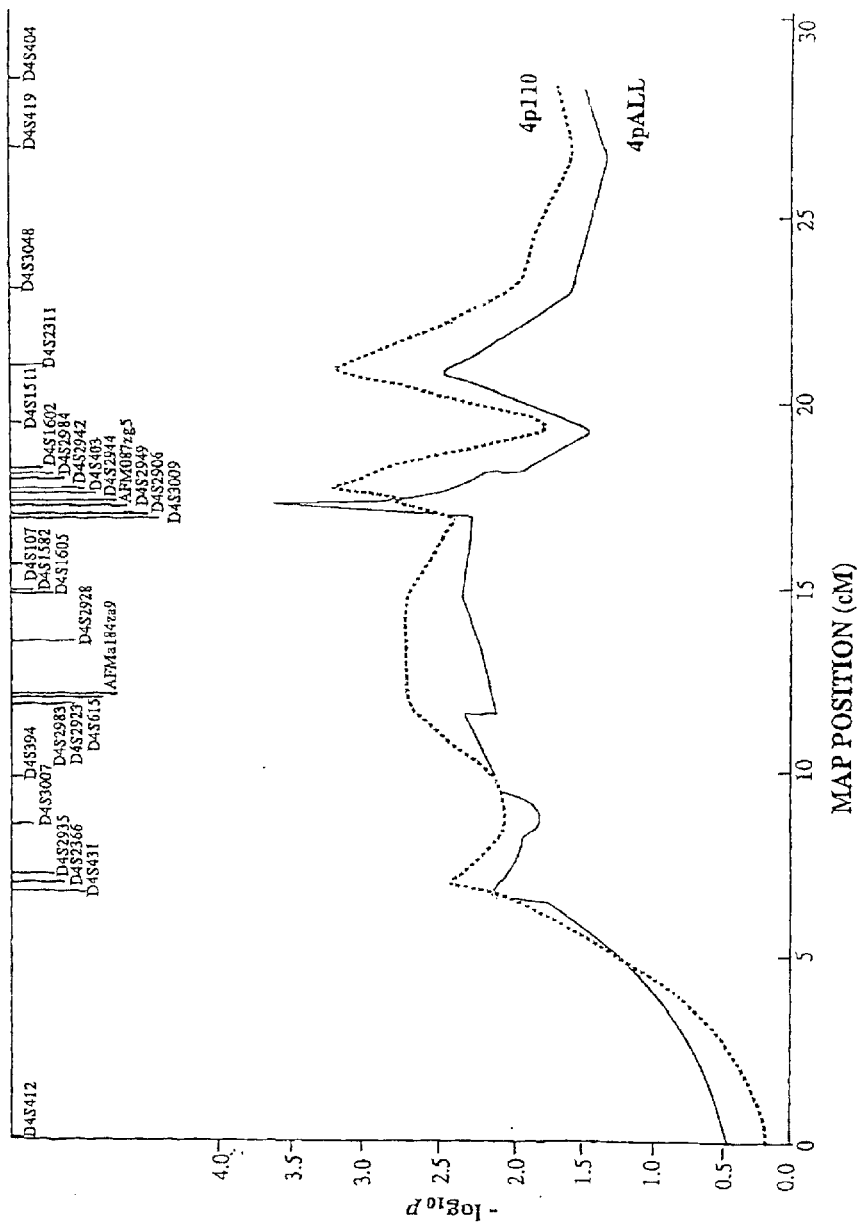
FIGS. 12A and 12B present a model-free linkage analysis of "wellness" using GENEHUNTER-PLUS $-\log_{10}p$. Map position is in Kosambi centimorgans. The $-\log_{10}p$ was calculated using p values generated by GENEHUNTER-PLUS (including individuals>age 45 yrs in all pedigrees) on the assumption that the NPL score is standard normally distributed. A $-\log_{10}p$ of 4.0 corresponds asymptotically to a LOD score of 3.0. Only mentally healthy individuals 45 years of age or older were classified as being 'well' (see, Example IV).
Figure 12B:
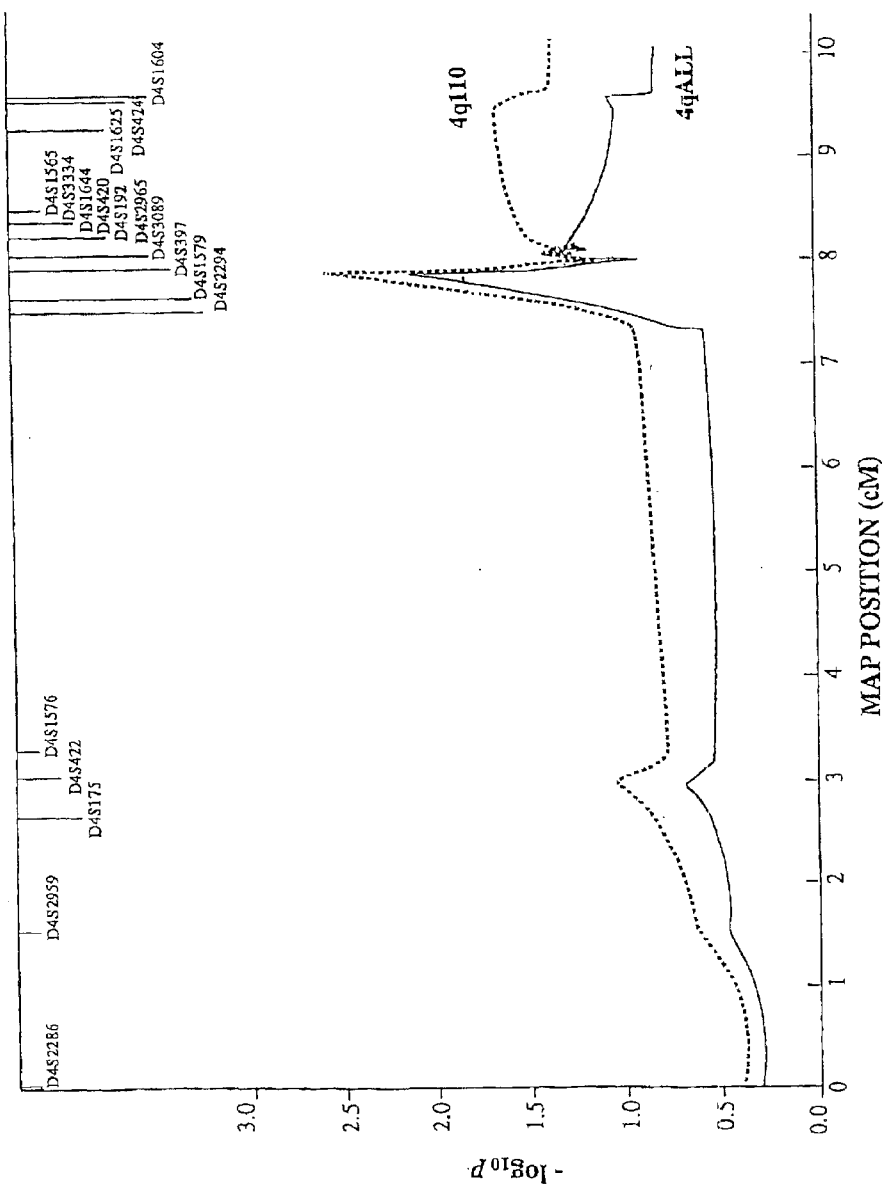

Conversely, chromosomal regions of the invention that are linked to loci associated with increased resistance to BPAD are found on human chromosome 4, more particularly on chromosome arm 4p the regions are inclusive of and localized between markers D4S431 and D4S404 (FIG. 6 and FIG. 12A) and on chromosome arm 4q the regions are inclusive of and localized between markers D4S402 and D4S1625 (FIG. 7 and FIG. 12B). The chromosomal regions on arm 4p are generally about 10 centimorgans or 10 million base pairs flanking either side of D4S2949, more preferably about 5 centimorgans flanking either side of d4S2949. Examples of suitable markers include, for example, D4S3007, D4S394, D4S2983, D4S2923, D4S615, AFM$_\alpha$184za9, D4S2928, D4S1065, D4S1582, D4S107, D4S3009, D4S2906, D4S2949, AFM087zg5, D4S2944, D4S403, D4S2942, D4S2984, D4S1602, D4S1511, D4S2311, D4S3048, or combinations thereof. Particularly preferred markers include D4S3009, D4S2906, D4S2949, AFM087zg5, D4S2944, D4S403, D4S2942, D4S2984, D4S1602, D4S1511, D4S2311, or combinations thereof.

On arm 4q, the chromosomal regions that are linked to loci associated with increased resistance to BPAD are typically within about 10 centimorgans on either side of D4S397, more preferably within about 5 centimorgans on either side of D4S397. Suitable markers include, for example, D4S175, D4S422, D4S1576, D4S2294, D4S1579, D4S397, D4S3089, D4S2965, D4S192, D4S420, D4S1644, D4S3334, or combinations thereof.

An additional chromosomal region that is associated with resistance to BPAD is found on human chromosome 11. This chromosomal region is inclusive of and localized between markers D11S133 and D11S29. Preferred markers for this region include, for example, D11S133, D11S147, CD3D, D11S285, D11S29, or combinations thereof.

The genotype or genotypes associated with increased or decreased susceptibility or resistance to familial bipolar illness is generally determined upon comparison (i.e., correlation) of the genotype of the family member with that family member's bipolar illness disease status after the age of onset. Comparison of the family member's genotype with the family member's disease status allows one to determine the genotype associated with increased or decreased susceptibility or resistance to bipolar affective disorder by the use of statistical methods well known to those of skill in the art. Thus, for example, if the genotype of an affected parent and the genotype of an affected child have only one form of an informative marker in common, comparison of their disease status with their genotypes implicates the particular chromosomal region identified by that common marker as associated with an increased risk of developing bipolar illness, or with an increased resistance to genetic and/or environmentally induced BPAD. Accordingly, the methods of the present invention also allow for the formation of pedigrees of sufficient detail such that determination of an allele(s) associated with increased susceptibility or resistance to bipolar affective disorder may be determined.

Due to the increased probability of meiotic crossover events between markers of the present invention and bipolar illness alleles, determining a bipolar illness genotype is preferably achieved using closer rather than more distantly related relatives. For similar reasons, markers more proximal to the loci associated with increased or decreased susceptibility to bipolar affective disorder are employed, such as D6S7, D13S1, or D15S45, to minimize the chance of crossover events. More preferably, two, three, or more additional markers flanking D6S7, D13S1, or D15S45 are employed to aid in the detection of a recombination event between a marker and the bipolar illness disease allele. Typically, the markers are separated by 1, 2, 3, 4, or 5 centimorgans. Preferably, the markers are informative.

Similarly, for identification of a BPAD-resistant genotype, closer rather than more distantly related relatives are preferred, as are markers more proximal to the loci associated with increased resistance to BPAD. Such markers on chromosome arm 4p include, for example, D4S2366, D4S394a, D4S3007, D4S394, D4S2949, D4S1605, D4S1582, D4S107m, and D4S403 as shown on FIG. 6. On chromosome arm 4q, preferred markers include, for example, D4S422, D4S2423, D4S422a, D4S175, D4S397, D4S3334, and D4S1644 as shown in FIG. 7. On chromosome 11, the preferred markers are in the chromosomal region inclusive of and localized between markers D11S133 and D11S29; these include D11S133, D11S147, CD3D, D11S285, D11S29, or combinations thereof. In each case, the markers are typically separated by 1, 2, 3, 4, or 5 centimorgans. Preferably, the markers are informative.

The present invention also provides methods and compositions for determining a tested individual's increased or decreased risk of inheriting a disease allele. The method comprises determining the bipolar illness genotype of a tested individual from the affected family according to methods described for determining the genotype of a family member. Thus, the genotype is determined with at least one marker for at least one chromosomal region which is linked to a locus associated with resistance to bipolar illness. The chromosomal regions include chromosome arm 4p, where the regions are inclusive of and localized between markers D4S431 and D4S404 (FIG. 6 and FIG. 12A) and chromosome arm 4q, where the regions are inclusive of and localized between markers D4S402 and D4S1625 (FIG. 7 and FIG. 12B). An additional region associated with resistance is found on chromosome 11 inclusive of and localized between markers D11S133 and D11S29. Typically, the markers are separated by 1, 2, 3, 4, or 5 centimorgans.

After determining the tested individual's bipolar illness genotype it is compared to the genotype associated with increased or decreased susceptibility to bipolar affective disorder of the affected family. A corresponding genotype is tested such that at least one equivalent chromosomal region of the present invention is utilized during comparison of the tested individual's genotype with that of the genotype associated with increased or decreased susceptibility to bipolar affective disorder; sometimes two equivalent chromosomal regions are compared, often all three chromosomal regions of the tested individual are compared. Conveniently, at least one identical marker is used for each equivalent chromosomal region compared.

The described comparison provides for a determination of an increased or decreased risk of the tested individual developing familial bipolar affective disorder by assessing the similarities and differences between the compared genotypes. The absence in the tested individual of the form of a susceptibility marker found in the chromosome complements of affected family members signals a reduced risk inheriting a bipolar illness allele and thus, of developing bipolar illness. Conversely, inheritance by the tested individual of a form of the susceptibility marker found in affected family members indicates a correspondingly increased risk of inheriting the bipolar illness allele. Thus, for example, if the same three forms of a marker are inherited by an affected parent and affected child, the absence of any one of these forms of markers in a tested sibling indicates a decreased risk of inheriting the disease allele. In contrast, inheritance by the tested sibling of an increasing number of the bipolar illness genotypes found in the affected family members indicates an increasing risk of inheriting one or more disease alleles. A similar analysis applies to testing for increased or decreased risk of BPAD because of the absence or presence, respectively, of a chromosomal region that is associated with an allele that is involved in resistance to BPAD.

The methods and compositions of the present invention further provide for determining whether a chromosomal region of the present invention is, in fact, contributing to the presence or absence of familial bipolar affective disorder in a family with at least one member affected by bipolar affective disorder. The method comprises determining the corresponding genotype of at least two family members using methods described for determining a genotype associated with increased or decreased susceptibility or resistance to familial bipolar affective disorder. Thus, each genotype is determined with at least one marker for at least one chromosomal region which is linked to a locus associated with susceptibility or resistance to bipolar illness. The chromosomal regions associated with susceptibility are inclusive of and localized between D6S34 and D6S89, D13S171 and D13S218, or at about D15S148, generally inclusive of a chromosomal region localized by at least D15S117. Preferably, the markers comprise D6S7, D13S1, or D15S45. More preferably, markers flanking D6S7, D13S1, or D15S45 are also employed. Typically, the markers are separated by 1, 2, 3, 4, or 5 centimorgans. Chromosomal regions associated with resistance to BPAD are generally are inclusive of and localized between D4S402 and D4S424 (FIG. 12B); inclusive of and localized between D4S431 and D4S404 (FIG. 12A); or inclusive and localized between D11S394 and D11S29. Preferred markers include, for example, D4S2366, D4S394a, D4S3007, D4S394, D4S2949, D4S1605, D4S1582, D4S107m, and D4S403 as shown on FIG. 6, and D4S422, D4S2423, D4S422a, D4S175, D4S397, D4S3334, and D4S1644 as shown in FIG. 7. Other preferred markers for resistance include D4S175, D4S422, D4S1576, D4S2294, D4S1579, D4S397, D4S3089, D4S2965, D4S192, D4S420, D4S1644, D4S3334, D4S3007, D4S394, D4S2983, D4S2923, D4S615, AFM$_\alpha$184za9, D4S2928, D4S1065, D4S1582, D4S107, D4S3009, D4S2906, D4S2949, AFM087zg5, D4S2944, D4S403, D4S2942, D4S2984, D4S1602, D4S1511, D4S2311, D4S3048, D11S133, D11S147, CD3D, D11S285, and D11S29. The markers are typically separated by 1, 2, 3, 4, or 5 centimorgans.

The bipolar affective disorder disease status of the family members may be affected or unaffected, or both. The bipolar affective disease status is assessed for the family members after the age of onset. Corresponding genotypes are determined so that at least one marker from within the same chromosomal region is used such that a basis of comparison at that chromosomal region is provided. Generally, markers from within two or three different chromosomal regions of the present invention are used so that the contribution of these same chromosomal regions can be determined. Using statistical methods well known to the skilled artisan, the genotypes of the family members are compared to determine if the chromosomal region is associated with the presence or absence of familial bipolar affective disorder. A lack of a statistically significant correlation between a form of a marker and a particular disease status may indicate that the particular chromosomal region identified by that marker does not contribute to the presence or absence of the disease. The method thereby allows one to exclude one, two, or all three chromosomal regions of the present invention from contributing to bipolar affective disorder in an affected family. The method may be applied effectively to family members from families where bipolar affective disorder is in part genetic, or wholly environmental.

The methods of the present invention may be performed on a wide variety of human cells including somatic cell hybrids, purified nuclei, chromosomal preparations or nucleic acid sequences comprising a marker to a chromosomal region of the present invention. The cells may be somatic or germline and from any time in gestation including fertilized embryo or preimplantation blastocysts. Preferably, somatic cells are employed to avoid the possibility of meiotic recombination events between a marker and locus associated with susceptibility to bipolar illness and to more readily allow determination of the genotype for a homologous chromosome pair.

The methods of the present invention may conveniently be practiced with informative markers which differ as to sequence or length such as RFLPs (restriction fragment length polymorphisms) and microsatellite markers such as STRPs (short tandem repeat polymorphisms) or VNTRs (variable number tandem repeats). However, other means to distinguish between the bipolar illness genotypes may be used, such as but not limited to, antigenicity, specificity, or activity of encoded proteins or fragments.

Isolation of nucleic acids from biological samples for use in the present invention may be carried out by a variety of means well known in the art. For example, see those described in Rothbart et al., 1989, in PCR Technology (Erlich ed., Stockton Press, New York) and Han et al., 1987, *Biochemistry*, 26:1617–1625. Kits are also commercially available for the extraction of high-molecular weight DNA for PCR. These kits include Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention. Prior to determining a bipolar illness genotype, the marker or marker which defines it may be amplified using such well known amplification means as the polymerase chain reaction (PCR) as described in U.S. Pat. Nos. 4,683,195; 4,683,202; and 4,965,188. In some case, the informative marker may be transcribed into RNA by the cells. In this instance, RNA may be used for amplification or for comparison between the tested individual and affected family member.

Of particular use in the present invention as applied to loci associated with susceptibility to BPAD are the following:

The primers 5'-CTCCAGCCTGGGTCACTA-3' (SEQ ID NO:1) and 5'-CTAATGCATGACAATAATATTTCCA-3' (SEQ ID NO:2) which amplify marker D6S344.

The clone p7H4 comprising a probe which, with the restriction enzyme EcoRV, can define a polymorphism of marker D6S7. Clone p7H4 may be obtained from the American Type Culture Collection (ATCC) as purified DNA with the accession number 57429, or as a plasmid in *E. coli* or phage lysate with the accession number 57428.

The primers 5'-ACCTAAGCGACTGCCTAAAC-3' (SEQ ID NO:3) and 5'-CTTGTTCATCTGCCTTGTGC-3' (SEQ ID NO:4) which amplify chromosome marker D6S89.

Also, primers 5'-AGTCTCATGTGACACAAGGCAG-3' (SEQ ID NO:5) and 5'-TGTAACCTGGAAGTAAGGCATG-3' (SEQ ID NO:6) which also amplify marker D6S89.

The primers 5'-TAGGGCCATCCATTCT-3' (SEQ ID NO:7) and 5'-CCTACCATTGACACTCTCAG-3' (SEQ ID NO:8) which amplify marker D13S171.

The clone p7F12 comprising a probe which identifies chromosome marker D13S1. Probe p7F12 is available from the ATCC as purified DNA using accession number 57007, or in plasmid in *E. coli* or phage lysate using accession number 57006. Polymorphisms can be defined using restriction enzymes MspI, TaqI, or BclI in conjunction with probe p7F12. A region spanning the marker can be amplified with the primers 7F12-Ia 5'-TGTAACTATTGGGAGGAAAGA-3' (SEQ ID NO:9) and 7F12-IIa 5'-TTGTGTAGGACTCTCTAGTTT-3' (SEQ ID NO:10).

The primers 5'-GATTTGAAAATGAGCAGTCC-3' (SEQ ID NO:11) and 5'-GTCGGGCACTACGTTTATCT-3' (SEQ ID NO:12) which amplify chromosome marker D13S218.

The probe inserted into clone pEFZ33 which defines an RFLP for chromosome marker D15S45 and is available from the ATCC in *E. coli* or a phage lysate using accession number 61006, or as purified DNA using accession number 61007.

The primers 5'-GCACCAACAACTTATCCCAA-3' (SEQ ID NO:13) and 5'-CCCTAAGGGGTCTCTGAAGA-3' (SEQ ID NO:14) which amplify chromosome marker D15S117.

Other probes and primers useful in the present invention are presented in Table I. See, e.g., Gyapay et al., "The 1993–1994 Genethon Human Genetic Linkage Map," *Nature Genet.* 7:246–249(1994).

TABLE 1

| Genethon ID No. | Distance to Next Marker (Centimorgans) | | | D-Number | EMBL GenBank No. | Primers 5'-3' (SEQ ID NO:) | |
|---|---|---|---|---|---|---|---|
| | Sex-Averaged | Female | Male | | | | |
| AFMa350zc9 | 1.4 | 2.5 | 0.1 | D6S1600 | Z52999 | AGCTTCTGTGCATGTGTGCA (15) | CAAAGTCCCAGCAGGTTC (16) |
| AFM092xb7 | 5.0 | 1.3 | 8.8 | D6S344 | Z17332 | CTCCAGCCTGGGTCACTA (1) | CTAATGCATGACAATAATATTTCCA (2) |
| AFM205ye1 | 0.0 | 0.0 | 0.0 | D15S123 | Z16923 | AGCTGAACCCAATGGACT (17) | TTTCATGCCACCAACAAA (18) |
| AFMa246wb5 | 0.0 | 0.0 | 0.0 | D15S982 | Z52695 | ATGTTTAAATTAATAACGTAACAGT (19) | GACTTCATCTGGATTCACAA (20) |
| AFM150xf4 | 0.0 | 0.0 | 0.0 | D15S119 | Z16673 | AACAGAAAATCCGTAACATAACATA (21) | ACTTTTGTGCCATTTAGAGATT (22) |
| AFM326vd9 | 0.0 | 0.0 | 0.0 | D15S1032 | Z51395 | AGCTTTAACTTCCATGAGTTTC (23) | CTAATCTCGTGCATAGTGA (24) |
| AFM310we1 | 0.0 | 0.0 | 0.0 | D15S208 | Z24290 | TCTTAGCAGTAATTGTCACTCCTT (25) | ACATACCATCCCATGGTTAT (26) |
| AFM261xb9 | 0.0 | 0.0 | 0.0 | D15S161 | Z23852 | TCTGTGATTTTGCCATTATGAG (27) | TAAACTGGAATTTTTGACTATGAGC (28) |
| AFM016yg1 | 0.0 | 0.0 | 0.0 | D15S143 | Z23284 | CTAAGGAGGCAACAGCAAAG (29) | ATGTAAAGACTGGTATCTGTAGCAC (30) |
| AFMb330xd5 | 0.0 | 0.0 | 0.0 | D15S1017 | Z53648 | TCAAGTAAGGCNATTATTATACAGA (31) | CCACAAGCTGGACTGAGAAT (32) |
| AFMa337ze1 | 0.0 | 0.0 | 0.0 | D15S990 | Z52918 | CTGAACAGGTTGAAGTGTCC (33) | CTTGGAATGCCTGAGGAC (34) |
| AFMb351yh1 | 0.0 | 0.0 | 0.0 | D15S1024 | Z53819 | CTAAGTCCTCCACACTAGCC (35) | CTAAAATGGAACAGGGC (36) |
| AFM359tf9 | 0.0 | 0.0 | 0.0 | D15S1039 | Z51531 | TGCCGTAGTAACATCTG (37) | CCAAGGATAAAGTATTTGTGTC (38) |
| AFMa345xh9 | 0.0 | 0.0 | 0.0 | D15S992 | Z52967 | AGCTGAGAAATGCCTTCTATAAAT (39) | GAGGGCCACCTTGATAGT (40) |
| AFMa231wb5 | 1.6 | 3.2 | 0.0 | D15S978 | Z52624 | AGCTTCATACACTGAAATTGTTG (41) | CACCGGAAACCTTGAT (42) |
| AFM218yf12 | 0.0 | 0.1 | 0.0 | D15S126 | Z16994 | GTGAGCCAAGATGGCACTAC (43) | GCCAGCAATAATGGGAAGTT (44) |
| AFMb076wc9 | 0.0 | 0.0 | 0.0 | D15S1003 | Z53278 | TGGTAGTACCCCTGGATACCTG (45) | AATCTTTGTGGATATGGCTCTGCT (46) |
| AFM189yc1 | 0.0 | 0.0 | 0.0 | D15S121 | Z16814 | TTGTATCAGGGATTTGGTTA (47) | TGTTGTCGCTTCAGTACATA (48) |
| AFMb324yh9 | 0.5 | 1.1 | 0.0 | D15S1016 | Z53609 | GATCCGTCACATAATGGC (49) | ACACCTCAGCTTTCCTGG (50) |
| AFM312wd1 | 0.0 | 0.0 | 0.0 | D15S209 | Z24319 | AAACATAGTGCTCTGGAGGC (51) | GGGCTAACAACAGTGTCTGC (52) |
| AFMa085wg1 | 0.0 | 0.0 | 0.0 | D15S1049 | Z51963 | CACTCCAGCCTAAGGAACAC (53) | TGTCAAAGATGGCTTTTATTACC (54) |
| AFM296wg5 | 0.0 | 0.1 | 0.0 | D15S1029 | Z51303 | AAGAGTAAAACTCCGTCACAAACAC (55) | AGATTTGAGTCTCTGCACAGTAAG (56) |
| AFMa106xg1 | 2.6 | 4.0 | 1.1 | D15S962 | Z52043 | AATTCTGCTCATTGGGG (57) | GGATATTTTGGAACTGCACT (58) |
| AFMb034yg5 | 0.6 | 0.0 | 0.0 | D15S998 | Z53169 | AAGCATCAAAGTGTAACTCCAGACC (59) | TTGGAGCCTGTGTATGTGTG (60) |
| AFM293ze9 | 0.0 | 1.4 | 0.0 | D15S1008 | Z53386 | GGTGCTGCCTCCTAACA (61) | CGAGCCCTTCTGAAACA (62) |
| AFM165xc7 | 0.0 | 0.0 | 0.0 | D15S150 | Z51073 | CTGTATGGCCTCAGTCTCGG (63) | AGCTCTGTGCGGAAGTCCCT (64) |
| AFM098yg1 | 0.0 | 0.0 | 0.0 | D15S117 | Z16568 | GCACCAACAACTTATCCCAA (13) | CCCTAAGGGGTCTCTGAAGA (14) |

Of particular use in the present invention as applied to loci found on human chromosome 4p that are associated with resistance to BPAD are the following:

The primers 5'-AGGCATACTAGGCCGTATT-3' (SEQ ID NO:65) and 5'-TTCCCATCAGCGTCTTC-3' (SEQ ID NO:66), which amplify chromosome markers D4S431 and D4S2366;

The primers 5'-GCTCACAGAAGTGCCCAATA-3' (SEQ ID NO:67) and 5'-CCCTGGGTGAAGTTTAATCTC-3' (SEQ ID NO:68), which amplify chromosome marker D4S2935;

The primers 5'-ATTTTTGCTACATTGGTGACATA-3' (SEQ ID NO:69) and 5'-CTTCAGGTTCTACTAGT-TCATGG-3' (SEQ ID NO:70), which amplify chromosome marker D4S3007;

The primers 5'-CCCTTGAGCATCCTGACTTC-3' (SEQ ID NO:71) and 5'-GAGTGAGCCCCTGTACTCCA-3' (SEQ ID NO:72), which amplify chromosome marker D4S394;

The primers 5'-ATCAGGGTTCTCCACACAAA-3' (SEQ ID NO:73) and 5'-TTGGTTGAAACTTGTG-GATATAAA-3' (SEQ ID NO:74), which amplify chromosome marker D4S1582;

The primers 5'-CATTCTAGTAGTTATATTGGCT-TATCC-3' (SEQ ID NO:75) and 5'-CAGTTGCTTGATAC-CTATATTTTC-3' (SEQ ID NO:76), which amplify chromosome marker D4S1605;

The primers 5'-CCTTACGGATAGGGGCAG-3' (SEQ ID NO:77) and 5'-CTAATGTCCAGGTCTACGGC-3' (SEQ ID NO:78), which amplify chromosome marker D4S2949; and The primers 5'-AGGTGGCCCTGAGTAGGAGT-3' (SEQ ID NO:79) and 5'-TTTGAGGGAATGATTTGGGT-3' (SEQ ID NO:80), which amplify chromosome marker D4S403. These and additional markers are shown in Table 2.

Of particular use for detecting markers that are associated with resistance to BPAD and are found on chromosome arm 4q are the following:

The primers 5'-AATGCTTATCTACCAATGAGTG-3' (SEQ ID NO:81) and 5'-GTGGCTGGGTAGTATTCATGG-3' (SEQ ID NO:82), which amplify chromosome marker D4S2423;

The primers 5'-GGCAAGANTCCGTCTCAA-3' (SEQ ID NO:83) and 5'-TGAAGTAAATTTGGGAGATTGT-3' (SEQ ID NO:84), which amplify chromosome marker D4S422;

The primers 5'-AGGGAGGTCATCAGTTCATT-3' (SEQ ID NO:85) and 5'-TGTTGCAAACTTTGCTTTTC-3' (SEQ ID NO:86), which amplify chromosome marker D4S397;

The primers 5'-TTCTTTGATTCTTCGGGG-3' (SEQ ID NO:87) and 5'-TTTCTCAGCAACATTCCTCT-3' (SEQ ID NO:88), which amplify chromosome marker D4S420;

The primers 5'-TAACATTGACCGCTCCTCTC-3' (SEQ ID NO:89) and 5'-CATCCTTCCTGGTCCCTAGT-3' (SEQ ID NO:90), which amplify chromosome marker D4S1644;

The primers 5'-TAAAACTTCTGAATGAAAAG-3' (SEQ ID NO:91) and 5'-GTAGGGAGGAATAGTTAG-3' (SEQ ID NO:92), which amplify chromosome marker UT2147;

The primers 5'-TGCAAACTGTCACTCAAAAG-3' (SEQ ID NO:93) and 5'-GCCAAGGCTGATCCTC-3' (SEQ ID NO:94), which amplify chromosome marker D4S1565;

The primers 5'-GCGCTCTTGGTATATGGTACAG-3' (SEQ ID NO:95) and 5'-TGTGGGCAACGTCACTC-3' (SEQ ID NO:96), which amplify chromosome marker D4S424; and The primers 5'-GACTCCAAATCACATGAGCC-3' (SEQ ID NO:97) and 5'-GTCTCTGCATTTGCTGGTTT-3' (SEQ ID NO:98), which amplify chromosome marker D4S1625. These and additional primers that are useful for amplifying chromosomal markers that identify chromosomal regions associated with increased resistance to BPAD are shown in Table 3.

Figure 9:
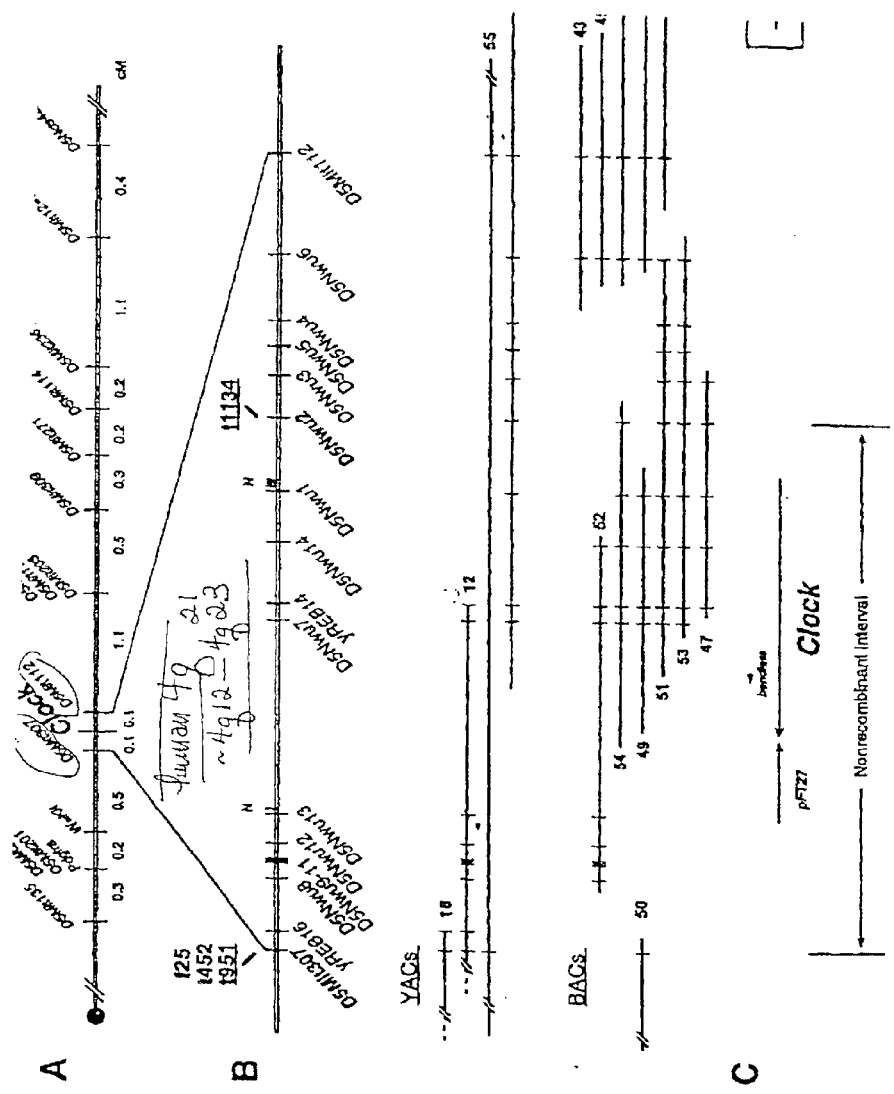
FIG. 9A shows the location of the mouse Clock gene on a genetic map chromosome 5 (King et al., Cell 89: 641–653 (1997)).
FIG. 9B shows an physical map of the mouse chromosome 5 region immediately surrounding Clock. Shown in FIG. 9C is the transcription unit map of the Clock locus. The locations of the homologous region in human, which is found on chromosome 4, are indicated.

Significantly, the chromosomal region of human chromosome 4q which is associated with increased resistance to BPAD includes the human homolog of the mouse Clock gene (FIG. 9A). Certain alleles of this gene, which is involved in circadian rhythms, are implicated by the findings reported herein as being involved in mediating resistance to BPAD. Accordingly, the present invention provides methods of determining a genotype associated with increased or decreased resistance to familial bipolar affective disorder by determining the genotype of an individual using at least one marker for at least one chromosomal region linked to the human Clock gene. The chromosomal regions are inclusive of and localized between D4S402 and D4S1625. From the genotype, increased or decreased resistance to bipolar affective disorder is determined.

The chromosome markers disclosed may be modified by insertions, deletions, substitutions, or additions with the proviso that modified sequence be sufficiently complementary to identify the same chromosomal markers as the unmodified sequences. As will be recognized by those of skill, the complementary sequences of the probes and primers may likewise be employed or modified.

TABLE 2

| combined | female | male | allele | forward primer 1p1 | Reverse primer rp1 | locus | name | date-start |
|---|---|---|---|---|---|---|---|---|
| | | | | CTCAAGAGAAATAGAACCAAT (SEQ ID NO:99) | AGACGGAAACCAAATGGA (SEQ ID NO:100) | GATA145E01 | | |
| 1.3 | 2.7 | 0 | 7 | actctqaaggctgagatggg (SEQ ID NO:101) | ctgaaccgcagatcccc (SEQ ID NO:102) | D4S432 | | |
| 0 | 0 | 0 | 3 | tcagaaacccctacaggaaa (SEQ ID NO:103) | tttgatgagttattcggagg (SEQ ID NO:104) | D4S2925 | | |
| 4.1 | 2.2 | 6.2 | 7 | acctcactggaaactaaatgg (SEQ ID NO:105) | tgaacagcagcggtgt (SEQ ID NO:106) | D4S3023 | | |
| 1.4 | 0 | 1.9 | 10 | aggcatactaggcctalt (SEQ ID NO:65) | ttcccatcagcgtcttc (SEQ ID NO:66) | D4S431 | Hamisha | September 1996 |
| | | | | | | D4S2366 | Brian | Apr. 7, 1997 |

TABLE 2-continued

| | | | | | | | |
|---|---|---|---|---|---|---|---|
| 0.1 | 1.6 | 1.6 | 6 | gctcacagaagtgcccaala (SEQ ID NO:67) | ccctgggtgaagtttaatctc (SEQ ID NO:68) | D4S2935 | Melissa November 1996 |
| 2.2 | 2.2 | 0 | 3 | atttttgctacattggtgacata (SEQ ID NO:69) | cttcaggttctactagttcatgg (SEQ ID NO:78) | D4S3007 | Melissa November 1996 |
| 1.6 | 3.7 | 0 | 8 | cccttgagcatcctgacttc (SEQ ID NO:71) | gagtgagccsctgtactcca (SEQ ID NO:72) | D4S394 | Sharon November 1996 |
| 0 | 0 | 0 | 4 | gggcatcatgtctgcaa (SEQ ID NO:107) | aggttccctgaatgttcg (SEQ ID NO:108) | D4S2923 | |
| 5.8 | 8.3 | 3.3 | 13 | tgtccagttggcaggg (SEQ ID NO:109) | ggtcgcattcattcgc (SEQ ID NO:110) | D4S2983 | optimized |
| 0.1 | 0 | 0 | 9 | atggcctgtgaatcaaccc (SEQ ID NO:111) | aatcctttgaagacggccc (SEQ ID NO:112) | D4S3009 | |
| 0 | 0 | 0 | 6 | atcagggttctccacacaaa (SEQ ID NO:73) | ttggttgaaacttgtggalataaa (SEQ ID NO:74) | D4S1582 | Hamisha September 1996 |
| 0 | 0 | 0 | 7 | atagacgtgttcctggtgg (SEQ ID NO:113) | ctcaggctatttatggggtg (SEQ ID NO:114) | D4S2928 | |
| 0 | 0 | 0 | 4 | cattctagtagttatcggcttatcc (SEQ ID NO:75) | cagttgcttgatacctatatttttc (SEQ ID NO:76) | D4S1605 | TOSS |
| 1.1 | 1.1 | 1.1 | 7 | ccttaaaagtatccagtaaagcaca (SEQ ID NO:115) | caaggttgtcctgtgtctgc (SEQ ID NO:116) | D4S1599 | Melissa November 1996 |
| 0 | 0 | 0 | 6 | cagtctagattcaaaggaattagac (SEQ ID NO:117) | aattagagatgcccgtgaaa (SEQ ID NO:118) | D4S2906 | |
| 0 | 0 | 0 | 7 | agcttcttgctgtgtcc (SEQ ID NO:119) | aagggtggggctctat (SEQ ID NO:120) | D4S3036 | |
| 1.2 | 1.1 | 1.1 | 6 | ccttacggatagggggcag (SEQ ID NO:77) | ctaatgtccaggtctacggc (SEQ ID NO:78) | D4S2949 | Hamisha September 1996 |
| 0.4 | 1.1 | 0 | 6 | agattctggcctccttgc (SEQ ID NO:121) | cctggtgaagtggtggg (SEQ ID NO:122) | D4S2944 | |
| 0.1 | 0 | 0 | 7 | caaatgcccatcaatcaac (SEQ ID NO:123) | gggtccagtctcatccac (SEQ ID NO:124) | D4S2942 | |
| 0.1 | 0 | 0 | 6 | ccagatgggttccaaatga (SEQ ID NO:125) | tgtggactgagtagagagtgcc (SEQ ID NO:126) | D4S1602 | |
| 0 | 0 | 0 | 5 | cccaaaggaatcagatg (SEQ ID NO:127) | gatcttgaaattttcccatttt (SEQ ID NO:128) | D4S2984 | |
| 3.3 | 1.1 | 5.4 | 7 | aggtggccctgagtaggagt (SEQ ID NO:79) | tttgagggaatgatttgggt (SEQ ID NO:80) | D4S403 | |
| | | | | agcccaggaggtgaag (SEQ ID NO:129) | gagatttctaggaaacattgag (SEQ ID NO:130) | D4S1564 | |
| | | | | agagtagttbccatcttgttttc (SEQ ID NO:131) | gggcaaggctcatcac (SEQ ID NO:132) | D4S1611 | |
| | | | | acatggagaatcttttagtagca (SEQ ID NO:133) | cttttgagataccctatcagt (SEQ ID NO:134) | D4S1573 | |
| | | | | ggacctccttgcttcg (SEQ ID NO:135) | cccttaggttgcttgt (SEQ ID NO:136) | D4S427 | Cary |
| | | | | TTTAGTTGAATGGCTGAGTGG (SEQ ID NO:137) | TGAGCCAATTCCCCTAATAA (SEQ ID NO:138) | GATA30B11 | |
| | | | | CCACAAAGACAGAATCAATAG (SEQ ID NO:139) | TCTCAACCTCCATAACTGTG (SEQ ID NO:140) | UT7161 | |
| | | | | TTTGATTTCCTGCAGTrGGT (SEQ ID NO:141) | TCAACACAAAACCAATGTGG (SEQ ID NO:142) | ATA26F08 | |
| | | | | ttacactgaagaatgtgagagcc (SEQ ID NO:143) | ggccttggaactactgatgg (SEQ ID NO:144) | D4S2985 | |
| | | | | ccttgggtcagccacatatc (SEQ ID NO:145) | cactcagaacagaaacttgggt (SEQ ID NO:146) | D4S1615 | |
| | | | | ACTGGTATGTCCTAACCCCC (SEQ ID NO:147) | GATCTGCAGTTGGATTCTGG (SEQ ID NO:148) | ATA26B08 | |
| | | | | GCTGCACCTTAGACTAGAT (SEQ ID NO:149) | TTAGTAGCTTCTCAGCAGC (SEQ ID NO:150) | UT6123 | |
| | | | | CAGACATAAATGAAAGAAAAG (SEQ ID NO:151) | GGCAGCAAACTATGGTATGTAA (SEQ ID NO:152) | UT723 | |
| | | | | AAGTTAATCCATGTGCCGTG (SEQ ID NO:153) | CTTCTTTCTCTTTTTTCCCTG (SEQ ID NO:154) | UT1376 | |
| | | | | ggtgatccacctgcct (SEQ ID NO:155) | aagccactgaccttcact (SEQ ID NO:156) | D4S429 | |
| 0 | 0 | 0 | 8 | gacagcctattgtagtaacttgtgg (SEQ ID NO:157) | tagtcagggtgctctagggg (SEQ ID NO:158) | D4S3039 | |

TABLE 3

| | | | | | | | | |
|---|---|---|---|---|---|---|---|---|
| 0 | 0 | 0 | 3 | atgggtacttttttgaatcacatcc (SEQ ID NO:159) | acactccagcctccctgac (SEQ ID NO:160) | D4S1575 | | |
| 2.6 | 5.5 | 0 | 7 | agcttccatggtcattaagagt (SEQ ID NO:161) | tagggtcctccaaagaacaga (SEQ ID NO:162) | D4S2959 | Maria | Apr. 7, 1997 |
| | | | | AATGCTTATCTACCAATGAGTG (SEQ ID NO:81) | GTGGCTGGGTAGTATTCATGG (SEQ ID NO:82) | D4S2423 | Cary | Jun. 1, 1997 |
| 0.1 | .1 | 0 | 8 | ggcaagantccgtctcaa (SEQ ID NO:83) | tgaagtaaaatttgggagattgt (SEQ ID NO:84) | D4S422 | Hamisha | Mar. 15, 1997 |
| 5.2 | 7.1 | 3.3 | 7 | attgtncatatatcatcacctgg (SEQ ID NO:163) | acagcataaactaaaatttggggg (SEQ ID NO:164) | D4S1576 | Sharon | November 1996 |
| 0 | 0 | 0 | 7 | agctactcaggnaggctg (SEQ ID NO:165) | ttttttaatatccaacctcacttgtg (SEQ ID NO:166) | D4S2972 | Cary | Jun. 1, 1997 |
| 0 | 0 | 0 | 9 | cccccaccttcctgac (SEQ ID NO:167) | ctggagcatccgtgtg (SEQ ID NO:168) | D4S1579 | | |
| 1.6 | 2.2 | 0 | 8 | agggaggtcatcagttcatt (SEQ ID NO:85) | tgttgcaaacttttgcttttc (SEQ ID NO:86) | D4S397 | | |
| | | | | TCGATCTGCAGTTGCCCTA (SEQ ID NO:169) | TGTACCCATTAAGCAGCCTG (SEQ ID NO:170) | UT1264 | | |
| 0 | 0 | 1 | 10 | tttcccacctggccttat (SEQ ID NO:171) | ctcttgaagccctgaagttt (SEQ ID NO:172) | D4S2939 | Melissa | November 1996 |
| 0.6 | 1.2 | 0 | 6 | tttacagttttcaaaattttc (SEQ ID NO:173) | ggttcttgaccctagctcc (SEQ ID NO:174) | D4S2965 | | |
| 1.1 | 1.1 | 1.1 | 7 | ttctttgattcttcggggg (SEQ ID NO:87) | tttctcagcaacattcctct (SEQ ID NO:88) | D4S420 | Melissa | November 1996 |
| | | | | TAACATTGACCGCTCCTCTC (SEQ ID NO:89) | CATCCTTCCTGGTCCCTAGT (SEQ ID NO:90) | D4S1644 | Melissa | Feb. 28, 1997 |
| | | | | TAAAACTTCTGAATGAAAAG (SEQ ID NO:91) | GTAGGGAGGAATAGTTAG (SEQ ID NO:92) | UT2147 | Ashima | Apr. 7, 1997 |
| 0.7 | 2.2 | 0 | 7 | tgcaaatcgtcactcaaaag (SEQ ID NO:93) | gccaaggctgatcctc (SEQ ID NO:94) | D4S1565 | Sharon | November 1996 |
| | | | | GGCCAACAGAGCAGGATC (SEQ ID NO:175) | GCCAAGAGAGTGAGACTCCA (SEQ ID NO:176) | GATA135E06 | Melissa | Feb. 28, 1997 |
| 1.5 | 0 | 2.2 | 8 | gcgctcttggtatatggtacag (SEQ ID NO:95) | tgtgggcaacgtcactc (SEQ ID NO:96) | D4S424 | optimized | |
| 0 | 0 | 0 | 7 | ggttatttaattttagtaacgcatc (SEQ ID NO:177) | gaacagaagtgctggagac (SEQ ID NO:178) | D4S2981 | Ashima | Apr. 7, 1997 |
| | | | | GACTCCAAATCACATGAGCC (SEQ ID NO:97) | GTCTCTGCATTTGCTGGTTT (SEQ ID NO:98) | D4S1625 | Ashima | Apr. 7, 1997 |
| 0 | 0 | 0 | 4 | tcgtgcccagccaagt (SEQ ID NO:179) | ttgctcacaggattgcttct (SEQ ID NO:180) | D4S1604 | | |
| | | | | attttcatgcattcgttagaatttt (SEQ ID NO:181) | tctaggtgatggtgatgctg (SEQ ID NO:182) | D4S1561 | | |
| | | | | gcatgtaccattgccagg (SEQ ID NO:183) | cccagagtgctgatgtgtg (SEQ ID NO:184) | D4S1586 | Cary | Jun. 1, 1997 |
| | | | | aaagttccaatctcccc (SEQ ID NO:185) | tcttatgctgcaatcactg (SEQ ID NO:186) | D4S1549 | | |
| | | | | tgccataaacaaggtgaaac (SEQ ID NO:187) | ttacccaactgctacaccat (SEQ ID NO:188) | D4S1548 | | |
| | | | | TTCAATACTCCTGTATCACAAAG (SEQ ID NO:189) | TGAGACACAATCTGAGCTATGC (SEQ ID NO:190) | GATA72A08 | Cary | Jun. 1, 1997 |
| | | | | TGGTTCTGCTTTTTCTCTCC (SEQ ID NO:191) | TTTAACAGACAAATGACAAATG (SEQ ID NO:192) | GATA8A05 | | |
| 1.4 | 2.5 | 0.1 | 8 | agcttgtgcatgtgtgca (SEQ ID NO:15) | caaagtcccagcaggttc (SEQ ID NO:16) | D6S1600 | | |
| 5 | 1.3 | 8.8 | 9 | ctccagcctgggtcacta (SEQ ID NO:1) | ctaatgcatgacaataatatttcca (SEQ ID NO:2) | D6S344 | optimized | |
| 0 | 0.4 | 0.1 | 15 | aatcactgttacccatagggttatc (SEQ ID NO:193) | aggccaagacctctgtgc (SEQ ID NO:194) | D6S1713 | optimized | |
| 2.2 | 1.8 | 2.2 | 15 | tgcaaaacaggcaoacatac (SEQ ID NO:195) | ttaatcaattttctgcaaagataaa (SEQ ID NO:196) | D6S1617 | optimized | |
| 0 | 0.1 | 0.1 | 9 | gtatagccaactgcttccaa (SEQ ID NO:197) | gggtnccatttattgagatt (SEQ ID NO:198) | D6S1668 | Melissa | Feb. 28, 1997 |
| 0 | 0.1 | 0.1 | 7 | tgtttcagcagcataggg (SEQ ID NO:199) | agagcctgtttggtgtcatc (SEQ ID NO:200) | D6S1591 | | |
| 0 | 0.1 | 0.1 | 6 | gtttccaagggctggg (SEQ ID NO:201) | gaaatcaaaataacacatcctctg (SEQ ID NO:202) | D6S1677 | | |
| 0.1 | 0.1 | 0.1 | 3 | tacactaatggctctcctgg (SEQ ID NO:203) | gccagatttctctgctgtag (SEQ ID NO:204) | D6S1685 | optimized | |

TABLE 3-continued

| | | | | | | | | |
|---|---|---|---|---|---|---|---|---|
| 2.7 | 4.3 | 1.1 | 12 | aagaacttcccaaaccaat (SEQ ID NO:205) | aaccatccaggacatcaa (SEQ ID NO:206) | D6S1574 | Maria | Apr. 7, 1997 |
| 0 | 0.1 | 0.1 | 4 | tcaaggctttctgaggc (SEQ ID NO:207) | agcatggattctgttgtttg (SEQ ID NO:208) | D6S1S98 | | |
| 0.7 | 1.1 | 0.1 | 7 | agccaggcatgctaacat (SEQ ID NO:209) | ggattacaggcacccagta (SEQ ID NO:210) | D6S1640 | optimized | |
| 1.5 | 1.1 | 2.2 | 8 | ccttgagcaccttaaatttt (SEQ ID NO:211) | taactgacaaagcagaatagca (SEQ ID NO:212) | D6S1547 | optimized | |
| 0 | 0.1 | 0.1 | 11 | ccttaaacaaacaataagacc acc (SEQ ID NO:213) | cagcctagaaaacagagcca (SEQ ID NO:214) | D6S1674 | | |

| | | | | | |
|---|---|---|---|---|---|
| 13 | 174–190 | 5 | GAGGTTGCTTGAAATCCAG (SEQ ID NO:215) | GAATCTCATCTACCCTGTTTGG (SEQ ID NO:216) | GATA161F06 |
| 13 | 189–205 | 0.63 | ATACTCCGAGCTATCTGTCTACC (SEQ ID NO:217) | GGTGCAGATCATGACCTCTC (SEQ ID NO:218) | GATA21F07 |
| 13 | 148–168 | 0.77 | CATGGATGCAGAATTCACAG (SEQ ID NO:219) | TCATCTCCCTGTTTGGTAGC (SEQ ID NO:220) | GATA51B02 |
| 13 | 178–210 | 0.87 | GGTTTGCTGGCATCTGTATT (SEQ ID NO:221) | TGTCTGGAGGCTTTTCAGTC (SEQ ID NO:222) | GATA53C06 |
| 13 | 223–243 | 0.8 | ACCTGTTGTATGGCAGCAGT (SEQ ID NO:223) | GGTTGACTCTTTCCCCAACT (SEQ ID NO:224) | GGAA29H03 |
| 13 | 177–193 | 0.75 | GTCTGTCCATCCATTCATCC (SEQ ID NO:225) | CCTCTTCTCCATGAGGACCT (SEQ ID NO:226) | GGAT12E07 |
| 13 | 213 | 6 | ACTTAAATGTCCATCAATAAAT (SEQ ID NO:227) | TGATTGGCTTTTTTTACTTAC (SEQ ID NO:228) | UT1213 |
| 13 | 213 | 7 | TGAACTCCGGCCTGGGTGA (SEQ ID NO:229) | TTTTGGAGCTGGGGATGTC (SEQ ID NO:230) | UT1585 |
| 4 | 235–259 | 0.81 | ACTGGTATGTCCTAACCCCC (SEQ ID NO:147) | GATCTGCAGTTGGATTCTGG (SEQ ID NO:148) | ATA26B08 |
| 4 | 222–234 | 0.87 | TTTGATTTCCTGCAGTTGGT (SEQ ID NO:141) | TCAACACAAAACCAATGTGG (SEQ ID NO:142) | ATA26F08 |
| 4 | 245–271 | 9 | tgccataaacaaggtgaaac (SEQ ID NO:187) | ttacccaactgctacaccat (SEQ ID NO:188) | D4S1548 |
| 4 | 203–217 | 6 | aaagttccaatctcccc (SEQ ID NO:185) | tcttatgctgcaatcactg (SEQ ID NO:186) | D4S1549 |
| 4 | 294–306 | 7 | attttcatgcattcgttagaatttt (SEQ ID NO:181) | tctaggtgatggtgatgctg (SEQ ID NO:182) | D4S1561 |
| 4 | 220–242 | 12 | agcccaggaggtgaag (SEQ ID NO:129) | gagatttctaggaaacattgag (SEQ ID NO:130) | D4S1564 |
| 4 | 101–113 | 5 | acatggagaatcttttagtagca (SEQ ID NO:133) | cttttgagataccctatcagt (SEQ ID NO:134) | D4S1573 |
| 4 | 103–117 | 7 | gcatgtaccattgccagg (SEQ ID NO:183) | cccagagtgctgatgtgtg (SEQ ID NO:184) | D4S1S86 |
| 4 | 222–233 | 6 | ccagatgggttccaaatga (SEQ ID NO:125) | tgtggactgagtagagagtgcc (SEQ ID NO:126) | D4S1602 |
| 4 | 277–285 | 5 | agagtagtttccatctttgttttc (SEQ ID NO:131) | gggcaaggctcatcac (SEQ ID NO:132) | D4S1611 |
| 4 | 115–125 | 5 | ccttgggtcagccacatatc (SEQ ID NO:145) | cactcagaacagaaacttgggt (SEQ ID NO:146) | D4S1615 |
| 4 | 248–262 | 8 | ttacactgaagaatgtgagagcc (SEQ ID NO:143) | ggccttggaactactgatgg (SEQ ID NO:144) | D4S2985 |
| 4 | 75–97 | 8 | ggcaagantccgtctcaa (SEQ ID NO:83) | tgaagtaaaatttgggagattgt (SEQ ID NO:84) | D4S422 |
| 4 | 178–192 | 8 | gcgctcttggtatatggtacag (SEQ ID NO:95) | tgtgggcaacgtcactc (SEQ ID NO:96) | D4S424 |
| 4 | 142–166 | 10 | ggacctccttgcttcg (SEQ ID NO:135) | cccttaggttgcttgt (SEQ ID NO:136) | D4S427 |
| 4 | 193–207 | 8 | ggtgatccacctgcct (SEQ ID NO:155) | aagccactgaccttcact (SEQ ID NO:156) | D4S429 |
| 4 | 161–229 | 11 | CTCAAGAGAAATAGAACCAATAA (SEQ ID NO:99) | TAAGACGGAAACCAAATGGA (SEQ ID NO:100) | GATA145E01 |
| 4 | 289–305 | 0.8 | TTTAGTTGAATGGCTGAGTGG (SEQ ID NO:137) | TGAGCCAATTCCCCTAATAA (SEQ ID NO:138) | GATA30B11 |
| 4 | 202–218 | 5 | TTCAATACTCCTGTATCACAAAG (SEQ ID NO:189) | TGAGACACAATCTGAGCTATGG (SEQ ID NO:190) | GATA72A088 |
| 4 | 151 | 0.68 | TGGTTCTGCTTTTTCTCTCC (SEQ ID NO:191) | TTTAACAGACAAATGACAAATCT (SEQ ID NO:192) | GATA8A05 |
| 4 | 249 | 10 | CCTCAGTTTTCTCTCCTGC (SEQ ID NO:231) | TGCTGCTATATGCTTTGCAG (SEQ ID NO:232) | UT1508 |
| 4 | 338 | 4 | TGGGTGACAGAGCTAGTCC (SEQ ID NO:233) | GAACCAGCCTCGCATACC (SEQ ID NO:234) | UT2021 |
| 4 | 291 | 7 | GCTGCACCTTAGACTAGAT (SEQ ID NO:149) | TTAGTAGCTTCTCAGCAGC (SEQ ID NO:150) | UT6123 |
| 4 | <361 | 6 | CCACAAAGACAGAATCAATAG (SEQ ID NO:139) | TCTCAACCTCCATAACTGTG (SEQ ID NO:140) | UT7161 |
| 4 | <314 | 5 | TTGCAGTGAGAAGAGATTGT (SEQ ID NO:235) | GCACAAGAATCAGATAAGGA (SEQ ID NO:236) | UT7738 |

TABLE 3-continued

| 4 | 206 | 6 | ACCCTGTACTTGTCAAGGTT<br>(SEQ ID NO:237) | AATCATGTGAACCAGTTTCC<br>(SEQ ID NO:238) | UT7739 |
| 4 | 290 | 7 | TGGTGGGTCTGCGTGTGTG<br>(SEQ ID NO:239) | TGCTGGGATTCGGTGCA<br>(SEQ ID NO:240) | UT7953 |

The primer pairs for chromosomal markers are also conveniently used as probes for the markers. Additional target regions may be identified by walking from known chromosome markers as described above. Techniques for chromosome walking are well known in the art as described in Sambrook et al., *Molecular Cloning, A Laboratory Manual*, Cold Spring Harbor Press, 1989. Vectors which are optimized for chromosome walking are commercially available (e.g., λDASH and λFIX (Stratagene Cloning Systems, La Jolla, Calif.). New markers may result from physical mapping of the interval defined by markers D6S34 and D6S89, D13S171 and D13S218. Markers D6S7 and D13S1 could serve as convenient focal points for mapping of the intervals. Regions proximal to D15S45 may also be used to identify new markers. Those of skill in the art will appreciate that a variety of methods to identify new markers may be employed. For example, the chromosomal regions of the present invention cloned into a yeast artificial chromosome (YAC) library can be identified and isolated by identifying the presence of sequences corresponding to the marker sequences identified above. Cosmid subclones can be created to provide more detailed physical maps; and AC repetitive hybridization probes could identify additional microsatellite sequences in the cloned regions. Other chromosome markers could be used to extend the physical map beyond the boundaries of the identified markers to yield other markers.

Generally, the markers of the present invention will yield directly or indirectly (e.g., upon treatment of a RFLP with a restriction enzyme) at least two distinct bipolar illness genotypes since one bipolar illness genotype will have been inherited from each parent. In some cases, however, only one genotype may result if the tested individual received identical forms of the genotype from both parents. In such cases, informative markers providing distinct genotypes may be used. The sizes of the markers of the tested individual are determined for comparison to the size of the markers of the affected family member. Equivalence in size between informative markers for the affected family member and tested individual indicates the same genotype as defined by that marker. Differences in size between informative markers for the affected family member indicates different genotypes as defined by that marker. As will be understood by the skilled artisan, construction of the pedigree is performed using the methods of the present invention to follow the transmission of genotypes associated or not associated with bipolar illness as defined by psychological diagnostic criteria.

Generally, the sizes will be determined by standard gel electrophoresis techniques as described in Sambrook et al., *Molecular Cloning, A Laboratory Manual*, Cold Spring Harbor Press, 1989, and Polymeropoulos et al., *Genomics*, 12:492–496 (1992). Polyacrylamide gel electrophoresis is particularly preferred because of its capability of high discrimination. Generally, autoradiography is employed to simultaneously visualize and identify the markers. Amplification of markers is generally performed with labelled nucleotide bases that provide a means for identifying the markers following the procedure. Alternatively, labelled nucleic acid primers may employed as labelling probes which can hybridize to the amplified markers. Typical autoradiographic labels include $^{32}P$, $^{14}C$, $^{3}H$, $^{125}I$, $^{35}S$, or the like. Alternatively, probes may be labelled with visual labels such as photoluminescents, Texas red, rhodamine and its derivatives, red leuco dye and 3,3'5,5'-tetramethylbenzidine (TMB), fluorescein and its derivatives, dansyl, umbelliferone and the like or with horse radish peroxidase, alkaline phosphatase, or the like.

Although the present invention has been described in some detail by way of illustration and example for purposes of clarity of understanding, it will be obvious that certain changes and modifications may be practiced within the scope of the appended claims.

EXAMPLE I

This Example describes the collection of epidemiologic data from pedigree members.

The genetic-epidemiologic study of bipolar affective disorders among the Old Order Amish in southeastern Pennsylvania has been previously described (Egeland et al., *Am. J. Psychiat.*, 140:56–61 (1983), Egeland, *Genetic Studies in Affective Disorders*, eds. Papolos & Lachman, 70–90 (John Wiley & Sons, N.Y. (1994)). FIG. 1 shows that the ancestral line encompasses the earliest cases of recurrent, psychiatric illness and the first confirmed cases of bipolar affective disorder. Bipolar I disorder among descendants of other pioneers usually occurred after intermarriage with the BP progenitor line. (Egeland, *Genetic Studies in Affective Disorders*, eds. Papolos & Lachman, 70–90 (John Wiley & Sons, N.Y. (1994)). On the extreme left side of the figure, one observes the LEFT extension coupled with the CORE Pedigree 110 which provided the resource first used to report genetic linkage data (Egeland et al., *Nature* 325:783–787 (1987)). After follow-up and addition of a RIGHT extension to Pedigree 110, further genetic analyses were reported in 1989 (Kelsoe et al., *Nature*, 342:238–243 (1989). Next, Pedigree 210 and partial Pedigree 310 (NIGMS Family 1075) (Egeland, NIGMS Human Genetic Mutant Cell Repository, NIH Publication 94-2011, 408–428, 992–999 (1994)) became a second large lateral extension (Pauls et al., *Genomics*, 11:730–736 (1991)). The present report utilizes all of these earlier subjects plus additional expansions, especially in Pedigree 310. The diagnoses for the 207 individuals in our current linkage study are summarized in Table 2. These Old Order Amish kinships continue to provide for lateral and lineal expansion and have evolved into the IX–Xth generations of descendants at risk.

Case ascertainment for mental illness among the Amish began with a community-wide network of informants and institutional rosters reviewed with informed consent (Hostetter et al., *Am. J. Psychiat.*, 140:62–66 (1983)). Over 400 patient cases have been ascertained. A psychiatric review board composed (since 1976) of Drs. James N. Sussex, Abram M. Hostetter, John J. Schwab, David R. Offord and Jean Endicott used both psychiatric interviews (Endicott et al., *Arch. Gen. Psychiat.*, 35:837–844 (1978)) and abstracted medical records to perform diagnostic assessments based on strict Research Diagnostic Criteria (RDC) (Spitzer et al., *Arch. Gen. Psychiat.*, 35:773–782 (1978)). Assessments by this review board were made blind to pedigree membership, diagnostic opinions and treatment information in the medical records, and genetic marker status. As the Board's diagnostic procedures yielded confirmed cases of BPI affective disorder, the immediate families of these patients were evaluated for psychopathology. Pedigree 110 was selected (1981) for initial genetic linkage study because of relationships between nuclear families, based on BPI probands, and illness spanning several generations (Egeland, Genetic Studies in Affective Disorders, eds. Papolos & Lachman 70–90, John Wiley & Sons, N.Y., (1994)). When one examines the relative risk for individuals used in this linkage study, there is a very high prevalence of affective disorder, with age-corrected morbid risk rates for BPI, BPII, and MDD (major depressive disorder) of 17%, 4%, and 6%, respectively. This gives an overall rate of 27% for major affective disorder in these pedigrees. The present sample, which includes extensions to the original family (FIG. 1) totals 207 members, with 31 diagnosed BPI, 50 with other psychiatric diagnoses (Dx), and 126 unaffected individuals (Table 4).

illness (not one case of schizophrenia occurs in the pedigrees used for linkage analyses) with bipolar disorder being the predominant diagnosis. The rigorous longitudinal assessment of these Amish pedigrees combined with the systematic and blind psychiatric evaluations and diagnoses should also greatly reduce the number of misdiagnoses included in the linkage analyses. Moreover, the restricted gene pool characteristic of this relatively closed population should reduce the number of disease-causing alleles, minimizing the problem of genetic heterogeneity.

EXAMPLE II

This Example describes the collection and analysis of genotypic data.

Genotypic data were collected for 551 DNA markers (RFLP and microsatellite) from 207 pedigree members, including 31 cases of confirmed BPI disorder. Blood samples were collected with informed consent and lymphoblastoid cell lines were established at the Coriell Institute of Medical Research and/or the National Institute of Mental Health. The NIGMS Human Genetic Mutant Cell Repository catalog contains updated pedigree and diagnostic information (Egeland, *NIGMS Human Genetic Mutant Cell*

TABLE 4

DIAGNOSES FOR THE SAMPLE OF 207
OLD ORDER AMISH SUBJECTS STUDIED IN GENOME SCAN

| Present Sample | PED. 110 Left Ext. | PED. 110 CORE | PED. 110 1st Rt. Ext | PED. 210 2nd Rt. Ext | PED. 310 | TOTAL |
|---|---|---|---|---|---|---|
| BPI | 3 | 11 | 4 | 2 | 11 | 31 |
| BPII | 0 | 3 | 1 | 1 | 3 | 8 |
| MDD: recurrent | 1 | 5 | 3 | 2 | 4 | 15 |
| MDD: single | 1 | 5 | 1 | 1 | 1 | 9 |
| Other Dx. | 0 | 9 | 1 | 3 | 5 | 18 |
| AFFECTED | 5 | 33 | 10 | 9 | 24 | 81 |
| UNAFFECTED | 5 | 52 | 21 | 19 | 29 | 126 |
| GRAND TOTAL | 10 | 85 | 31 | 28 | 53 | 207 |

Over 125 medical records were abstracted and Board reviewed to document the 31 BPI cases. The average age of onset for BPI disorder was 22 years. Reliability of the bipolar diagnoses was checked when 16 of the 31 cases (52%) were evaluated twice, with an average five year interval between the blind assessments using different clinical documentation and resulting in 100% concordance. The high reliability obtained lessens the likelihood of misdiagnoses or a false positive BPI in our linkage analyses (Egeland et al., *Psychiat. Genet.*, 1:5–18 (1990)).

Apart from RDC diagnoses, the project psychiatric panel also recorded clinical opinions in a consensus "clinical diagnosis." There was 100% concordance between these two types of diagnostic conclusions (5 board members) for the 31 BPI cases and 13 of the 15 cases of recurrent major depressive disorder. Of particular interest are the diagnostic results for the eight cases of BPII. Four were designated BPII by both RDC and clinical opinion. The other four were labelled BPI according to clinical opinion, and two of these actually were classified as "probable BPI" by the strict Research Diagnostic Criteria. This is important to note because it shows that true BPII disorder occurs rarely in these pedigrees; BPII appears more as a "BPI" waiting to happen.

This study of bipolar affective disorder in the Old Order Amish represents a 19 year longitudinal study of an isolated population in which there is a relatively narrow spectrum of

*Repository*, NIH Publication 94-2011, 408–428, 992–999 (1994)). DNA was extracted from peripheral blood samples and/or immortalized lymphoblastoid cell lines (Neitzel, *Hum. Genet.*, 73:320–326 (1986)). The RFLP and microsatellite markers used resulted in a linkage map with an average spacing of between 5 and 10 cM (Gyapay et al., *Nature Gen.*, 7:246–249 (1994), Donis-Keller et al., *Cell*, 51:319–337 (1987)). Mapping panels were constructed to determine the best order of markers typed on the bipolar pedigrees using genotypic data from the CEPH version 7 database, using the MultiMap linkage analysis program (Matise et al, "Automated construction of genetic linkage maps using an expert system (MultiMap): a human genome linkage map" *Nature Genet.* 6:384–390 (1994). Microsatellite markers were genotyped individually by previously described methods (Pauls et al., *Am. J. Hum. Genet.*, 57:636–643 (1995), Sambrook, Molecular Cloning: A Laboratory Manual, 2nd ed., Cold Spring Harbor Press, NY (1989)) and by multiplex procedures adapted from Vignal et al. "Nonradioactive multiplex procedure for genotyping of microsatellite markers" in *Methods in Molecular Genetics*, (ed. Adolph, K. W.) 221—221 (Academic Press, Orlando 1993). In the multiplex genotyping procedures, a total of 25 microsatellite markers were analyzed in each lane of the genotyping gels. To accomplish this, five markers were coamplified in each PCR tube, and five sets of five markers were pooled and precipitated prior to gel loading. Sets of five microsatellite markers were amplified in 20 μl reactions that included: 10 mM Tris-HCl, Ph 8.3, 50 Mm KCl, 0.001% gelatin, 1.5 Mm $MgCl_2$, 0.2 mM dNTPs, 0.5 units Taq polymerase, 1 μM of each primer (10 primers in total), and 50 ng genomic DNA. Samples were denatured at 94° C. for 1 minute, followed by 30–35 cycles at 94° C. for 15 seconds, 55 C for 15 seconds, and 72° C. for 15 seconds. After the final cycle, the reactions were incubated at 72° C. for 3 minutes. Following amplification, five sets of PCR amplifications were pooled and isopropanol precipitated in 96 well microwell plates. The pooled PCR products were resuspended in 10 μl loading dye containing formamide, denatured at 95° C. for 5 minutes and loaded onto 6.0% denaturing polyacrylamide gels. After electrophoresis, the gel fractionated microsatellite markers were transferred to nylon membranes by capillary transfer, and visualized by hybridizing membranes with marker specific, chemiluminescent probes. One of the oligonucleotides used to amplify each marker was labelled with peroxidase using the ECL detection kit (Amersham) and used as probe. Multiple probes corresponding to markers of different sizes were hybridized to the filters simultaneously. Chemiluminscent signals were detected by autoradiography. Allele sizes for the microsatellite markers were determined relative to a PUC18 sequence or SEQUAMARK marker ladder (Research Genetics). To maintain allelic designations for the purposes of allele frequency calculations, DNA samples from replicate individuals were included within and between gels. Films were scored either manually or using semi-automated allele calling software (BioImage), and were independently analyzed by two individuals blind to disease status. Data from manually scored markers and from the automated scoring system were transferred into the same file system for linkage analyses.

EXAMPLE III

This Example describes the statistical analysis of genotypic data.

Since the exact mode of inheritance of bipolar affective disorder is unknown, linkage analyses were carried out using nonparametric (allele sharing, model-independent) methods [SAGE, Sibpal program for Haseman-Elston sib pair tests; affected sibpair analysis (ASP) with weighing of multiple affected in the same sibship by number of meioses; affected pedigree member (APM); and transmission disequilibrium test (TDT)], as well as lod score analyses.

For nonparametric analyses, based on the asymptotic (theoretical) distribution of the test statistic, the SIBPAL program furnished formal (asymptotic) p-values in the test for an excess proportion of alleles shared IBD (identical by descent) and in the Haseman-Elston regression test (Haseman et al., *Behav. Genet.*, 2:3–19 (1972); Keats and Elston, *Genet Epidemiol Supplement* 1:147–152 (1986)). The "true" p-value (the empirical significance level) is defined as the probability that the observed result or one more extreme than it is obtained by chance alone. To estimate empirical significance levels associated with these results rather than relying on the formal p-value, we carried out computer simulations (3000 replicates) for each marker with a formal p-value of 0.01 or less. These simulations were extremely time consuming as a complete analysis had to be carried out for each replicate. Resulting empirical p-values (identified by * in Table 5) typically were about ten times higher than the formal "p-values" issued by the program. In addition, a computer program was written to carry out sib pair analyses in which multiple pairs per sibship are weighed by the number of meioses.

Analysis of allele frequencies for the markers D6S7, D 13S1, and D15S45 was carried out on probands and their mates to test for the existence of linkage disequilibrium. In no case was there a significant difference at the 5% level. For these three marker loci, as well as for the two markers that flanked each, we tested for the presence of specific haplotypes. Again, no haplotypes were significantly more frequent than expected by chance when tested at the 5% level.

The existence of linkage disequilibrium is known to influence certain types of identify-by-state affected sib pair strategies. The basic reason for this is that allele sharing among relatives in isolated populations may be exaggerated due large regions of founder chromosomes that have not been broken up by recombination. For this reason, we employed the TDT to test for linkage, and applied IBD methods, which are unlikely to be significantly influenced by disequilibrium.

A recent described approach, based on all markers of a chromosome, for estimating the proportion of alleles shared IBD was applied to the chromosomes carrying out our best three markers. Lander et al., *Nature Genetics*, 11:241–247 (1995). For allele sharing among all possible affected sib pairs, it resulted in suggestive linkage for locus D6S7. The TDT did not provide p-values suggestive of linkage when applied to the best three loci and BPI affecteds.

Figure 3:
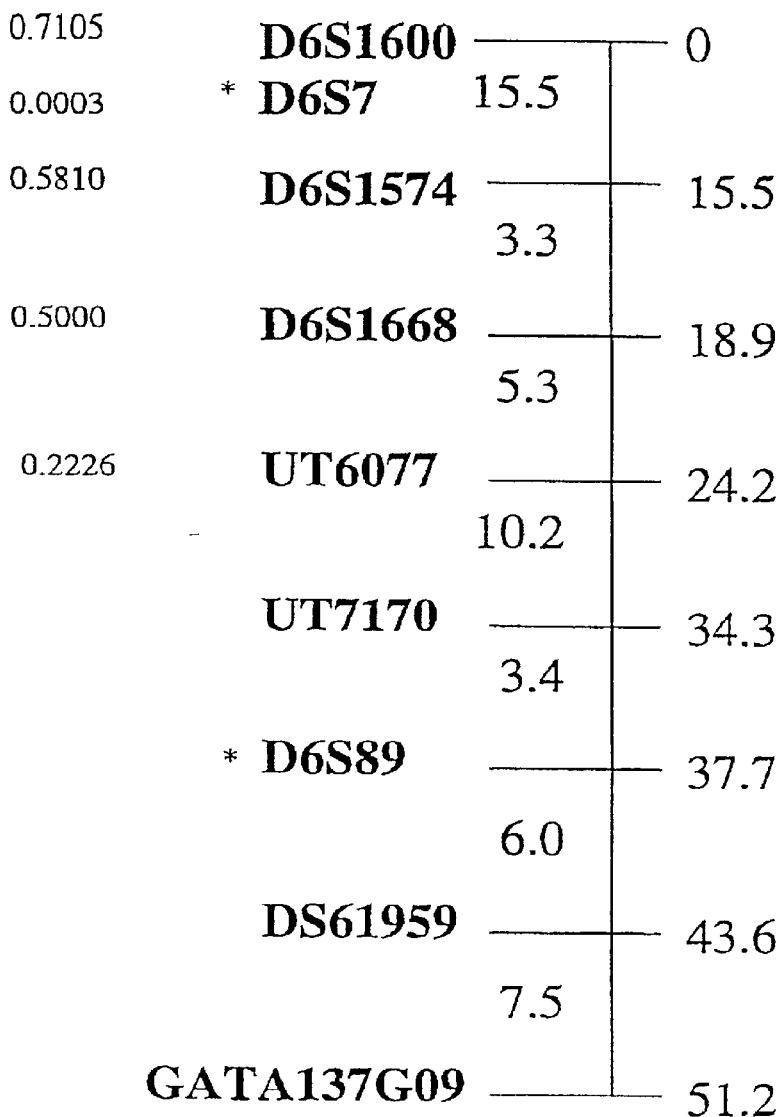
FIG. 3 shows the locations of markers on human chromosome 6 that are associated with susceptibility to BPAD. The statistical significance of the genetic linkage between markers based on sib-pair analysis is shown at left, and map distances between markers (in centimorgans) are indicated in the rightmost two columns.
Figure 5:
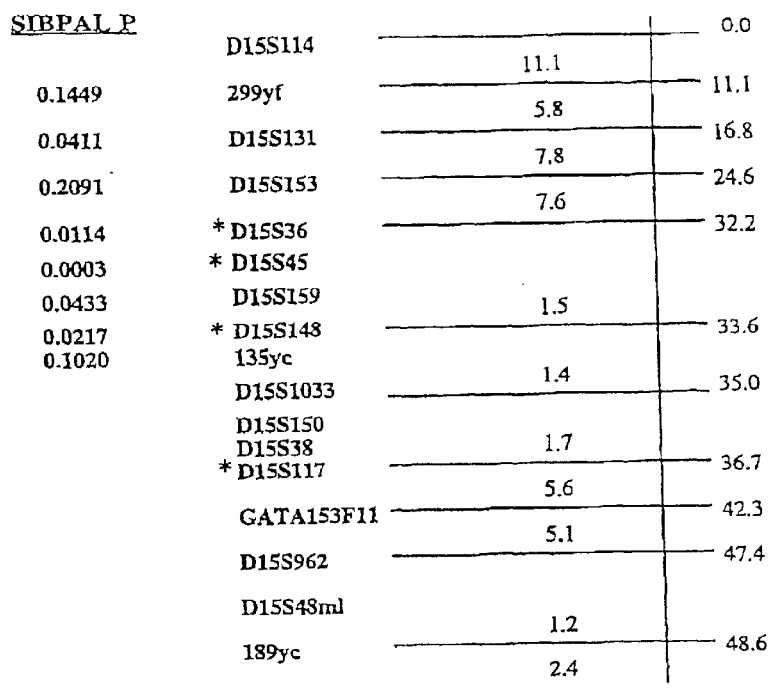
FIG. 5 shows the locations of markers on human chromosome 15 that are associated with susceptibility to BPAD. The statistical significance of the genetic linkage between markers based on sib-pair analysis is shown at left, and map distances between markers (in centimorgans) are indicated in the rightmost two columns.
Figure 8:
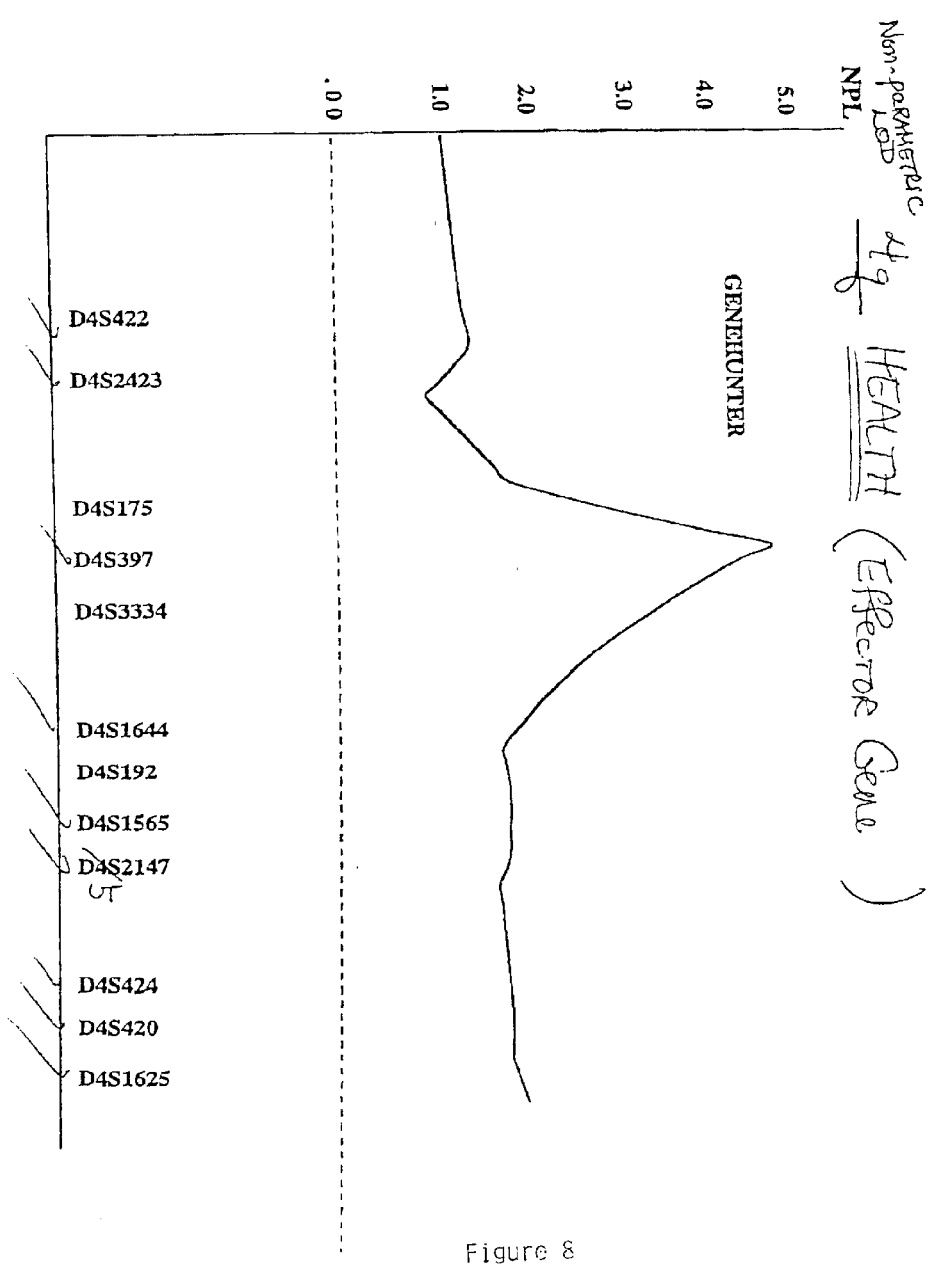
FIG. 8 shows an analysis of the non-parametric LOD among markers on human chromosome 4q that are associated with resistance to BPAD.

For parametric analyses, two-point lod scores were calculated with the LINKAGE programs (Lathrop et al., *Proc. Natl. Acad. Sci., USA*, 81:3443–3446 (1984)). Each marker was analyzed under 16 models (dominant versus recessive inheritance, large pedigrees versus data broken into nuclear families, homogeneity versus allowing for heterogeneity by the HOMOG program (Ott, J., "Analysis of Human Genetic Linkage" (Johns Hopkins University Press, Baltimore, 1991)), and for affecteds only versus affected and unaffected individuals considered). A penetrance ratio (genetic versus nongenetic cases) of 500:1 and disease allele frequencies adjusted to reflect a population prevalence of 1%. Individuals without psychiatric illness under any diagnostic scheme were considered unaffected, whereas those not categorized as affected under one scheme but affected under one of the other diagnostic categories were taken to be unknown. Sixteen models were tested in the lod score analyses, and included: dominant versus recessive inheritance; large pedigrees versus data broken into nuclear families; homogeneity versus allowing for heterogeneity; and analysis for affecteds only versus using affecteds and unaffecteds. To evaluate the effect of analyzing the data under multiple models, we compiled maximum lod scores for the 551 markers obtained under a single model (case 1)(for dominant inheritance, nuclear families, homogeneity, and affected only) and compared them with lod scores obtained under multiple testing (case 2) (FIG. 3). Mean lod scores were 0.18 versus 0.46, for cases 1 and 2, respectively. Thus, multiple testing raised lod scores on the average by 0.28 units. Also, no lod score exceeded 2.0 under the fixed model (case 1), whereas 3 lod scores had values of at least 2.0 under multiple testing (case 2).

Eleven percent of the markers (62 of 551) used in our genome-wide search gave a maximum lod score of 1.0 or higher in at least one of the 16 analysis models. Consequently, only regions which yielded stronger evidence of linkage were considered further, namely those with markers having a test statistic of p<0.001 in any one analysis type, or maximum lod score of at least 2.0. Using these criteria, six markers showed evidence for linkage (D1S48, D6S7, D7S67, D11S146, D13S1, and D15S45).

Marker D11S146 can be obtained from the ATCC using accession Nos. 59230 for a bacterial/phage lysate, or 59231 for purified DNA. Marker D1S48 (Genethon ID G00-000-488) is disclosed in Cartinhour et al., *Cytogenetics and Cell Genetics*, 46:591 (1987). Marker D7S67 (Genethon ID G00-008-432) is disclosed in Donis-Keller et al., *Cell* 51:319–337 (1987).

Markers at three chromosomal loci gave highly significant test statistic p-values under Sibpal (ASP) analyses: D6S7 at chromosome 6pter-p24 with p<0.0001; D13S1 at chromosome 13q13 with p=0.0003; and D15S45 at chromosome 15q11-qter with p=0.0003. Test statistics for these three markers, as well as for markers flanking these regions, are shown in Table 5. These SIBPAL test statistic p-values were estimated using computer simulations (3000 replicates) run under an assumption of no linkage. Therefore, they are not flawed by analyses that would furnish spuriously small formal p-values. In lod score analysis none of the markers reached LOD=3 criterion. However, in some of the non-parametric analysis methods, p-values of less than 0.001 (and even 0.0001, which is asymptotically equivalent to $Z_{max}=3$) are found. Together, these results lend further support to the significance of these intervals as candidate regions.

TABLE 5

RESULTS OF LINKAGE ANALYSES

| Locus | Map dist | Zmax dom | Zmax rec | SIBPAL p | ASP p |
|---|---|---|---|---|---|
| BPI | | | | | |
| D6S344 | | .000 | .000 | .8729 | .2145 |
| D6S7 | 0.0 | 1.456 | .0003* | .0513 | |
| D6S89 | 36.0 | .097 | .001 | .5567 | 1.0000 |
| D6S28 | 17.7 | .000 | .003 | .6262 | .7800 |
| BPI + II1 | | | | | |
| D6S344 | | .000 | .000 | .9249 | .2341 |
| D6S7 | 0.0 | 2.469 | 1.609 | .0000 | .0293 |
| D6S89 | 36.0 | .167 | .000 | .7113 | .3230 |
| D6S28 | 17.7 | .000 | .000 | .6272 | .7867 |
| BPI + II | | | | | |
| D6S344 | | .000 | .000 | .9249 | .2036 |
| D6S7 | 0.0 | 1.885 | .984 | .0003* | .1561 |
| D6S89 | 36.0 | .732 | .394 | .5241 | .2743 |
| D6S28 | 17.7 | .000 | .000 | .6874 | .6892 |
| BPI + II + MDD | | | | | |
| D6S344 | | .000 | .000 | .8977 | .1055 |
| D6S7 | 0.0 | 1.606 | .795 | .0001 | .4195 |
| D6S89 | 36.0 | .732 | .399 | .7126 | .1714 |
| D6S28 | 17.7 | .000 | .000 | .6877 | .7918 |
| BPI | | | | | |
| D13S221 | | .000 | .012 | 1.0000 | .9725 |
| D13S171 | 15.3 | .000 | .102 | .4905 | .3736 |
| D13S1 | 5.2 | 1.276 | 1.248 | .0003* | .0057 |
| D13S218 | 5.1 | .312 | .664 | .0171 | .0641 |
| D13S263 | 10.1 | .056 | .175 | .0865 | .3028 |
| BPI + II1 | | | | | |
| D13S221 | | .000 | .000 | 1.0000 | .8902 |
| D13S171 | 15.3 | .000 | .000 | 1.0000 | .4876 |
| D13S1 | 5.2 | 1.402 | 1.036 | .0000 | .0056 |
| D13S218 | 5.1 | .494 | .423 | .0175 | .0766 |
| D13S263 | 10.1 | .004 | .178 | .1475 | .3998 |
| BPI + II | | | | | |
| D13S221 | | .000 | .000 | 1.0000 | .7344 |
| D13S171 | 15.3 | .000 | .000 | 1.0000 | .4665 |
| D13S1 | 5.2 | 1.203 | .676 | .0090* | .0162 |
| D13S218 | 5.1 | .307 | .314 | .1403 | .1484 |
| D13S263 | 10.1 | .006 | .194 | .2384 | .4033 |
| BPI + II + MDD | | | | | |
| D13S221 | | .000 | .000 | 1.0000 | .7672 |
| D13S171 | 15.3 | .000 | .204 | 1.0000 | .9429 |
| D13S1 | 5.2 | .000 | .043 | .0223 | .0932 |
| D13S218 | 5.1 | .000 | .025 | .3007 | .3202 |
| D13S263 | 10.1 | .000 | .008 | .2262 | .3525 |
| BPI | | | | | |
| D15S45 | | 1.114 | .798 | .0003* | .0163 |
| D15S117 | 5.6 | .130 | .580 | .0843 | .1660 |
| D15S148 | 1.2 | .338 | .610 | .0217 | .1000 |
| D15S38 | 6.1 | .000 | .000 | 1.0000 | .9853 |
| D15S36 | 0.0 | .355 | .400 | .0114 | .0862 |
| BPI + II1 | | | | | |
| D15S45 | | 1.097 | .446 | .0018 | .0456 |
| D15S117 | 5.6 | .332 | .589 | .1225 | .2346 |
| D15S148 | 1.2 | .752 | .613 | .0219 | .0976 |
| D15S38 | 6.1 | .067 | .000 | 1.0000 | .9904 |
| D15S36 | 0.0 | .646 | .402 | .0118 | .0844 |
| BPI + II | | | | | |
| D15S45 | | .857 | .731 | .0183 | .0399 |
| D15S117 | 5.6 | .089 | .726 | .0910 | .1825 |
| D15S148 | 1.2 | .461 | .829 | .0123 | .0589 |
| D15S38 | 6.1 | .000 | .000 | 1.0000 | .8551 |
| D15S36 | 0.0 | .368 | .292 | .0131 | .1172 |
| BP + II + MDD | | | | | |
| D15S45 | | 1.709 | .473 | .0032 | .0150 |
| D15S117 | 5.6 | .000 | .096 | .2119 | .3546 |
| D15S148 | 1.2 | .148 | .192 | .0360 | .0998 |
| D15S38 | 6.1 | .000 | .000 | 1.0000 | .7914 |
| D15S36 | 0.0 | .000 | .000 | .1423 | .3168 |

Map Dist: Map distance in centimorgan between markers;
$Z_{max}$: Maximum lod score in analysis of nuclear families, affected only, penetrance ratio (genetic versus nongenetic cases) of 500:1, with allowance for heterogeneity (exception: for D6S7, affecteds and unaffecteds); $Z_{max}$dom or $Z_{max}$rec: Under dominant or recessive inheritance;
SIBPAL p: p-values furnished by SIBAL program in t-test for excess allele sharing in affected sib pairs (exception: results for regression analysis given for D6S7). For some markers, an empirical p-value, p', was estimated by computer simulation;
ASP p: p-values in t-test for excess of allele sharing in affected sibs, multiple sib pairs, in same sibship weighed by number of meiosis;
Clinical Categories: MDD includes only recurrent major depressive disorder; Number of affecteds in clinical hierarchies were: 31 BPI, 35 BPI + BPII, 39 BPI + BPII, and 49 BPI + BPII + MDD;
1 Only those BP II cases that are borderline BP I are included (such as clinical BP I and RDC manic).

As observed in Table 5, results are typically stronger for BPI than for more liberal diagnostic categories; that is, extending the pool of affected individuals to include additional psychiatric illness (BPII and recurrent MDD) appears to add "noise" to the analyses. Generally, equivalent results are obtained for lod score analyses and our simple ASP analysis, whereas the Haseman-Elston approach (SIBPAL program) typically provided stronger results. The main differences between the programs SIBPAL and ASP consist in the weighing of multiple sib pairs in a sibship (no weighing in SIBPAL). Moreover, SIBPAL deduces ambiguous genotypes from close or distant relatives while ASP does this based only on individuals in the nuclear family. In addition, ASP does not carry out any Haseman-Elston type regression analysis as was applied in the case of marker D6S7. The fact that some markers flanking our strongly significant markers also show positive linkage results provides support for the presence of susceptibility loci near the candidate loci.

The relationship between pointwise (locus-specific or nominal) and genome-wide significance levels was recently discussed. Lander et al., *Nature Genetics*, 11:241–247 (1995). According to this report, for sib pair methods, pointwise P-values of 0.00074 and 0.000022 correspond to suggestive and significant linkage, respectively, with "significant" denoting a genome-wide P-value of 0.05. For lod score analysis, the respective lod score thresholds are 1.9 and 3.3. Thus, according to these criteria, markers D6S7, D13S1, and D15S45 yield locus-specific P-values that are suggestive of linkage.

Our study of bipolar affective disorder in the Old Order Amish, however, represents a 19 year longitudinal study of an isolated population in which there is a relatively narrow spectrum of illness (not one case of schizophrenia occurs in the pedigrees used for linkage analyses) with bipolar disorder being the predominant diagnosis. The rigorous longitudinal assessment of these Amish pedigrees combined with the systematic and blind psychiatric evaluations and diagnoses should also greatly reduce the number of misdiagnoses included in our linkage analyses. Moreover, the restricted gene pool characteristic of this relatively closed population should reduce the number of disease-causing alleles, minimizing the problem of genetic heterogeneity.

Similar to other common and complex diseases like diabetes, hypertension and perhaps even schizophrenia, our data suggest that genetic factors likely contribute to the pathogenesis of bipolar affective disorder, where in the majority of these cases, inheritance is multifactorial rather than simple Mendelian transmission. Like the genetic variance observed for quantitative traits, bipolar affective disorder (even in a relative genetic isolate like the Old Order Amish) appears to be a polygenic (complex) trait resulting from the variable effects of multiple genes. The results of our genome wide scan suggest that genes on chromosomes 6, 13, and 15, rather than just different mutant alleles of a single gene, determine the susceptibility to and phenotype of bipolar affective disorder in the Old Order Amish. Additional sets of genes may underlie the susceptibility to develop bipolar affective disorder in other populations.

EXAMPLE IV

This Example describes the ascertainment of psychiatric disorders and health among several large multigenerational Old Order Amish pedigrees covers a period of over twenty years. Throughout this longitudinal study, procedures for assessing and diagnosing subjects have remained constant (Egeland et al. (1990) *Psychiat. Genet.* 1, 5–18). Moreover, the clinical documentation and diagnostic evaluations have employed rigorous standards and been subjected to a variety of reliability tests (Hostetter et al. (1983) *Am. J. Psychiat.* 140, 62–66). For families in this linkage study, the clinical documentation and diagnostic evaluations have included a thorough evaluation of all available RDC (Spitzer et al. (1978) *Arch. Gen. Psychiat.* 35, 773–782) bipolar I (BPI) probands and their relatives. Morbid risk analyses have demonstrated a high prevalence of affective disorder among first degree relatives of bipolar probands in these families with the highest risk conferred on the children of a BPAD parent (Pauls et al. (1992) *Arch. Gen. Psychiat.* 49, 703–708). Importantly, because of the long-term, longitudinal nature of the study, even the unaffected, mentally healthy individuals (those without any psychiatric illness) in these families have been closely followed, many for a period of years past the age of risk for BPAD. Consequently, rather than limit this genome-wide search to identifying susceptibility loci for the disease phenotype (BPAD), we tested the hypothesis that "protective" alleles may contribute to the absence of psychiatric illness (i.e. mental health "wellness") in unaffected family members in these "high risk" pedigrees. Since the mode of inheritance of any gene(s) modifying the relative risk for affective disorder was unknown (Craddock, N. & McGuffin, P. (1993) *Ann. Med.* 25, 317–322) we relied exclusively on model-free linkage analyses.

This Example reports strong evidence for linkage of DNA markers on chromosome 4p to mental health "wellness" in relatives at high risk for, but who did not develop, major affective disorder in several large multigenerational Old Order Amish pedigrees with an extremely high incidence of BPAD.

Materials and Methods

Diagnostic Assessment.

Figure 10:
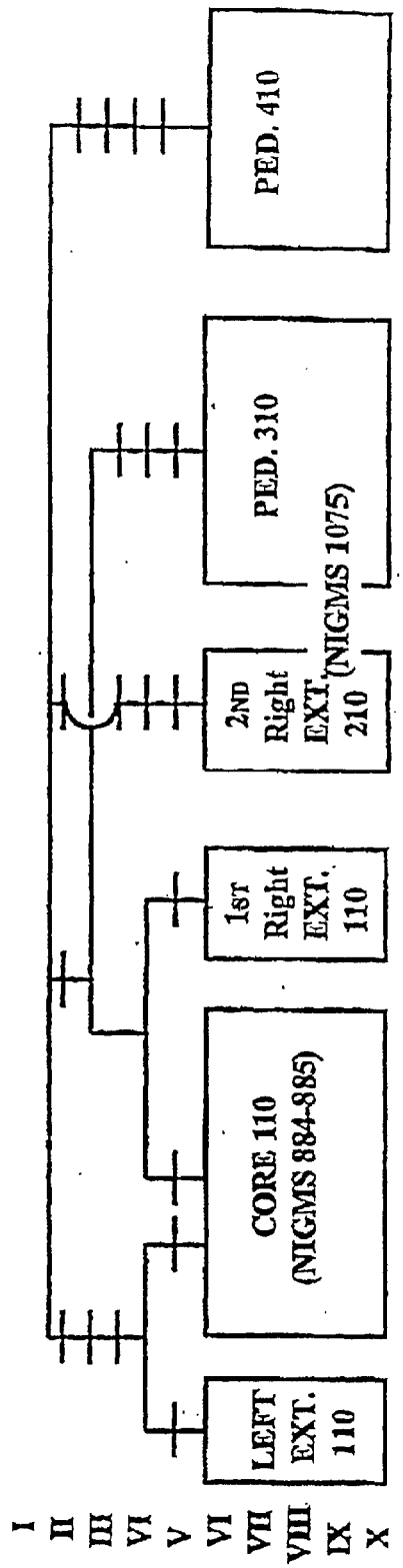
FIG. 10 shows a summary of the ancestral trace for Amish study bipolar pedigrees in "schematic" representation. The LEFT extension coupled with the CORE Pedigree 110 provided the resource used to initially report linkage findings (Egeland et al. (1987) Nature 325, 783–787). Further genetic analyses were reported in 1989 after addition of a RIGHT extension to Pedigree 110 (Kelsoe et al. (1989) Nature 342, 238–243). Pedigree 210 and partial Pedigree 310 (NIGMS Family 1075) became an additional large lateral extension, that along with the earlier subjects, was used in the genome-wide linkage analyses reported in 1996 (Ginns et al. (1996) Nature Genet. 12, 431–435). The study reported in Example IV utilized all of these earlier subjects plus additional expansions, especially in Pedigree 410, so that the overall Study contained 346 samples, including those from 50 BPI individuals.

Our genetic-epidemiologic study of BPAD among the Old Order Amish in southeastern Pennsylvania has been described in detail (Egeland, J. A. (1994) in *Genetic Studies in Affective Disorders*, eds Papolos, D. F. & Lachman, H. M., (John Wiley & Sons, New York) pp. 70–90), including the methods for ascertainment and diagnostic evaluation with informed consent (medical records and SADS-L interviews) (Spitzer et al. (1978) *Arch. Gen. Psychiat.* 35: 773–782; Endicott, J. & Spitzer, R. (1978) *Arch. Gen. Psychiat.* 35: 837–844). Diagnoses were made, using strict research diagnostic criteria (RDC)(Spitzer et al., supra.), by a five member psychiatric review board whose members were blind to pedigree membership, diagnostic opinions, treatment data from abstracted medical records and genetic marker status. By the late 1970's, several dozen BPI probands had been certified by the psychiatric Board. Subsequently, interviewing began on all available first degree relatives using the SADS-L instrument. In this initial screening, over 300 first degree relatives were interviewed directly with the SADS-L. These 25 nuclear families, containing one or more cases of BPI, formed the structure of Pedigrees 110, 210 and 310 (FIG. 10).

The BPI probands in the nuclear families used in this linkage study have on the average 11.6 first degree relatives. A few siblings were unavailable, while either both parents (57%) or one parent (23%) were available for interviews and blood samples. Cell lines have been established on an average of eight members for each nuclear family.

In this study, the "unaffected" individuals (mentally "well" or "healthy") are those for whom all SADS-L interview responses were negative (normal) and no contradictory reports were given by family informants. Any individuals for whom some symptomatology was identified, even though it did not meet criteria for which the psychiatric Board could give a formal diagnosis by RDC, were labeled as "unknowns" in our linkage analyses.

The method used for this longitudinal study is ethnographic and hence culturally appropriate to the field setting. Each "well" person is not seen annually, nor is every individual in a family routinely re-interviewed with the SADS-L. Instead, several members of each nuclear family with a BPI proband (BPI nuclear family) are seen annually, and those diagnosed with BPI or other major affective disorder undergo a yearly "course-of-illness" update. Parents of each BPI patient are regularly visited and they have proven to be accurate informants about the health of their children and grandchildren. At least one "unaffected" sibling (control sample) of the married BPI patients has been interviewed yearly since 1990 in connection with a prospective study of "children-at-risk" for bipolar disorder. In summary, at least three members and occasionally all members of each BPI nuclear family have been evaluated yearly.

Individuals are interviewed anew with the complete SADS-L schedule whenever any abnormal mental or emotional symptoms are identified by the follow-up mechanisms. Nearly 50% of those subjects presently carrying a diagnosis of a major affective disorder, including BPI, were "unaffected" at the time of the initial SADS-L interview. The long-term, systematic follow-up of the families in our study has demonstrated that onset of illness in the Old Order Amish is usually reported by multiple informants. We are confident that individuals designated as "healthy" are free of any significant affective disorder.

Patient Samples.

Blood samples were uniformly collected only after each first degree relative (including parents, siblings and children older than age 15) of the BPI probands had been interviewed with the complete SADS-L schedule. Samples were obtained with written informed consent and coded to maintain confidentiality. The phlebotomist was kept blind to pedigree relationships and diagnostic status. Lymphoblastoid cell lines were established at the Coriell Institute for Medical Research, Camden, N.J. and/or the Clinical Neuroscience Branch, IRP, National Institute of Mental Health, Bethesda, Md. The NIGMS Human Genetic Mutant Cell Repository catalogue (Egeland, J. A. Amish major affective disorders pedigrees. (1994) In 1994–1995 *Catalog of Cell Lines*, NIGMS Human Genetic Mutant Cell Repository, 408–428, 992–999 (NIH Publication 94-2011) contains updated pedigree and diagnostic information for several of the Amish pedigrees used in our study.

Genotyping.

Genomic DNA was obtained from peripheral blood samples and/or immortalized lymphoblastoid cell lines as previously described (Ginns et al. (1996) *Nature Genet.* 12, 431–435). The best order of typed markers on our mapping panels was obtained from the genetic location database (LDB) (Collins et al. (1996) *Proc. Natl. Acad. Sci. USA.* 93, 14771–14775). The order of markers on chromosome 4p is: D4S412-6.50cM-D4S431-0.24cM-D4S2366-0.2cM-D4S2935-1.3cM-D4S3007-1.3cM-D4S394-2.0cM-D4S2983-0.00cM-D4S2923-0.00cM-D4S615-0.05cM-AFMa184za9-1.54cM-D4S2928-1.51cM-D4S1065-0.04cM-D4S1582-0.65cM-D4S107-1,46cM-D4S3009-0.30cM-D4S2906-0.00cM-D4S2949-0.05cM-AFM087zg5-0.24cM-D4S2944-0.11cM-D4S403-0.4cM-D4S2942-0.00cM-D4S2984-0.00cM-D4S1602-1.11cM-D4S1511-1.49cM-D4S2311-2.15cM-D4S3048-3.62cM-D4S419-1.75cM-D4S404-2.5cM-D4S391. The order of markers on chromosome 4q is: D4S3043-27.91cM-D4S402-0.9cM-D4S427-1.64cM-D4S2303-2.49cM-D4S2985-0.63cM-D4S2423-2.39cM-D4S2286-1.50cM-D4S2959-1.01cM-D4S175-0.40cM-D4S422-0.24cM-D4S1576-4.10cM-D4S2294-0.04cM-D4S1579-0.54cM-D4S397-0.01cM-D4S3089-0.10cM-D4S2965-0.03cM-D4S192-0.01cM-D4S420-0.05cM-D4S1644-0.02cM-D4S3344-0.02cM-D4S1565-1.27cM-D4S1625-0.12cM-D4S424-0.04cM-D4S1604-2.31cM-D4S1548. The order of markers on chromosome 11q is: D11S934-2.1cM-D11S133-8.7cM-D11S147-4.0cM-CD3D-0.2cM-D11S285-0.1cM-D11S29.

DNA panels for PCR were set up using a 96 microtiter plate format, and the PCR master mix was aliquoted using a BioMek robot (Beckman Instruments). PCR was performed using Perkin-Elmer model 9600 and 9700 thermocyclers. PCR products for a given DNA marker were optimized by carrying out PCR amplification at 3 different annealing temperatures on a test panel of genomic DNA samples, and by determining the fluorescence signal amplitude and shape following electrophoresis using the ABI 373 fluorescent sequencing/genotyping instrument (Applied Biosystems Division, Perkin-Elmer). DNA markers were usually processed in groups of six. The genomic DNA samples were PCR amplified separately with each of the DNA markers. The PCR products were then multiplexed, 6 markers per lane, for electrophoresis on the ABI 373 instruments (Applied Biosystems Division, Perkin-Elmer). The DNA from several individuals was represented multiple times in the genotyping panels so that within and between each electrophoresis gel there were "identical" samples that could be used to evaluate the consistency of genotypes across several gels. The fluorescent signals from amplified fragments were tracked using Genescan (Applied Biosystems Division, Perkin-Elmer), and genotypes were subsequently analyzed with Genotyper (Applied Biosystems Division, Perkin-Elmer).

Genetic Analysis Software (G.A.S. package version 2.0, Alan Young, Oxford University, 1993–1995) was used to identify problematic marker data, and a utility written in SPSS (SPSS Inc.) generated a list of samples that needed to be rerun because of inheritance discrepancies or unreadable signals. Samples that had to be rerun were repicked by a Microlab 2200 robot (Hamilton Instruments), aliquoted, electrophoresed and analyzed. Because we are studying large multigenerational pedigrees where individuals are descendants of a few progenitors, we maximize the useful information by repeating the genotyping/analysis cycles described above until all possible DNA marker genotypes are obtained for the individuals in the study.

Once genotyping for a marker was finished, the data were reanalyzed with G.A.S., observed allelic mutations and other non-inheritances were "zeroed out" in the data file, and the problematic alleles were notated on pedigree drawings. Histograms were generated indicating the marker allele size bins. FASTLINK (Schaffer, A. A. (1996) *Hum. Hered.* 46, 226–235) was used to reanalyze the data prior to further statistical analyses.

Linkage Analyses.

Model-free linkage analyses were conducted using the two-point affected sib pair analysis program S.A.G.E. SIB-PAL (S.A.G.E. *Statistical Analysis for Genetic Epidemiology, Release* 3.0. (1997) Computer package available from the Department of Epidemiology and Biostatistics, Rammelkamp Center for Education and Research, MetroHealth Campus, Case Western Reserve University, Cleveland, Ohio) and the multipoint analysis program GENEHUNTER-PLUS (Kruglyak, L. & Lander, E. S. (1995) *Am. J. Hum. Genet.* 56, 1212–1223). Because there were a few sibships with incomplete marker information, marker allele frequencies were estimated from the entire Old Order Amish family data set using a maximum likelihood method implemented in the program MENDEL/USERM13 (Lange et al. (1988) *Genet. Epidem.* 5, 471–472; Boehnke, M. (1991) *Am. J. Hum. Genet.* 48, 22–25). SIB-PAL was used to identify markers showing an excess of alleles shared identical by descent (IBD) among unaffected, mentally healthy sib pairs. Under the null hypothesis of no linkage between a trait and marker, sib pairs would be expected to share on the average fifty percent of alleles IBD, but when a trait and marker are linked, IBD sharing will be increased in both affected and unaffected sibpairs. Because SIBPAL assumes marker allele frequencies appropriate for random samples, it underestimates the proportion of alleles shared IBD by concordant sib pairs when there is linkage. Multipoint analyses using the model-free linkage program GENEHUNTER-PLUS produced NPL (non-parametric linkage) scores along points at the chromosomal region of interest. Two scoring functions are available in GENEHUNTER-PLUS: IBD sharing can be assessed among concordant relative pairs ($NPL_{pairs}$) or it may be assessed among larger groups of concordant relatives ($NPL_{all}$). Our analyses were conducted using the $NPL_{all}$ statistics as Kruglyak and colleagues have demonstrated that the $NPL_{all}$ statistic results in a more powerful test than the $NPL_{pairs}$ statistic (Boehnke, supra.).

Results

Figure 11:
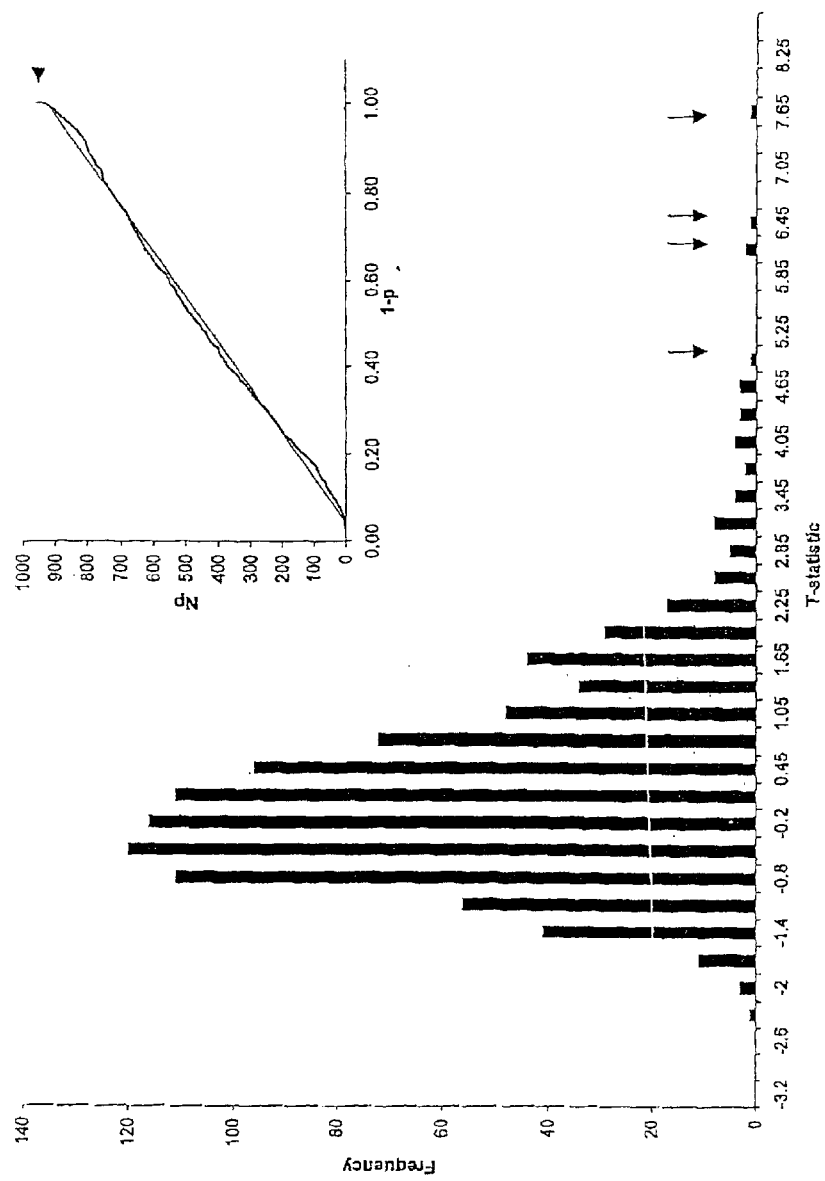
FIG. 11 shows a plot of t-statistics obtained from the pair-wise linkage results. The figure insert depicts a cumulative plot of p-values whose linearity would reflect uniformity in p-values associated with multiple linkage results whose null hypotheses were all true (see text). The outlying t-statistics and p-values (denoted by arrows) were associated with markers, D4S107 (t=6.24), D4S2949 (t=7.79), D4S2928 (t=5.03), D11S133 (t=6.09), and D11S29 (t=6.32).

First we analyzed our genome-wide scan dataset looking for evidence of chromosome regions linked to mental health "wellness". In these analyses only mental health "wellness" (the absence of any psychiatric illness), in individuals who were over 45 years of age and had a first degree BPI sibling in their family (Pedigrees 110, 210, 310 and 410), was the linkage phenotype of interest (concordantly unaffected pairs) using SIBPAL. Of more than 980 DNA markers, only six markers representing three chromosome regions had t-statistics that were sufficiently outlying and that were likely to represent significant linkage results. Of the markers on chromosome 4p, D4S2949, which is located in the vicinity of the BPAD susceptibility locus reported by Blackwood et al. ((1996) Nature Genet. 12, 427–430), had an empirical SIBPAL p value<$5 \times 10^{-5}$ (nominal p value<$1 \times 10^{-7}$). The marker D4S397 on chromosome 4q had an empirical SIBPAL p value=$9 \times 10^{-4}$ (nominal p value=$3 \times 10^{-7}$) On chromosome 11q, two DNA markers (D11S133 and D11S29) located over an approximately 20cM region each had a nominal p value<$5 \times 10^{-5}$ (SIBPAL; simulations were not performed). To supplement standard criteria for assessing the significance of our linkage analysis results, we employed graphical techniques (FIG. 11) and the empirical assessment of p values (Schweder, T. & Spjotvoll, E. (1982) Biometrika. 69, 493–502; Witte et al. (1996) Nature Genet. 12, 355–358; Drigalenko, E. L. & Elston, R. C. (1997) Genetic Epidem. 14, 779–784). If each marker assessed in a pairwise linkage analysis is unlinked to the trait, then the p values associated with those markers should be uniformly distributed. In addition, the test-statistics used to generate these p values (for instance t-tests in the case of SIBPAL) should follow an appropriate distribution. A plot (generated using Proc Chart, SAS, SAS Institute Inc.) of the t-statistics obtained from each pairwise linkage analysis is shown in FIG. 11. The plot in the inset depicts a line that should be linear if all markers are unlinked. However, as seen in FIG. 11, there are outlying t-statistic values that likely represent false null hypotheses; that is, evidence for significant linkage results. In addition, in the inset to FIG. 11, the small upturned portion of the p value plot near values of 1-p=1 represent departures from uniformity and hence most likely reflect false null hypotheses. Because of the effort required to investigate the significance of these findings and the prior evidence supporting a BPAD related locus on chromosome 4 (Blackwood et al. (1996) Nature Genet. 12, 427–430), we chose to examine DNA markers on chromosome 4 first for linkage to mental health "wellness".

To evaluate the findings on chromosome 4p and 4q in more detail, we genotyped the subpedigrees and nuclear families containing at least one sibling with BPI (Table 6) using additional DNA markers in these interesting regions. Compared to our previous report (Ginns et al. (1996) Nature Genet. 12, 431–435) a larger number of individuals were included in these analyses (Table 6). In this report, model-free linkage analyses using SIBPAL and GENEHUNTER-PLUS (Krugylak et al. (1996) Am. J. Hum. Genet. 58, 134–1363) were performed using mental health "wellness" as the linkage phenotype (Tables 7 and 8). In our analyses, individuals having a psychiatric diagnosis other than BPI, as well as those having psychiatric symptoms but no diagnosis, were classified as "unknown category" for affected status. In the Amish Study sample of BPI patients (n=59) the mean and median ages of onset (RDC) are 24 and 22 years, respectively. Hence, in all analyses we used a conservative age cutoff of 45 years to define family members with the unaffected "wellness" phenotype. We also examined the influence of younger age cutoffs for defining "well" individuals, and the contribution of different subpedigrees (families from pedigrees 110, 210, 310, and 410 versus only families from pedigree 110) on the test statistics for linkage (Tables 9 and 10). "Well" individuals younger than the specified age cutoff were considered to have an "unknown" affected status in the analyses.

TABLE 6

Old Order Amish subjects included in linkage analysis

| | Analysis Mentally Healthy | Categories "Unknowns" |
|---|---|---|
| Pedigrees 110, 210, 310, 410 | | |
| ≧25 years old | 138 | 85 |
| ≧35 years old | 109 | 114 |
| ≧45 years old | 74 | 149 |
| ≧55 years old | 52 | 171 |
| Pedigree 110 only | | |
| ≧25 years old | 45 | 32 |
| ≧35 years old | 37 | 40 |
| ≧45 years old | 31 | 46 |
| ≧55 years old | 23 | 54 |

In Table 6, the category of "unknowns" includes individuals of unknown phenotype, individuals with psychiatric diagnoses other than BPI, and individuals who are mentally healthy but are younger than the particular age cut-off used in analyses. BPI individuals are not included in the unknown phenotype category. In pedigrees 110, 210, 310 and 410, 39 people were diagnosed with BPI, 8 with BPII, 21 with recurrent depressive disorder, 2 with unipolar depressive disorder and 15 with other psychiatric illness. In pedigree 110 only, 18 people were diagnosed with BPI, 2 with BPII, 10 with major depressive disorder, and 5 with other psychiatric illness. Note: the individuals used in these linkage analyses represent only a subset of the entire Amish bipolar pedigrees since only nuclear families and subpedigrees containing a sibling with BPI were included.

TABLE 7

Results of SIBPAL analysis of 4p markers

| | Pedigree 110 | | | Pedigrees 110, 210, 310, 410 | | |
|---|---|---|---|---|---|---|
| | | p-value | | | p-value | |
| Marker | Î (s.e) | nominal | simulated | Î (s.e.) | nominal | simulated |
| D4S412 | .4749(.0621) | .6555 | np | .5116(.0539) | .4154 | np |
| D4S431 | .5734(.0441) | .0523 | np | .5921(.0388) | .0110 | np |
| D4S2366 | .6781(.0452) | .0002 | .0005 | .6024(.0356) | .0027 | .0094 |
| D4S2935 | .5066(.0218) | .3825 | np | .4998(.0198) | .5043 | np |

TABLE 7-continued

Results of SIBPAL analysis of 4p markers

| | Pedigree 110 | | | Pedigrees 110, 210, 310, 410 | | |
|---|---|---|---|---|---|---|
| | | p-value | | | p-value | |
| Marker | Π̂ (s.e) | nominal | simulated | Π̂ (s.e.) | nominal | simulated |
| D4S3007 | .6233(.0386) | .0014 | .0023 | .5632(.0337) | .0330 | .0496 |
| D4S394 | .6782(.0513) | .0007 | .0012 | .5955(.0421) | .0135 | .0249 |
| D4S2983 | .7219(.0484) | $<1 \times 10^{-4}$ | np | .6090(.0377) | .0025 | np |
| D4S2923 | .6661(.0446) | .0003 | np | .5902(.0307) | .0022 | np |
| D4S615 | .7161(.0393) | $<1 \times 10^{-4}$ | np | .6223(.0324) | .0002 | np |
| Afma184xa9 | .7396(.0446) | $<1 \times 10^{-4}$ | np | .6220(.0370) | .0008 | np |
| D4S2928 | .7333(.0257) | $<5 \times 10^{-5}$ | np | .6369(.0272) | $<5 \times 10^{-5}$ | np |
| D4S1605 | .5453(.0258) | .0440 | .0472 | .5795(.0244) | .0011 | 0.0058 |
| D4S1582 | .6787(.0616) | .0032 | .0112 | .6269(.0557) | .0139 | .0510 |
| D4S107 | .6557(.0246) | $<5 \times 10^{-5}$ | .0029 | .6514(.0243) | $<5 \times 10^{-5}$ | .0088 |
| D4S3009 | .7325(.0552) | .0001 | np | .6237(.0379) | .0008 | np |
| D4S2906 | .6460(.0396) | .0004 | np | .5853(.0327) | .0055 | np |
| D4S2949 | .7077(.0202) | $<1 \times 10^{-7}$ | $<3 \times 10^{-5}$ | .6888(.0243) | $<1 \times 10^{-7}$ | $<3 \times 10^{-5}$ |
| Afm087zg5 | .5229(.0368) | .2686 | np | .5114(.0246) | .3218 | np |
| D4S2944 | .5647(.0263) | .0093 | np | .5428(.0255) | .0483 | np |
| D4S403 | .6032(.0492) | .0217 | .0233 | .5989(.0443) | .0232 | .0350 |
| D4S2942 | .7196(.0308) | $<1 \times 10^{-4}$ | np | .6627(.0243) | $<1 \times 10^{-4}$ | np |
| D4S2984 | .5510(.0396) | .1032 | np | .5493(.0297) | .0505 | np |
| D4S1602 | .6001(.0561) | .0412 | np | .5703(.0383) | .0356 | np |
| D4S1511 | .6242(.0489) | .0077 | np | .5779(.0315) | .0079 | np |
| D4S2311 | .7429(.0279) | $<5 \times 10^{-5}$ | np | .6327(.0336) | .0001 | np |
| D4S3048 | .6628(.0573) | .0036 | np | .5998(.0403) | .0078 | np |
| D4S419 | .5981(.0270) | .0004 | .0010 | .5772(.0319) | .0100 | .0201 |
| D4S404 | .6785(.0489) | .0004 | .0010 | .6428(.0470) | .0020 | .0072 |
| D4S391 | .7008(.0487) | .0001 | .0003 | .6585(.0470) | .0008 | .0035 |

Π̂ is the estimated proportion of alleles shared identical by descent.
np: simulations not performed

TABLE 8

Results of SIBPAL analysis of 4q markers

| | Pedigree 110 | | | Pedigrees 110, 210, 310, 410 | | |
|---|---|---|---|---|---|---|
| | | p-value | | | p-value | |
| Marker | Π̂ (s.e) | nominal | Simulated | Π̂ (s.e.) | nominal | simulated |
| D4S3043 | .4490(.0531) | .8286 | np | .5143(.0354) | .3442 | np |
| D4S402 | .4649(.0525) | .7460 | np | .4598(.0463) | .8048 | np |
| D4S427 | .4759(.0452) | .7016 | np | .4564(.0345) | .8944 | np |
| D4S2303 | .4616(.0423) | .8145 | np | .4670(.0305) | .8585 | np |
| D4S2985 | .5754(.0255) | .0027 | np | .5403(.0139) | .0025 | np |
| D4S2423 | .5445(.0415) | .1453 | .1373 | .5445(.0304) | .0743 | .0846 |
| D4S2286 | .5533(.0522) | .1570 | np | .5225(.0381) | .2780 | np |
| D4S2959 | .5035(.0359) | .4619 | np | .4906(.0268) | .6370 | np |
| D4S175 | .5960(.0558) | .0471 | .0636 | .5995(.0484) | .0231 | .0348 |
| D4S422 | .6198(.0500) | .0108 | np | .5685(.0386) | .0403 | np |
| D4S1576 | .5290(.0509) | .2861 | np | .5377(.0367) | .1545 | np |
| D4S2294 | .4960(.0446) | .5351 | np | .4867(.0381) | .6358 | np |
| D4S1579 | .6206(.0381) | .0015 | np | .5740(.0298) | .0077 | np |
| D4S397 | .7511(.0449) | $3 \times 10^{-7}$ | .0009 | .6586(.0376) | $5 \times 10^{-6}$ | .0002 |
| D4S3089 | .4544(.0348) | .9013 | np | .4768(.0261) | .8120 | np |
| D4S2965 | .5296(.0581) | .3068 | np | .5267(.0366) | .2340 | np |
| D4S192 | .5135(.0408) | .3715 | np | .5040(.0337) | .4525 | np |
| D4S420 | .5595(.0539) | .1384 | np | .5462(.0389) | .1200 | np |
| D4S1644 | .5224(.0521) | .3351 | .2870 | .5503(.0362) | .0845 | .0925 |
| D4S3334 | .5491(.0254) | .0304 | .0497 | .5258(.0287) | .1858 | .1769 |
| D4S1565 | .5091(.0373) | .4042 | np | .5040(.0271) | .4420 | np |
| D4S1625 | .5433(.0454) | .1730 | np | .5533(.0339) | .0603 | np |
| D4S424 | .5901(.0527) | .0481 | np | .5950(.0461) | .0226 | np |
| D4S1604 | .5501(.0473) | .1480 | np | .5095(.0345) | .3919 | np |
| D4S1548 | .5597(.0356) | .0511 | np | .5814(.0267) | .0016 | np |

Π̂ is the estimated proportion of alleles shared identical by descent.
np: simulations not performed

TABLE 9

Results of SIBPAL analysis of selected 4p markers by age

| | | Pedigree 110 | | | Pedigrees 110, 210, 310, 410 | | |
|---|---|---|---|---|---|---|---|
| Marker | Age | Π̂ (s.e.) | t-value | p-value | Π̂ (s.e.) | t-value | p-value |
| D4S2366 | ≥25 | .5906(.0415) | 2.1813 | .0163 | .5268(.0220) | 1.2195 | .1121 |
| | ≥35 | .6295(.0482) | 2.6843 | .0051 | .5459(.0290) | 1.5846 | .0580 |
| | ≥45 | .6781(.0452) | 3.9389 | .0002 | .6024(.0356) | 2.8783 | .0027 |
| D4S3007 | ≥25 | .5567(.0341) | 1.6625 | .0505 | .5231(.0196) | 1.1767 | .1205 |
| | ≥35 | .5767(.0423) | 1.8139 | .0383 | .5263(.0276) | 0.9529 | .1716 |
| | ≥45 | .6233(.0386) | 3.1978 | .0014 | .5632(.0337) | 1.8729 | .0330 |
| D4S394 | ≥25 | .5872(.0397) | 2.1935 | .0159 | .5306(.0220) | 1.3885 | .0834 |
| | ≥35 | .6242(.0524) | 2.3713 | .0111 | .5560(.0331) | 1.6911 | .0471 |
| | ≥45 | .6782(.0513) | 3.4734 | .0007 | .5955(.0421) | 2.2683 | .0135 |
| D4S1605 | ≥25 | .5287(.0259) | 1.1076 | .1361 | .5367(.0227) | 1.6194 | .0541 |
| | ≥35 | .5271(.0270) | 1.0039 | .1608 | .5405(.0276) | 1.4686 | .0739 |
| | ≥45 | .5453(.0258) | 1.7551 | .0440 | .5795(.0244) | 3.2623 | .0011 |
| D4S1582 | ≥25 | .5695(.0439) | 1.5849 | .0588 | .5078(.0250) | 0.3110 | .3781 |
| | ≥35 | .6025(.0586) | 1.7505 | .0436 | .5268(.0358) | 0.7487 | .2280 |
| | ≥45 | .6787(.0616) | 2.9012 | .0032 | .6269(.0557) | 2.2772 | .0139 |
| D4S2949 | ≥25 | .6035(.0305) | 3.3967 | .0006 | .5499(.0205) | 2.4289 | .0081 |
| | ≥35 | .6497(.0310) | 4.8265 | $9 \times 10^{-6}$ | .6035(.0260) | 3.9796 | $6.8 \times 10^{-5}$ |
| | ≥45 | .7077(.0202) | 10.2884 | $<1 \times 10^{-7}$ | .6888(.0243) | 7.7856 | $<1 \times 10^{-7}$ |

Π̂ is the estimated proportion of alleles shared identical by descent.

TABLE 10

Results of SIBPAL analysis of selected 4q markers by age

| | | Pedigree 110 | | | Pedigrees 110, 210, 310, 410 | | |
|---|---|---|---|---|---|---|---|
| Marker | Age | Π̂ (s.e.) | t-value | p-value | Π̂ (s.e.) | t-value | p-value |
| D4S175 | ≥25 | .5254(.0402) | 0.6314 | .2650 | .5209(.0283) | 0.7398 | .2305 |
| | ≥35 | .5730(.0524) | 1.3932 | .0857 | .5557(.0420) | 1.3258 | .0952 |
| | ≥45 | .5960(.0558) | 1.7200 | .0471 | .5995(.0484) | 2.0536 | .0231 |
| D4S397 | ≥25 | .6599(.0307) | 5.2010 | $1 \times 10^{-6}$ | .6303(.0243) | 5.3595 | $2 \times 10^{-7}$ |
| | ≥35 | .7455(.0427) | 5.7485 | $6 \times 10^{-7}$ | .6622(.0383) | 4.2358 | $4.5 \times 10^{-5}$ |
| | ≥45 | .7511(.0449) | 5.5883 | $3 \times 10^{-7}$ | .6586(.0376) | 4.2156 | $5 \times 10^{-6}$ |
| D4S3334 | ≥25 | .5571(.0265) | 2.1548 | .0174 | .5369(.0187) | 1.9786 | .0246 |
| | ≥35 | .5483(.0280) | 1.7269 | .0457 | .5213(.0238) | 0.8968 | .1859 |
| | ≥45 | .5491(.0254) | 1.9346 | .0304 | .5258(.0287) | 0.8996 | .1858 |

Π̂ is the estimated proportion of alleles shared identical by descent.

On chromosome 4p, the maximum multipoint NPL value (GENEHUNTER-PLUS) was 4.05 ($p=5.22\times10^{-4}$; including individuals>age 45 yrs in pedigree 110 only) and 4.05 ($p=1.84\times10^{-4}$; including individuals>age 45 yrs in all pedigrees), respectively. The maximum multipoint NPL value (GENEHUNTER-PLUS) for markers on chromosome 4q was 3.29 ($p=2.57\times10^{-3}$; including individuals>age 45 yrs in pedigree 110 only) and 2.82 ($p=4.43\times10^{-3}$; including individuals>age 45 yrs in all pedigrees), respectively. The GENEHUNTER-PLUS $-\log_{10}p$ value as a function of the map position at these locations on chromosome 4 are shown in FIG. 12. SIBPAL test statistics for markers on chromosomes 4p and 4q are shown in Tables 7 and 8. On chromosome 4 the lowest (nominal) p values obtained from the SIBPAL t-statistics were for markers D4S2949 (4p; $p<1\times10^{-7}$) and D4S397 (4q; $p=3\times10^{-7}$). The maximum multipoint NPL value (GENEHUNTER-PLUS) for markers on chromosome 11q was 2.43 (including individuals>age 45 yrs in pedigree 110 only) and 2.49 (including individuals>age 45 yrs in all pedigrees), respectively.

To obtain empirical p-values, we simulated genotype data by randomly assigning marker alleles to the founders and then assigning alleles to their descendants following Mendelian inheritance. Allowing for consanguineous matings, the entire family structure (FIG. 10) was used in marker assignment, thus taking into account all relationships between individuals in the dataset. For each simulation, after marker assignment, the pedigrees were trimmed down to that of the nuclear families used in the linkage analysis. SIBPAL was then run on the trimmed dataset and t-statistics for concordant and discordant sib pairs were obtained. The true p value is simply estimated as the proportion of replicates in which the simulated statistic is greater than or equal to the observed statistic, i.e., the probability that the observed result or something more extreme would be obtained by chance alone. Simulations were conducted for markers on chromosomes 4p and 4q. For each marker, 100,000 replicates were obtained. The empirical p values on chromosome 4p clearly meet the proposed criteria of significance for linkage (Lander, E. S. & Kruglyak, L. (1995) *Nature Genet.* 11, 241–247).

Discussion

If alleles exist that are associated with mental health "wellness", we reasoned that the identification of chromosome regions containing these alleles would be enhanced by studying the genetically at risk, mentally healthy members of large, multigenerational pedigrees like our Old Order Amish families'. However, in trying to identify "protective" or "wellness" alleles, one must recognize that there are phenocopies that need to be considered. Despite the extremely high risk for developing disease, some individuals are undoubtedly "well" because they do not inherit any (or all) of the requisite susceptibility alleles for BPAD. In addition, since the age of greatest liability for onset of BPAD in the Old Order Amish is from early teens through 24 years of age, the misspecification of the "well" phenotype for individuals who will eventually develop BPAD would be greatest through this age period. In these Old Order Amish families susceptibility alleles for BPAD probably occur in very high frequency. Accordingly, an important step in our study which demonstrates that there are "protective" alleles was to show that there are "mentally healthy" individuals who share marker alleles that should increase the risk of developing BPAD, and yet, in the presence of "protective" alleles these individuals do not manifest BPAD. The effect "protective" alleles comes from pedigree 110, suggesting that such alleles may be more likely in this branch of the family. However, highly significant test statistics and multipoint lod scores (using GENEHUNTER-PLUS) are also observed when pedigrees 110, 210, 310 and 410 are used for analyses (FIGS. 12A and 12B). The decreased sharing in proportion of alleles identical by descent (IBD) for discordant pairs provides further support for the existence of alleles associated with the absence of affective disorder (mental health "wellness") in these families (Table 11). In addition, epistatic interactions between alleles could also prevent or delay an illness such as major depressive disorder from developing into BPAD. Indeed, as we increase the "age of risk" cutoff for defining the "well" phenotype from 25 to 45 years in our linkage analyses, the number of mentally healthy members decreases as expected, yet the evidence for linkage increases (Tables 9 and 10).

TABLE 11

SIBPAL analysis for concordant and discordant pair

| Marker | Number of Affected Sibs (# pairs in 110/all) | Pedigree 110 | | | Pedigrees 110, 210, 310, 410 | | |
|---|---|---|---|---|---|---|---|
| | | $\hat{\Pi}$ (s.e.) | P-value nominal | P-value simulated | $\hat{\Pi}$ (s.e.) | P-value nominal | P-value simulated |
| CHROMOSOME 4p | | | | | | | |
| D4S2949 | 0 (37/60) | .7077(.0202) | $<1 \times 10^{-7}$ | $<1 \times 10^{-5}$ | .6888(.0243) | $<1 \times 10^{-7}$ | $<1 \times 10^{-5}$ |
| | 1 (30/52) | .5094(.0360) | .6018 | np | .4177(.0337) | .0089 | .0145 |
| | 2 (17/20) | .4183(.0608) | .9021 | np | .4559(.0537) | .7897 | np |
| CHROMOSOME 4q | | | | | | | |
| D4S175 | 0 (35/43) | .5960(.0558) | .0471 | .0636 | .5995(.0484) | .0231 | .0348 |
| | 1 (27/38) | .4875(.0611) | .4194 | np | .4969(.0513) | .4762 | np |
| | 2 (17/19) | .4733(.0528) | .6901 | np | .4533(.0533) | .8042 | np |
| D4S397 | 0 (35/43) | .7511(.0449) | $3 \times 10^{-7}$ | .0009 | .6586(.0376) | $5 \times 10^{-6}$ | .0002 |
| | 1 (27/38) | .4536(.0460) | .1599 | np | .5069(.0358) | .5760 | np |
| | 2 (17/19) | .5000(.0404) | .5000 | np | .5116(.0419) | .3926 | np |
| D4S3334 | 0 (37/66) | .5491(.0254) | .0304 | .0497 | .5258(.0287) | .1858 | .1769 |
| | 1 (30/56) | .4119(.0368) | .0113 | .0089 | .4515(.0317) | .0655 | np |
| | 2 (17/20) | .4457(.0595) | .8133 | np | .4556(.0564) | .7805 | np |

$\hat{\Pi}$ is the estimated proportion of alleles shared identical by decent.
Number of affecteds:
0 = mentally healthy (well) sib pairs (older than age 45 years)
1 = discordant sib pairs
2 = BPI sib pairs
np: not performed of age for inclusion for the "wellness" phenotype can be seen in Tables 9 and 10. For many of the markers, $\hat{\Pi}$, an underestimate of the proportion of alleles shared identical by descent (IBD) in "well" sibpairs, increases with increasing age, i.e. a more stringent definition of the "well" phenotype. For example, with respect to marker D4S2949 on 4p, $\hat{\Pi}$ is 0.60, 0.65 and 0.71 for age cutoff points of 25, 35, and 45 years, respectively. This suggests that increasing the age for inclusion eliminates some age-related "well" phenocopies.

It is conceivable that virtually all cases of affective disorder in these families are due to a common set of susceptibility alleles. The "wellness" or "protective" loci that we have tentatively identified could harbor alleles that prevent the manifestation of a bipolar affective spectrum disorder phenotype, which could also include major depressive disorder. In our analyses the strongest evidence for There is some debate on the analysis of sibling pairs as to whether the use of inbred sibling pairs results in an increased number of false-positives if allele-sharing-based statistical methods are used (Genin, E. & Clerget-Darpoux, F. (1996) Am. J. Hum. Genet. 59, 1149–1162). However, the arguments that a) inbred sibling pairs are likely to share more genes than non-inbred sibling pairs (i.e., have a kinship factor greater than 0.5) and b) that greater regions of the genome would show significant deviations from the expected non-inbred sibling sharing value of 0.5, are incorrect when one is merely considering an analysis of sibling pairs involving only the transmission of alleles from parents to offspring. The transmission of alleles from parents to offspring will follow Mendelian ratios, and thus the null values for 0, 1, or 2 IBD sibling allele sharing in any population will be 0.25, 0.50, and 0.25, whenever only parental and sibling genotype information is used. However, if the origin of the parental alleles is taken into consideration, then there will be greater information about alleles shared by sibling pairs from inbred populations. For example, this increased informativeness has the potential to resolve ambiguities in the sharing of alleles transmitted from homozygous parents, since the two copies of the allele in an inbred homozygous parent could be IBD. This information could also help resolve alleles shared by siblings identical in state into alleles shared IBD, showing that alleles transmitted to two offspring from different parents may be copies of the same allele because of the relatedness of the parents. If genealogy is taken into account, then the increased ability to resolve ambiguities in allele sharing would result in greater power in the analysis of inbred sibling pairs (Genin, E. & Clerget-Darpoux, F., supra.).

Ultimately, if inbreeding exists in a population from which sibling pairs have been gathered, but one ignores genealogical information by merely studying the transmission of alleles from parents to offspring, then no increase in false-positive linkage results will occur. This is because Mendel's law applies to inbred as well as outbred parent-offspring allele transmission studies. On the contrary, a decrease in power may result from inbred sibling pair analyses because spouses may manifest greater homozygosity and therefore provide less informative genotypes for parent-offspring-based linkage studies.

Genetic mapping of complex disorders with multifactorial inheritance could be especially difficult if, in addition to susceptibility alleles, individuals inherit "protective" alleles that prevent or reduce the risk of manifesting the disease phenotype. Even though model-based linkage analyses that do not allow for a multifactorial component are of only limited usefulness in these circumstances, they are still frequently employed. In these instances, a false negative linkage finding (type 2 error) could result when individuals inherit disease susceptibility alleles but do not manifest the phenotype due to the simultaneous presence of "protective" alleles. If model-based methods are used, it is important to provide a reasonably low estimate of penetrance and include a multifactorial component in the model.

In the initial stages of analyzing a disorder like BPAD which most likely displays multifactorial inheritance, robust model-free (allele sharing) methods are usually more useful than model-based linkage analysis (Elston, R. C. (1995) *Exp. Clin. Immunogenet.* 12, 129–140). Concordant individuals should demonstrate excess allele sharing, even with the occurrence of phenocopies, genetic heterogeneity, high frequency of susceptibility alleles, and incomplete penetrance. Individuals who inherit susceptibility alleles but do not manifest disease because of "protective" alleles, and individuals who inherit "protective" alleles but nevertheless manifest the disease will reduce the power of these analyses. Thus, regardless of the type of linkage analysis performed, the presence of "protective" alleles could have a major impact on identifying susceptibility loci.

Although the idea that "protective" alleles could modify (or even prevent) a behavioral phenotype like BPAD is relatively novel, there are examples where such "protective" alleles can affect the expression or inheritance of other Mendelian and multifactorial disorders. The severity of sickle cell anemia is influenced by genes that increase the amount of circulating fetal hemoglobin (Perrine et al. (1972) *Lancet* 2, 1163–1167). Similarly, the genotype of the chemokine receptor CCR5 dramatically influences the kinetics of HIV-1 infection, where most individuals who are homozygous for a 32 bp deletion in the CCR5 gene encoding the coreceptor for macrophage-tropic HIV-1 are "protected" from virus infection (Picchio et al. (1997) *J. Virology* 71, 7124–7127). In Alzheimer's disease, ApoE2, in contrast to ApoE4, appears to reduce the relative risk of developing the disease and may protect individuals who inherit a disease-associated ApoE4 allele (Corder et al. (1994) *Nat. Genet.* 7: 180–183). In an extended Italian family, apolipoprotein A-I$_{MILANO}$ protects against the development of both clinical and pathologic signs of atherosclerosis, despite significantly elevated plasma triglycerides and a markedly decreased level of HDL-cholesterol (Franceschini et al. (1980) *J. Clin. Invest.* 66, 892–900). In the non-obese diabetic (NOD) mouse model of human autoimmune insulin-dependent diabetes mellitus, partial protection from disease is provided by "resistance" alleles occurring singly at either the Idd3 or Idd10 non-MHC loci, while epistatic interactions between "resistance" alleles at these two loci produces nearly complete protection from diabetes (Wicker et al. (1994) *J. Exp. Med.* 180, 1705–1713).

There are several mechanisms by which "wellness" or "protective" alleles could affect the clinical manifestations of BPAD in the Old Order Amish. One possibility is that dominant acting "protective" alleles, either singly or acting together in epistasis, could prevent or modify the BPAD phenotype. The variable penetrance of illness or its heterogeneous clinical manifestations could result from "resistance" or "protective" alleles that alone provide only partial protection, while together with other genes produce epistatic interactions resulting in a greater degree of modification of the phenotype. Alternatively, there also could be cellular target molecules, e.g. mood "effectors", having forms that are either resistant or susceptible to the genetic and/or environmental susceptibility factors for BPAD. Individuals having "resistant" mood effectors would be protected from the effects of susceptibility alleles and/or environmental factors that result in the BPAD phenotype. In contrast, individuals with "sensitive" forms of these mood effectors would be vulnerable to developing the BPI phenotype when requisite BPAD susceptibility alleles and/or environmental factors are present.

If epistatic interactions are required for manifestation of the effects of either susceptibility or "protective" alleles, the existence of "resistant" and "sensitive" forms of cellular effectors or "protective" alleles would be most apparent in families (or populations) where there is a high density of affected individuals such as the Old Order Amish in the present study. Regardless of the mechanism, the presence of "wellness" or "protective" alleles can have a significant impact on linkage analyses as evidenced by preventing the appearance of the BPAD phenotype (or its presentation as a forme fruste) in individuals who are otherwise genetically predisposed to developing illness.

Accordingly, a multilocus approach that considers both additive and subtractive influences of alleles on the BPAD phenotype is preferred in the identification of chromosomal loci harboring genes that contribute to the clinical manifestations of BPAD. The involvement of "protective" or "wellness" alleles in determining the manifestation of the BPAD phenotype provides an attractive explanation for at least some of the difficulty encountered in searches for BPAD susceptibility alleles. The test statistics from our analyses for alleles linked to the absence of psychiatric illness in the Old Order Amish are at least as significant as those reported for any susceptibility locus. The identification and characterization of "protective" alleles and their gene products can lead to the development of a more rational and direct approach to effective therapy for affective disorders.

All publications and patents mentioned in this specification are incorporated herein by reference into the specification to the same extent as if each individual publication or patent was specifically and individually indicated to be incorporated herein by reference.

What is claimed is:

1. A method of screening for a genotype associated with increased resistance to familial bipolar affective disorder in a family affected by bipolar affective disorder, comprising:
   a) selecting at least one marker located in a chromosomal region inclusive of and localized between D4S431 and D4S404;
   b) determining the presence or absence of the marker for at least one family member in a family affected by bipolar affective disorder, thereby determining a genotype of the family member;
   c) determining, after the age of onset, the bipolar affective disorder disease status in the family member;
   d) correlating the genotype with the bipolar affective disorder disease status of the family member; and
   e) determining therefrom a genotype associated with increased resistance to bipolar affective disorder.

2. The method of claim 1, wherein the chromosomal region is inclusive of and localized between markers D4S3007 and D4S419.

3. The method of claim 2, wherein the marker is D4S3007, D4S394, D4S2983, D4S2923, D4S615, AFM$_b$184za9, D4S2928, D4S1065, D4S1582, D4S107, D4S3009, D4S2906, D4S2949, AFM087zg5, D4S2944, D4S403, D4S2942, D4S2984, D4S1602, D4S1511, D4S2311, D4S3048, or combinations thereof.

4. The method of claim 3, wherein the marker is D4S3009, D4S2906, D4S2949, AFMO87zg5, D4S2944, D4S403, D4S2942, D4S2984, D4S1602, D4S1511, D4S2311, or combinations thereof.

5. The method of claim 1, wherein at least three markers are selected.

6. The method of claim 1, wherein the marker is for a restriction fragment length polymorphism or microsatellite polymorphism.

7. The method of claim 1, wherein the marker is amplified.

8. The method of claim 7, wherein the marker is amplified by the polymerase chain reaction.

9. The method of claim 1, wherein the genotype of an affected family member is determined.

10. The method of claim 1, wherein the genotype of a non-affected family member is determined.

11. The method of claim 1, further comprising:
    a) selecting at least one additional marker located in a chromosomal region inclusive of and localized between D6S344 and D6S89; inclusive of and localized between D13S171 and D13S218; or at about D15S148; and
    b) determining the presence or absence of the additional marker for at least one family member in a family affected by bipolar affective disorder.

12. The method of claim 1, wherein b) through d) are carried out for at least two family members.

* * * * *